US008133903B2

(12) United States Patent
Gonzalez-Cadavid et al.

(10) Patent No.: US 8,133,903 B2
(45) Date of Patent: Mar. 13, 2012

(54) METHODS OF USE OF INHIBITORS OF PHOSPHODIESTERASES AND MODULATORS OF NITRIC OXIDE, REACTIVE OXYGEN SPECIES, AND METALLOPROTEINASES IN THE TREATMENT OF PEYRONIE'S DISEASE, ARTERIOSCLEROSIS AND OTHER FIBROTIC DISEASES

(75) Inventors: Nestor F. Gonzalez-Cadavid, Pasadena, CA (US); Jacob Rajfer, Rolling Hills Est, CA (US)

(73) Assignee: Los Angeles Biomedical Research Institute at Harbor—UCLA Medical Center, Torrance, CA (US)

( * ) Notice: Subject to any disclaimer, the term of this patent is extended or adjusted under 35 U.S.C. 154(b) by 556 days.

(21) Appl. No.: 10/779,069

(22) Filed: Feb. 13, 2004

(65) Prior Publication Data
US 2005/0085486 A1    Apr. 21, 2005

(30) Foreign Application Priority Data

Oct. 21, 2003  (WO) .................. PCT/US03/33400

(51) Int. Cl.
*A01N 43/42*    (2006.01)
(52) U.S. Cl. ........................................ 514/310
(58) Field of Classification Search ............ 514/310
See application file for complete search history.

(56) References Cited

U.S. PATENT DOCUMENTS

| 5,482,039 | A | * | 1/1996 | Place ........................ 128/653.1 |
| 5,824,669 | A | | 10/1998 | Garvey et al. |
| 5,981,563 | A | | 11/1999 | Lowrey |
| 5,990,103 | A | | 11/1999 | Schonharting et al. |
| 6,127,363 | A | * | 10/2000 | Doherty et al. ............... 514/220 |
| 6,143,746 | A | | 11/2000 | Daugan et al. |

(Continued)

FOREIGN PATENT DOCUMENTS

CA    2351904    12/2001

(Continued)

OTHER PUBLICATIONS

Burdick et al, CXCL11 Attenuates Bleomycin-induced Pulmonary Fibrosis via Inhibition of Vascular Remodeling, American Journal of Respiratory and Critical Care Medicine vol. 171, pp. 261-268, printed pp. 1-5, especially page 1.*

(Continued)

*Primary Examiner* — Sreeni Padmanabhan
*Assistant Examiner* — Timothy E Betton
(74) *Attorney, Agent, or Firm* — Blakely Sokoloff Taylor & Zafman LLP

(57) ABSTRACT

The present methods and compositions are of use for treatment of conditions involving fibrosis, such as Peyronie's disease plaque, penile corporal fibrosis, penile veno-occlusive dysfunction, Dupuytren's disease nodules, vaginal fibrosis, clitoral fibrosis, female sexual arousal disorder, abnormal wound healing, keloid formation, general fibrosis of the kidney, bladder, prostate, skin, liver, lung, heart, intestines or any other localized or generalized fibrotic condition, vascular fibrosis, arterial intima hyperplasia, atherosclerosis, arteriosclerosis, restenosis, cardiac hypertrophy, hypertension or any condition characterized by excessive fibroblast or smooth muscle cell proliferation or deposition of collagen and extracellular matrix in the blood vessels and/or heart. In certain embodiments, the compositions may comprise a PDE-4 inhibitor, a PDE-5 inhibitor, a compound that elevates cGMP and/or PKG, a stimulator of guanylyl cyclase and/or PKG, a combination of a compound that elevates cGMP, PKG or NO with an antioxidant that decreases ROS, or a compound that increases MMP activity.

5 Claims, 21 Drawing Sheets

U.S. PATENT DOCUMENTS

| | | | |
|---|---|---|---|
| 6,174,845 B1 | 1/2001 | Rattinger et al. | |
| 6,177,471 B1 | 1/2001 | Menander et al. | |
| 6,284,763 B1 | 9/2001 | Adams et al. | |
| 6,331,543 B1 * | 12/2001 | Garvey et al. | 514/250 |
| 6,403,597 B1 * | 6/2002 | Wilson et al. | 514/256 |
| 6,458,797 B1 * | 10/2002 | Adams et al. | 514/258 |
| 6,525,100 B1 * | 2/2003 | Easterling et al. | 514/654 |
| 6,794,192 B2 | 9/2004 | Parums et al. | |
| 2003/0216407 A1 | 11/2003 | Butt et al. | |

FOREIGN PATENT DOCUMENTS

| | | |
|---|---|---|
| EP | 0 930 069 A2 | 7/1999 |
| EP | 1 048 666 A1 | 11/2000 |
| EP | 1 092 719 B1 | 5/2003 |
| WO | WO 99/26946 A1 | 6/1999 |
| WO | WO 00/64424 A2 | 11/2000 |
| WO | WO 01/47901 A1 | 7/2001 |
| WO | WO 01/51042 A2 | 7/2001 |
| WO | WO 02/02118 A1 | 1/2002 |
| WO | WO 02/15893 A2 | 2/2002 |

OTHER PUBLICATIONS

Ma et al. (Therapeutic effect of phosphodiesterase-5 inhibitor on pathological changes of tunica albuginea in erectile dysfunction: experiment with rats), Zhonghua Yi Xue Za Zhi. Feb. 3, 2009; 89(4): 276-9.*

Alves, M.A., et al.: L-Arginine effects on blood pressure and renal function of intrauterine restricted rats. Pediatr Nephro (2002) 17:856-862.

Anderson, MS, et al.: Inhibition of Peyronie's plaque fibroblast proliferation by biologic agents. *Int J Impot Res* (2000) 12 Suppl 3, S25-31.

Arthur, MJ.: Fibrogenesis II. Metalloproteinases and their inhibitors in liver fibrosis. Am J Physiol. Soc. (2000) 279: G245-G249.

Asai, K, et al.: Peripheral vascular endothelial dysfunction and apoptosis in old monkeys. Arterioscler Thromb Vasc Biol. (2000) 20(6):1493-1499.

Badalamente, MA, et al.: The role of transforming growth factor beta in Dupuytren's disease. *Journal of Hand Surg* (1996) 21A(2): 210-215.

Becker, GJ, et al.: Pharmacological intervention in renal fibrosis and vascular sclerosis. J. Nephrol. (2001) 14:332-339.

Beckmann, JS, Koppenol WH: Nitric oxide, superoxide, and peroxynitrite: the good, the bad, and the ugly. *Am J Physiol* (1996) 271:C1424-C1437.

Behr-Roussel, D, et al.: Effect of chronic treatment with the inducible nitric oxide synthase inhibitor N-iminoethy-L-lysine or with L-arginine on progression of coronary and aortic atherosclerosis in hypercholesterolemic rabbits. Circulation 2000; 102:1033-1038.

Benigni, A, et al.: Renoprotection by nitric oxide donor and lisinopril in the remnant kidney model. *Am J Kidney Dis* (1999) 33(4):746-53.

Berry, C, et al.: Oxidative stress and vascular damage in hypertension. Curr Opin Nephrol Hypertens. (2001) 10:247-255.

Bing, W, et al.: L-arginine impacts pulmonary vascular structure in rats with an aortocaval shunt. J Surg Res (2002)108:20-31.

Bivalacqua, TJ, et al.: Gene transfer of extracellular SOD to the penis reduces $O_2$-• and improves erectile function in aged rats. Am J Physiol Heart Circ Physiol. (2003) 284:H1408-1421.

Bivalacqua, TJ et al.: A rat model of Peyronie's disease associated with a decrease in erectile activity and an increase in inducible nitric oxide synthase protein expression. *Jour Urol* (2000) 163:1992-1998.

Boffa, JJ, et al.: Angiotensin II activates collagen type I in the renal vasculature of transgenic mice during inhibition of nitric oxide synthesis: evidence for an endothelin-mediated mechanism. *Circulation* (1999) 100(18):1901-1908.

Boger, RH, et al.: Asymmetric dimethylarginine (ADMA): a novel risk factor for endothelial dysfunction: its role in hypercholesterolemia. *Circulation* (1998) 98:1842-1847.

Bugno, M, et al.: Reprogramming of TIMP-1 and TIMP-3 expression profiles in brain microvascular endothelial cells and astrocytes in response to proinflammatory cytokines. *FEBS Lett* (1999) 448(1):9-14.

Cai, H, Harrison DG: Endothelial dysfunction in cardiovascular diseases: the role of oxidant stress. Circ Res. (2000) 87:840-844.

Cao, M, et al.: Nitric oxide inhibits the synthesis of type-II collagen without altering Col2A1 mRNA abundance: prolyl hydroxylase as a possible target. *Biochem J* 324:305-310.

Casini, A, et al.: Neutrophil-derived superoxide anion induces lipid peroxidation and stimulations collagen synthesis in human hepatic stellate cells: role of nitric oxide. *Hepatology* (1997) 25(2):361-367.

Catani, MV, et al.: Inhibition of clotting factor XIII activity by nitric oxide. *Biochem Biophys Res Comm* (1998) 249:275-278.

Cattell, V: Nitric oxide and glomerulonephritis. *Kidney Int* (2002) 61(3):816-21.

Cernadas, MR, et al.: Expression of constitutive and inducible nitric oxide synthases in the vascular wall of young and aging rats. Circ Res. (1998) 83:279-286.

Chan, DC, et al.: Exisulind in combination with docetaxel inhibits growth and metastasis of human lung cancer and prolongs survival in athymic nude rats with orthotopic lung tumors. *Clin Cancer Res* (2002) 8(3):904-912.

Chatziantoniou, C, et al.: Nitric oxide inhibition induces early activation of type I collagen gene in renal resistance vessels and glomeruli in transgenic mice. Role of endothelin. *J Clin Invest* (1998) 101(12):2780-2789.

Chen, YM, Wu KD, Tsai TJ, Hsieh BS: Pentoxifylline inhibits PDGF-induced proliferation of and TGF-beta-stimulated collagen synthesis by vascular smooth muscle cells, *J Mol Cell Cardiol* (1999) 31(4):773-783.

Chiche JD, et al.: Adenovirus-mediated gene transfer of cGMP-dependent protein kinase increases the sensitivity of cultured vascular smooth muscle cells to the antiproliferative and pro-apoptotic effects of nitric oxide/cGMP. *J Biol Chem* (1998) 273(51):34263-34271.

Chipe, CC, et al.: Myofibroblast phenotype and apoptosis in keloid and palmar fibroblasts in vitro, *Cell Death & Differ* (2000) 7(2)166-176.

Chou, T, et. al.: Alterations of nitric oxide synthase expression with aging and hypertension in rats. Hypertension. (1998) 31:643-648.

Connat, JL, et al.: Modification of the rat aortic wall during ageing; possible relation with decrease of peptidergic innervation. Anat Embryol. (2001) 204:455-468.

Connelly TJ: Development of Peyronie's and Dupuytren's diseases in an individual after single episodes of trauma: a case report and review of the literature. *J Am Acad Dermatol* (1999) 41(1):106-108.

Corbin, JD, Francis SH: Cyclic GMP phosphodiesterase-5: target of sildenafil. *J Bio Chem* (1999) 274(20):13729-13732.

Craven, PA, et al.: Nitric oxide inhibition of transforming growth factor-beta and collagen synthesis in mesangial cells. *Diabetes* (1997) 46:671-681.

Csiszar, A, et al.: Aging-induced phenotypic changes and oxidative stress impair coronary arteriolar function. Circ Res. (2002) 90:1159-1166.

Curtin, JF, Donovan M, Cotter TG: Regulation and measurement of oxidative stress in apoptosis. *J Immunnol Methods* (2002) 265:49-72.

Dambisya, YM, et al: A thromboelastography study on the in vitro effects of L-arginine and L-NG-nitro arginine methyl ester on human whole blood coagulation and fibrinolysis. *Blood Coagul Fibrinol* (1996) 7:678-683.

Darby, IA, et al.: Skin flap-induced regression of granulation tissue correlates with reduced growth factor and increased metalloproteinase expression. *J Pathol,* (2002) 197(1):117-127.

Davila, HH, et al.: Gene transfer of antisense PIN (protein inhibitor of NOS) cDNA on erectile dysfunction in aged rats. American Urological Association Meeting, Chicago, IL 2003.

Dávila, M, et al.: Fibrin as an inducer of fibrosis in the tunica albuginea the rate: a new animal model for Peyronie's disease. Br. J. Urol. (2003) 91:830-838.

Demaree, SR, et al.: Ageing alters aortic antioxidants enzyme activites in Fischer-344 rats. Acta Physiol Scand. (1999) 166:203-208.

Desmoulière, A: Factors influencing myofibroblasts differentiation lduring would healing and fibrosis, *Cell Biol Interntl* (1995) 19(5):471-476.

Desmouliere, A, et al.: Effect of pentoxifylline on early proliferation and phenotypic modulation of fibrogenic cells in two rat models of liver fibrosis and on cultured hepatic stellate cells. *J Hepatol* (1999) 30(4): 621-631.

Devine, CJ Jr, et al.: Proposal: trauma as the cause of the peyronie's lesion. *J Urol* (1997) 157(1):285-290.

Diegelmann, RF: Cellular and biochemical aspects of normal and abnormal wound healing: an overview. *J Urol* (1997) 157:298-302.

Duffield, JS, et al.: Activated macrophages direct apoptosis and suppress mitosis of mesangial cells. *J Immunol* (2000) 164(4):2110-2119.

Duncan, MR, et al.: Regulation of the proliferation and biosynthetic activities of cultured human Peyronie's disease fibroblasts by interferons-alpha, -beta and -gamma. *Scand J Urol Nephrol* (1991) 25(2):89-94.

Dussaule, JC, et al.: Mechanisms mediating the renal profibrotic actions of vasoactive peptides in transgenic mice. *J Am Soc Nephrol Suppl* (2000) 11(16):S124-8.

Ehrlich, HP: Scar contracture: cellular and connective tissue aspects in yronie's disease. *J Urol* (1997) 157:316-319.

Eickelberg, O, et al.: Extracellular matrix deposition by primary human lung fibroblasts in response to TGF-beta1 and TGF-beta3. Am J Physiol. (1999) 276(5 Pt 1): L814-24.

El-Sakka, AI, et al.: The effects of colchicine on a Peyronie's-like condition in an animal model. *J Urol* (1999) 161:1980-1983.

El-Sakka, AI, et al.: Histological and ultrastructural alterations in an animal model of Peyronie's disease, *British J Urol* (1998) 81:445-452.

El-Sakka, AI, et al.: An animal model of Peyronie's-like condition associated with an increase of transforming growth factor beta mRNA and protein expression. *J Urol* (1997) 158:2284-2290.

El-Sakka, AI, et al.: Peyronie's disease is associated with an increase in transforming growth factor-beta protein expression. *J Urol* (1997) 158:1391-4.

Essayan, DM: Cyclic nucleotide phosphodiesterases, J. Allergy Clin. Immunol. (2001) 108:671-680.

Fakhouri, F, et al.: Angiotensin II activates collagen type I gene in the renal cortex and aorta of transgenic mice through interaction with endothelin and TGF-beta. *J Am Soc Nephrol* (2001) 12(12):2701-10.

Fan, J, et al.: Priming for enhanced alveolar fibrin deposition after hemorrhagic shock: role of tumor necrosis factor. *Am J Respir Cell Mol Biol* (2000) 22(4):412-21.

Faouzi, S, et al.: Myofibroblasts are responsible for collagen synthesis in the stroma of human hepatocellolar carcinoma: an in vivo and in vitro study. *J Hepatol* (1999) 30:275-284.

Ferrini, M, et al.: Aging-telated expression of inducible nitric oxide sunthase (iNOS) and cytotoxicity markers in the rat penis. *Biol Reprod* (2001) 64:974-982.

Ferrini, M, et al.: Aging-related expression of inducible nitric oxide synthase (iNOS) and cytotoxicity markers in rat hypothalamic regions associated with male reproductive function. *Neuroendocr* (2001) 74:1-11.

Ferrini, MG, et al.: Penile neuronal nitric oxide synthase (PnNOS) and its regulatory proteins are present in hypothalamic and spinal cord regions involved in the control of penile erection. *J Compar Neurol*, (2003) 458:46-61.

Ferrini, MG, et al.: Antifibrotic role of inducible nitric oxide synthase (iNOS). *Nitric Oxide* (2002) 6(3):283-294.

Fischer, M, et al.: Crux medicorum ulcerated radiation-induced fibrosis—successful therapy with pentoxifylline and vitamin E. *Eur J Dermatol* (2001) 11(1): 38-40.

Foresti, R, et al.: Peroxynitrite induces haemoxygenase-1 in vascular endothelial cells: a link to apoptosis. *Br Biochem J* (1999) 339:729-736.

Fornieri, C, et al.: Role of the extracellular matrix in age-related modifications of the rat aorta. Ultrastructural, morphometric, and enzymatic evaluations. Arterioscler Thromb. (1992) 12(9):1008-1016.

Forstermann, U, et al.: Expressional control of the "constitutive" isoforms of nitric oxide synthase (NOS I and NOS III). *FASEB J* (1998) 12:773-790.

Garban, H, et al.: Cloning of rat and human inducible penile nitric oxide synthase. Application for gene therapy of erectile dysfunction. *Biol Reprod* (1997) 56:954-963.

Garban, H, et al.: Effect of aging on nitric oxide-mediated penile erection in the rat. Amer. J. Physiol. (1995) 268:H467-H475.

Gelbard, MK: Dystrophic penile calcification in Peyronie's disease. *J Urol* (1988) 139(4)738-40.

Geller, DA, Billiar TR: Molecular biology of nitric oxide synthases. *Cancer Metast Rev* (1998) 17:7-23.

Gelman, J, et al.: Transforming growth factor -beta1 (TGF-beta1) in penile and prostate growth in the rat during sexual maturation. *J Androl* (1998) 19(1):50-57.

Gewaltig, MT, Kojda G: Vasoprotection by nitric oxide: mechanisms and therapeutic protential. Cardivasc Res. (2002) 55:250-260.

Gholami, SS, et al.: Peyronie's Disease: A review. *J Urol*, (2003) 169:1234-1241.

Goettsch, W, et al: Increased expression of endothelin-1 and inducible nitric oxide synthase isoform II in aging arteries in vivo: implications for atherosclerosis. Biochem Biophys Res Commun. (2001) 280:908-913.

Gonzalez, W, et al.: Molecular plasticity of vascular wall during N(G)-nitro-L-arginine methylester-induced hypertension: modulation of proinflamatory signals. Hypertension (2000) 36:103-109.

González-Cadavid, NF, et al.: Nitric oxide and the cyclic GMP system in the penis. Mol Urol. (1999) 3(2):51-59.

Gonzalez-Cadavid, NF, et al.: Gene expression in Peyronie's disease. Int. J. Impot. Res. (2002) 14:361-374.

Grein, U, et al.: Arteriosclerosis of penile arteries: histolgical findings and their significance in the treatment of erectile dysfunction. Urol. Int. (2002) 68:261-264.

Grounds, MD, et al.: The role of stem cells in skeletal and cardiac muscle repair. *J Histochem Cytochem* (2002) 50(5):589-610.

Haig, DM, Thomson, Percival A: The in-vitro detection and quantitation of ovine bone marrow precursors of multipotential colony-forming cells. *J Comp Path*. (1994) 111(1):73-85.

Heigold, S, et al.: Nitric oxide mediates apotosis induction selectively in transformed fibroblast compared to nontransformed fibroblasts. *Carcinogenesis* (2002) 23(6):929-941.

Hellstrom, WJ, Bivalacqua TJ: Peyronie's disease: etiology, medical, and surgical therapy. *J Androl* (2000) 21(3):347-354.

Hellstrom, WJG, Bivalacqua J, Champion, HC, et al.: Evaluation of nitric oxide synthase and arginase in the induction of a Peyronie's-like condition in the rat. J Androl (2001) 22(3):497-508.

Herrick, S, et al.: Fibrinogen. *Int J Biochem Cell Biol* (1999) 31(7):741-6.

Higuchi, H, et al.: Assay of antioxidant and anti-flammatory activity of nitric oxide in vivo. *Meth Enzymol* (1999) 301:424-436.

Hildebrand, KA, et al.: Response of donor and recipient cells after transplantation of cells to the ligament and tendon. *Microsc. Res. Tech*. (2002) 58(1):34-38.

Hochberg, D, et al.: Interstitial fibrosis of unilateral ureteral obstruction is exacerbated in kidneys of mice lacking the gene for inducible nitric oxide synthase. *Lab Invest* (200) 80(11):1721-1728.

Hofmann, F, et al.: Rising behind NO: cGMP-dependent protein kinases. *J Cell Sci* (2000) 113:1671-6.

Hoaboam, CM, et al.: Collagen deposition in a non-fibrotic lung granuloma model after nitric oxide inhibition. *Am J Pathol* (1998) 153(6):1861-1872.

Holm, AM, et al.: Effects of L-arginine on vascular smooth muscle cell proliferation and apoptosis after balloon injury. Scand. Cardiovasc J. (2000) 34:28-32.

Holmdahl, L, et al.: Overproduction of transforming growth factor-beta1 (TGF-beta1) is associated with adhesion formation and peritoneal fibrinolytic impairment. *Surgery* (2001) 129(5)626-632.

Horio, T, et al.: Effects of adrenomedullin on cultured rat cardiac myocytes and fibroblasts. *Eur J Pharmacol* (1999) 382(1):1-9.

Huff, T, et al.: beta-Thymosins, small acidic peptides with multiple functions. Int J Biochem Cell Biol (2001) 33(3): 205-220.

Huff, T, et al.: Thymosin beta4 is released from human blood platelets and attached by factor XIIIa (transglutaminase) to fibrin and collagen. FASEB J. (2002) 16(7):691-696.

Hung, A, et al.: Expression of the inducible nitric oxide synthase in smooth muscle cells from the rat penile corpora cavernosa. *J Androl* (1995) 16(6):469-481.

Ihrig, M, et al.: Mice lacking inducible nitric oxide synthase develop spontaneous hypercholesterolaemia and aortic atheromas. Atherosclerosis. (2001) 156:103-107.

Ikeda, K, et al.: Nitric oxide deficiency induces myocardial infarction in hypercholesterolemic stroke-prone spontaneously hypertensive rats. Clin Exptl Pharmacol Physiol (1997) 24:344-8.

Intengan, HD, Schiffrin EL: Structure and mechanical properties of resistance arteries in hypertension: role of adhesion molecules and extracellular matrix determinants. Hypertension. (2000) 36:312-318.

Intengan, HD, Schiffrin EL: Vascular remodeling in hypertension. Roles of apoptosis, inflammation, and fibrosis. Hypertension. (2001) 38[part 2]: 581-587.

Ito, S, et al.: Induction of glomerular injury by singlet oxygen. *Nephron* (1992) 60(2):204-9.

Iredale, JP: Tissue inhibitors of metalloproteinases in liver fibrosis. *Int J Biochem Cell Biol* (1997) 29(1):43-54.

Jarow, JP, Lowe FC: Penile trauma: an etiolgic factor in Peyronie's disease and erectile dysfunction. *J Urol* (1997) 158(4):1388-90.

Jenkins, JK, et al.: Vitamin E inhibits renal mRNA expression of COX II, HO I, TGFbeta, and osteopontin in the rat model of cyclosporine nephrotoxicity. *Transplantation* (2001) 71(2):331-4.

Kaikita, K, et al: Potential roles of plasminogen activator system in coronary vascular remodeling induced by long-term nitric oxide synthase inhibition. J Mol Cell Cardiol. (2002) 34:617-627.

Kelley, TJ, Drumm ML: Inducible nitric oxide synthase expression is reduced in cystic fibrosis murine and human airway epithelial cells. *J Clin Invest* (1998) 102:1200-1207.

Khan, MA, et al.: The effect of superoxide dismutase on nitric oxide-mediated and electrical field-stimulated diabetic rabbit cavernosal smooth muscle relaxation. BJU Int. (2001) 87:98-103.

Kibbe, M, et al.: Inducible nitric oxide synthase and vascular injury. *Cardiovasc Res* (1999) 43:650-657.

Kim, NN, et al.: Cross-regulation of intracellular cGMP and cAMP in cultured human corpus cavernosum smooth muscle cells. *Mol Cell Biol Res Commun* (2000) 4(1):10-14.

Kim, PK, et al.: The regulatory role of nitric oxide in apoptosis. *Int Immunopharmacol* (2001) 1(8):1421-41. Review.

Kitamoto, S, et al: Chronic inhibiton of nitric oxide synthesis in rats increases aortic superoxide anion production via the action of angiotensis II. J. Hypertens. (2000) 18:1795-1800.

Klar, S, Morrisey JJ: The role of growth, cytokines and vasoactive compounds in obstructive nephropathy. *Seminars Nephrol* (1998) 18(6):622-632.

Kleinman, HK: Thymosin beta4 accelerates wound healing. J Invest Dermatol (1999) 113(3):364-368.

Kloen, P: New insights in the development of Dupuytren's contracture: a review. Br J Plast Surg (1999) 52(8):629-635.

Kolpakov, V, et al.: Nitric oxide-generating compounds inhibits total protein and collegen synthesis in cultured vascular smooth muscle cells. *Circul Res* (1995) 76:305-309.

Krall, JF, et al.: Characterization of cyclic nucleotide and inositol 1,4,5-trisphosphate-sensitive calcium-exchange activity of smooth muscle cells cultured from the human corpora cavernosa. *Biol Reprod* (1998) 39(4):913-922.

Kremer, S, et al.: Effect of immunomodulators on bleomycin-induced lung injury. *Respiration* (1999) 66(5):455-462.

Kuthe, A. et al.: Expression of different phosphodiesterase genes in human cavernous smooth muscle. J. Urol (2001) 165:280-283.

Lai, T, et al.: Reversibility and pathohistological basis of left ventricular remodeling in hibernating myocardium. Cardiovasc. Pathol. (2000) 9:323-335.

Lee, PC, et al.: Role of inducible nitric oxide synthase in transplant arteriosclerosis. Clin Exp Pharmacol Physiol. (1999) 26:1013-1015.

Lee, KS, et al.: Overexpression of the thymosin beta-10 gene in human ovarian cancer disrupts F-actin stress fiber and leads to apoptosis. *Oncogene* (2001) 20:6700-6706.

Lee, KS, et al.: Pentoxifylline blocks hepatic stellate cell activation independently of phosphodiesterase inhibitory activity. Am. J. Physiol. 273 (1997) G1094-G1100.

Li, YY, et al.: Interplay of matrix metalloproteinases, tissue inhibitors of metalloproteinases and their regulators in cardiac matrix remodeling. Cadiovasc Res. (2000) 46:214-224.

Liang, L, et al.: The phosphodiesterase inhibitors pentoxifylline and rolipram prevent diabetes in NOD mice. Diabetes (1998) 47:570-575.

Lin, CS, et al.: Human PDE5A gene encodes three PDE5 isoforms from two alternate promoters. *Int J Impot Res* (2002) 14(1):15-24.

Lin, CS, et al.: Expression of three isoforms of cGMP-binding cGMP-specific phosphodiesterase (PDE5) in human penile cavernosum. *Biochem Biophys Res Commun* (2000) 268(2):628-635.

Lin, CS, et al.: Identification of three alternative first exons and an intronic promoter of human PDE5A gene. *Biochem Biophys Res Commun* (2000) 268(2):596-602.

Lin, RJ, et al.: KMUP-1 relaxes rabbit corpus cavernosum smooth muscle in vitro and in vivo: involvement of cycle GMP and K(+) channels. *Br J Pharmacol* (2002) 135(5):1159-1166.

Lin, S, et al.: Pentoxifylline attenuated the renal disease progression in rats with remnant kidney. J Am Soc Nephrol (2002) 13:2916-2929.

Loweth, AC, et al.: Evidence for the involvement of cGMP and protein kinase G in nitric oxide-induced apoptosis in the pancreatic B-cell line, HIT-T15. *FEBS Lett* (1997) 400(3):285-288.

Ma, K, et al.: Characterization of the 5' upstream regulatory region of the human myostatin gene. Regulation of myostatin gene transcription by dexamethasome. Am J Physiol (2001) 281:E1128-1136.

Magee, TR, et al.: Protein inhibitor of nitric oxide synthase (NOS) and the N-methyl-D-aspartate receptor are expressed in the rat and mouse penile nerves and colocalize with penile neuronal NOS. *Biol Reprod*, (2003) 68:478-488.

Magee, TR, et al.: Gene therapy of erectile dysfunction in the rat with penile neuronal nitric oxide synthase. *Biol Reprod*, (2002) 67:20-28.

Magee, TR, et al.: Gene expression profiles in the Peyronie's disease plaque. *Urology* (2002) 59:451-457.

Malinda, KM, et al.: Thymosin beta4 accelarates wound healing. Soc. Investigative Derm. (1999) 113(3):364-368.

Martin, W, et al.: NANC neurotransmission in the bovine retactor penis muscle is blocked by superoxide anion following inhibition of superoxide dismutase with diethyldithiocarbamate. Neuropharmacology. (1994) 33:1293-1301.

Melman, A: Pathophysiologic basis of erectile dysfunction. What can we learn from animal models? Int J Impot Res. (2001) 13:140-142.

Melman, A, et al.: The epidemiology and pathophysiology of erectile dysfunction. J Urol. (1999) 161:5-11.

Miller, MJ, et al.: Nitric Oxide. III. A molecular prelude to intestinal inflammation. *Am J Physiol* (1999) 276(4 Pt 1): G795-G799. Review.

Moilanen, M, et al.: Expression and regulation of collagenase-2 (MMP-8) in head and neck squamous cell carcinomas. *J Pathol* (2002) 197(1):72-81.

Moody, JA, et al.: Effect of long-term administration of L-arginine on the rate erectile response. *J Urol* (1997) 158:942-947.

Moore, MA, Schiffrin, EL: Consortium for Southeastern hypertsion control. Small artery remodeling in hypertension control. Small artery remodeling in hypertension: can it be corrected?. Am J Med Sci. (2001) 322(1):7-11.

Moreno, H Jr, et el.: Chronic nitric oxide inhibition as a model of hypertensive heart muscle disease. *Basic Res Cardiol* (1996) 91:248-255.

Mulhall, JP, et al.: Perturbation of cell cycle regulators in Peyronie's disease. *Int J Impot Res* (2001) 13 Suppl 5:S21-S28.

Mulhall, JP, et al.: Basic fibroblast growth factor expression in Peyronie's disease. *J Urol* (2001) 165(2):419-423.

Mulhall, JP, et al.: Peyronie's disease cell culture models: phenotypic, genotypic and functional analyses. Int. J. Impot. Res. (2002) 14:397-405.

Muriel, P: Nitric oxide protection of rat liver from lipid peroxidation, collagen accumulation, and liver damage induced by carbon tetrachloride. *Biochem Pharmacol* (1998) 56(6):773-779.

Muriel, P, et al.: Effects of S-Adenosyl-L-methionine and Interferon-alpha$_{2b}$ on liver damage induced by bile duct ligation in rats. J Appl Toxicol (1998) 18:143-147.

Nagase, H, et al.: Engineering of tissue inhibitor of metalloproteinases mutants as potential therapeutics. *Arthitis Res* (2002) 4 Suppl 3:S51-S61.

Nanji, AA, et al.: Arginine reverses ethanol-induced inflammatory and fibrotic changes in liver despite continued ethanol administration. J Pharmacol. Exp. Ther. (2001) 299(3):832-839.

Nathan, C: Inducible nitric oxide synthase: What difference does it make? *J Clin Invest* (1997) 100(10):2417-2423.

Nishio, E, et al.: Nitric oxide donor SNAP induces apoptosis in smooth muscle cells through cGMP-independent mechanism. Biochem. Biophys. Res. Commun. (1996) 221(1):163-168.

Niu, XL, et al.: Inducible nitric oxide synthase deficiency does not affect the susceptibility of mice to atherosclerosis but increases collagen content in lesions. Circulation. (2001) 103:1115-1120.

Noss, MB, et al.: The genetics and immunology of Peyronie's disease. *Int J Impot Res* (2000) 12 Suppl 4:S127-S132.

Noujaim, D, et al.: N-Myc and Bcl-2 coexpression induces MMP-2 secretion and activation in human neuroblastoma cells. Oncogene (2002) 21(29): 4549-4557.

Numaguchi, K, et al.: Chronic inhibition of nitric oxide synthesis causes coronary microvascular remodeling in rats. *Hypertension* (1995) 26(6 Pt. 1):957-962.

Okamoto, T, et al.: Activation of human neutrophil procollagenase by nitrogen dioxide and peroxynitrite: a novel mechanism for procollagenase activation involving nitric oxide. *Arch Biochem Biophys* (1997) 342(2):261-274.

Orucevic, A, et al.: Nitric-oxide production by murine mammary adenocarcinoma cells promotes tumor-cell invasivesness. *Int J Cancer* (1999) 81(6): 889-896.

Owens; MW, et al.: Inhibition of pleural mesothelial cell collagen synthesis by nitric oxide. *Free Radic Biol Med* (1996) 21(5): 601-607.

Pandey, KN, et al.: Natriuetic peptide receptor-A negatively regulates mitogen-activated protein kinase and proliferation of mesangial cells: role of cGMP-dependent protein kinase. *Biochem Biophys Res Commun* (2000) 271(2): 374-379.

Pechanova, O, et al.: L-NAME-induced protein remodeling and fibrosis in the rat heart. Physiol. Res. (1999) 48:353-362.

Peters, H., et al.: Tandem antifibrotic actions of L-arginine supplementation and low protein diet during the repair phase of experimental glomerulonephritis. Kidney Int. (2000) 57-992-1001.

Piazza, GA, et al.: Exisulind, a novel proapoptotic drug, inhibits rat urinary bladder tumorigenesis. Cancer Res. (2001) 61:3961-3968.

Poli, G: Pathogenesis of liver fibrosis: role of oxidative stress. *Mol Aspects Med* (2000) 21:49-98.

Powel, DW, et al.: Myofibroblasts. I. Paracrine cells important in health and disease. *Am J Physiol* (1999) 277:C1-C19.

Preaux, AM, et al.: Apoptosis of human hepatic myofibroblasts promotes activation of matrix metalloproteinase-2. *Hepatology* (2002) 36(3): 615-622.

Pye, D, et al.: Dermal fibroblasts participate in the formation of new muscle fibres when implanted into regenerating normal mouse muscle. *J Anat* (2001) 198:163-173.

Raetsch, C, et al.: Pentoxifylline downregulates profibrogenic cytokines and procollagen I expression in rat secondary biliary fibrosis. Gut (2002) 50:241-247.

Redondo, J, et al.: Effect of atrail natriuretic peptide and cyclic GMP phosphodiesterase inhibition on collogen synthesis by adult cardiac fibroblast. *Br J Pharmacol* (1998) 124(7):1455-1462.

Reimund, JM, et al.: In vitro effects of oxpentifylline on infammatory cytokine release in patients wth inflammatory bowel disease. Gut (1997) 40(4):475-80.

Reiz-Porszasz, S, et al.: Lower skeletal muscle mass in male transgenic mice with muscle-specific overexpression of myostatin. Am J Physiol Endocrinon Metab (2003) 285:E876-E888.

Rizvi, MA; et al.: Nitric oxide modulates basal and endothelin-induced coronary artery vascular smooth muscle cell proliferation and collagen levels. *J Mol Cell Cardiol* (1997) 29:1779-1789.

Rizzoni, D, et al: Time course of apoptosis in small resistance arteries of spontaneously hypertensive rats. J Hypertens. (2000) 18:885-891.

Robert, L.: Aging of the vascular-wall and atherosclerosis. Exp Gerontol. (1999) 34:491-501.

Rogers, RS, et al.: Intracavernosal vascular endothelial growth factor (VEGF) injection and adeno-associated virus-mediated VEGF gene therapy prevent and reverse venogenic erectile dysfunction in rats. Intl J Impot Res. (2003) 15:26-37.

Roy, SG, et al.: Regulation of alpha-smooth muscle actin gene expression in myofibroblast differentiation from rat lung fibroblasts. *Intl J Biochem & Cell Biol* (2001) 33:723-734.

Ryter, SW, et al.: Heme oxygenase-1: molecular mechanisms of gene expression in oxygen-related stress. *Antioxid Redox Signal* (2002) 4(4):625-632.

Salanova,M, et al.: Type 4 cyclic adenosine monophosphate-specific phosphodiesterases are expressed in discrete subcellular compartments during rat spermiogenesis. Endocrinology (1999)140: 2297-2306.

Sampson, LJ, et al.: Evidence for expression and function of phospho-diesterase type 5 (PDE-V) in rat resistance arteries. Br. J. Pharmacol. (2001) 132:13-17.

Sauzeau, V, et al.: Sildenafil prevents change in RhoA expression induced by chronic hypoxia in rat pulmonary artery. Circ Res. (2003) 93:630-637.

Schade, I, et al.: Benefit of phosphodiesterase 4 inhibitors as supplemental therapy after lung transplantation concerning their antiproliferative effects: an experimental study using a heterotopic rodent model. *Transplantation* (2002) 74(3):326-334.

Schaffer, MR, et al.: Diabetes-impaired healing and reducded wound nitric oxide synthesis: a possible pathophysiologic correlation. *Surgery* (1997) 121(5):513-519.

Schaffer, MR: et al.: Nitric oxide, an autocrine regulator of wound fibroblast synthetic function. *J Immunol* (1997) 158:2375-2381.

Schwarzer, U, et al.: The prevalence of Peyronie's disease: results of a large survey. *BJU Int* (2001) 88(7):727-730.

Sebkhl A, et al.: Phosphodiesterase type 5 as a target for the treatment of hypoxia-induced pulmonary hypertension. Circulation (2003) 107:3230-3235.

Sherratt, JA, et al.: Theoretical models of wound healing: past successes and future challenges. *C R Biol* (2002) 325(5):557-564.

Shimizu, E, et al.: OPC-13013, a cyclic nucleotide phosphodiesterase type III, inhibitors, inhibits cell proliferation and transdifferentiation of cultured rat hepatic stellate cells. Life Sci. (1999) 64(23):2081-2088.

Simko, F, et al.: The potential role of nitric oxide in the hypertropic growth of the left ventricle. Physiol. Res. (2000) 49:37-46.

Singer, AJ, et al.: Cutaneous wound healing. *N Engl J Med* (1999) 341(1):738-746.

Sinnaeve, P, et al.: Overexpression of a constitutively active protein kinase G mutant reduces neointima formation and in-stent restenosis. *Circulation* (2002) 105(24):2911-2916.

Sirotkin, AV, et al.: Effect of cGMP analogues and protein kinase G blocker on secretory activity, apoptosis and and the cAMP/protein kinase A system in procine ovarian granulose cells in vitro. *J Steroid Biochem Mol Biol* (2000) 74(1-2):1-9.

Smith, PG, et al.: Impaired cutaneous would healing after sensory denervation in developing rats: effects on cell proliferation and apoptosis. Cell Tissue Res. (2002) 307:281-291.

Smythe, GM, et al.: Immunobiology and the future of myoblast transfer therapy. *Mol Ther* (2000) 1(4): 304-313.

Somers, KD, et al.: Fibrin depositon in Peyronie's disease plaque. *J Urol* (1997) 157:311-315.

Somers, KD, et al.: Cell culture of Peyronie's disease plaque and normal penis tissue. *J Urology* (1982) 127:585-588.

Sosne, G, et al.: Thymosin beta 4 promotes corneal wound healing and decrease inflammation in vivo following alkali injury. *Exp Eye Res* (2002) 74(2): 293-299.

Souness, JE, et al.: Immunosuppressive and anti-inflammatory effects of cyclic AMP phosphodiesterase (PDE) type 4 inhibitors. Immunopharmacology (2000) 47:127-162.

Stausbol-Gron, B, et al.: Characterization and radiosensitivity of fibroblasts derived from squamous cell carcinomas of the head and neck, and the surrounding oral mucosa. *Acta Oncol* (1998) 37(7-8): 697-700.

Sullivan, ME, et al.: Vascular risk factors and erectile dysfunction. BJU Int. (2001) 87:838-845.

Susic, D, et al.: Prolonged L-arginine on cardiovascular mass and myocardial hemodynamics and collagen in aged spontaneously hypertensive rats and normal rats. Hypertension (1999) 33[part II]:451-455.

Taimor, G, et al.: Apoptosis induction by nitric oxide in adult cardiomyocytes via cGMP-signaling and its impairment after simulated ischemia. *Cardiovasc Res* (2000) 45(3):588-594.

Takemoto, M, et al.: Chronic angiotensin-converting enzyme inhibition and angiotensin II type 1 receptor blockade: effects on cardiovascular remodeling in rats induced by the long-term blockade of nitric oxide synthesis. *Hypertension* (1997) 30(6):1621-7.

Takuma, K, et al.: Ibudilast attenuates astrocyte apoptosis via cyclic GMP signalling pathway in an in vitro reperfusion model. *Br J Pharmacol* (2001) 133(6):841-848.

Tanaka, H, et al.: Involvement of bone morphogenic protein-2 (BMP-2) in the pathological ossification process of the spinal ligament. *Rheumatology* (Oxford) (2001) 40(10):1163-8.

Tanaka, H, et al.: Effect of IGF-I and PDGF administered in vivo on the expression of osteoblast-related genes in old rats. *J Endocrinol* (2002) 174(1):63-70.

Tao, J, et al.: Biological effects of C-type natriuretic peptide in human myofibroblastic hepatic stellate cells. *J Biol Chem* (1999) 274(34):23761-9.

Tarcin, O, et al.: In vivo inefficiency of pentoxifylline and interferon-alpha on hepatic fibrosis in biliary-obstructed rats: assessment by tissue collagen content and prolidase activity. J Gastroenterol Hepatol (2003) 18:437-444.

Tharaux, PL, et al.: Vascular endothelin-1 gene expression and synthesis and effect on renal type I collagen synthesis and nephroangiosclerosis during nitric oxide syntahse inhibition in rats. *Circulation* (1999) 99(16):2185-91.

Tharaux, PL, et al.: Angiotensin II activates collagen I gene through a mechanism involving the MAP/ER kinase pathway. *Hypertension* (2000) 36(3):330-336.

Thirunavukkarasu, K, et al.: Analysis of regulator of G-protein signaling-2 (RGS-2) expression and function in osteoblastic cells. J Cell Biochem (2002) 85(4): 837-850.

Thompson, WJ, et al.: Exisulind induction of apoptosis involves guanosine 3',5'-cyclic monophosphate phosphodiesterase inhibition, protein kinase G activation, and attenuated beta-catenin. *Cancer Res* (2000) 60(13):3338-3342.

Thornton, FJ, et al.: Enhanced collagen accumulation following direct transfection of the of the inducible nitric oxide synthase gene in cutaneous wounds. *Biochem Biophys Res Commun* (1998) 246:654-659.

Tian, B, et al.: Mechanisms of cytokine induced NO-mediated cardiac fibroblast apoptosis. Am. J. Physiol. (2002) 283:H1958-H1967.

Tiggelman, AM, et al.: Transforming growth factor-beta-induced collagen synthesis by human liver myofibrolasts in inhibited by alpha2-macroglobulin. *J Hepatology* (1997) 26:1220-1228.

Turko, IV, et al.: Inhibition of cyclic GMP-binding cyclic GMP-specific phosphodiesterase (Type 5) by sildenafil and related compounds. Mol. Pharmacol. (1999) 56:124-130.

Uckert, S, et al.: Phosphodiesterase isoenzymes as pharmocological targets in the treatment of male erectile dysfunction. *World J Urol* (2001) 19(1):14-22.

Usui, M, et al.: Pathogenic role of oxidative stress in vascular angiotensin-converting enzyme activation in long-term blockade of nitric oxide synthesis in rats. Hypertension. (1999) 34:546-551.

Van De Water, L: Mechanisms by which fibrin and fibronectin appear in healing wounds: implications for Peyronie's disease. *J Urol* (1997) 157:306-10.

Van Der Loo, B, et al.: Enhanced peroxynitrite formation is associated with vascular aging. J Exp Med. 2000; 192(12):1731-1743.

Vernet, D, et al.: Spontaneous expression of inducible nitric oxide synthase (iNOS) in the hypothalamus and other brain regions in aging rats. *Endocrinology* (1998) 139:3254-3261.

Vernet, D, et al: Effect of nitric oxide on fibroblast differentiation into myofibroblasts in cell cultures from the Peyronie's fibrotic plaque and in its rat model in vivo. Nitric Oxide. (2002) 7:262-276.

Wahl, SM: Inflammation and growth factor *J Urol* (1997) 157:303-305.

Walker, GA, et al.: Myofibroblasts: molecular crossdressers. *Curr Top Dev Biol* (2001) 51:91-107.

Wang, C, et al.: Male reproductive ageing: using the brown Norway rat as a model for man. *Novartis Found Symp* (2002) 242:82-95.

Wang, B, et al.: Regression of atherosclerosis: role of nitric oxide and apoptosis. Circulation (1999) 99:1236-1241.

Wang, P, et al.: Characterization of human, dog and rabbit corpus cavernosum type 5 phosphodiesterases. Life Sci. (2001) 68:1977-1987.

Wang, Y, et al.: Mechanisms of hepatoprotection by nitric oxide. Ann. N. Y. Acad. Sci. (2002) 962:415-422.

Watanabe, T, et al.: Dynamic change of cells expressing MMP-2 mRNA and MT1-MMP mRNA in the recovery from liver fibrosis in the rat. *J Hepatol*. (2001) 35(4): 465-473.

Westenfeld, R, et al.: Selective inhibition of inducible nitric oxide synthase enhances intraglomerular coagulation in chronic anti-Thy 1 nephritis. *Kidney Int* (2002) 61(3):834-838.

Windmeier, C, et al.: Pharmacological aspects of pentoxifylline with emphasis on its inhibitory actions on hepatic fibrogenesis. Gen Pharmacol (1997) 29(2):181-196.

Wollert, KC, et al.: Gene transfer of cGMP-dependent protein kinase I enhances the antihypertrophic effects of nitric oxide in cardiomyocytes. *Hypertension* (2002) 39(1):87-92.

Wu, J, et al.: Hepatic stellate cells: a target for the treatment of liver fibrosis. *J Gastroenterol* (2000) 35(9):665-672.

Yamasaki, K, et al.: Reversal of impaired wound repair in iNOS-deficient mice by topical adenoviral-mediated iNOS gene transfer. *Am J Physiol* (1998) 101(5):967-971.

Zhang, HY, et al.: Inhibition of myofibroblast apoptosis by transforming growth factor beta(1). *Am J Respir Cell Mol Biol* (1999) 21(6):658-665.

Zuk, PA, et al.: Multilineage cells from human adipose tissue: implications for cell-based therapies. *Tissue Engineering* (2001) 7(2): 211-228.

Duncan, M.R., "Connective tissue growth factor mediates transforming growth factor β-induced collagen synthesis: down-regulation by cAMP," FASEB Journal, vol. 13, (Oct. 1999) pp. 1774-1786.

Fuchs, et al., "Anatomy of penile venous drainage in potent and impotent men during cavernosography", J Urol., 141(6), (Jun. 1989), 1353-1356 (Abstract).

Herrmann, H C., et al., "Hemodynamic Effect of Sildenafil in Men with Severe Coronary Artery Disease", The New England Journal of Medicine, vol. 342, (Jun. 2000), 1622-1626.

Petrou, et al., "Management of corporal veno-occlusive dysfunction", Urol Int., 49(1), (1992), 48-55 (Abstract).

Pickard, et al., "Corpus cavernosal relaxation in impotent men", Br. J Urol., 74(4), (Oct. 1994), 485-491 (Abstract).

Rajfer, et al., "Prevalence of corporeal venous leakage in impotent men", J Urol., 140(1), (Jul. 1988), 69-71 (Abstract).

Shabsigh, et al., "Venous leaks: anatomical and physiological observations", J Urol., 146(5), (Nov. 1991), 1260-1265 (Abstract).

Babal, P., et al., "Chronic inhibition of NO synthesis produces myocardial fibrosis and arterial media hyperplasia," Histop Histopath (1997) 12:623-629.

Bosch, P., et al., "Osteoprogenitor cells within skeletal muscle," J Orthop Res. (2000) 18(6):933-944.

Breithaupt-Grogler, K., et al., "Epidemiology of the arterial stiffness," Pathol Biol (1999) 47:604-613.

Cheng, JW, et al., "L-Arginine in the management of cardiovascular diseases," Ann Pharmacother (2001) 35:755-764.

Freireich, et al., "Quantitative comparison of toxicity of anticancer agents in mouse, rat, hamster, dog, monkey and man," Cancer Chemotherapy Reports (1966) 50(4):219-244.

Gabbiani, G., "The cellular derivation and the life span of the myobibroblast," Path. Res. Pract. (1996) 192:708-711.

Gonca, S, et al., "Protective effects of vitamin E and selenium on the renal morphology in rats fed high-cholesterol diets," Pathobiology (2000) 68:258-263.

Jiaan, DB, et al., "Age-related increase in an advanced glycation end product in penile tissue," World J Urol (1995) 13:369-375.

Lee, GT, et al., "Expression of matrix metalloproteinases, in spontaneous regression in liver fibrosis," Hepato-Gastroenterology (2001) 48:1115-1117.

Martinez-Hernandez, A., "Repair, regeneration, and fibrosis," Pathology, 2nd ed., Chapter 3, pp. 77-103, JB Lippincott Ed, PA.

McCrudden, R., et al., "Liver fibrosis, the hepatic stellate cell and tissue inhibitors of metalloproteinases," Histol Histopathol (2000) 15(4):1159-1168.

Mignatti, P, et al., "Proteinases and tissue remodeling," The Molecular and Cellular Biology of Wound Repair, 2nd ed. (1996) Chapter 14, pp. 427-474.

Muralidhar, S., et al., "An ultrasonographic study of Peyronie's disease," Australasian Radiology (1996) 40(2):106-108.

Madtes, DK, et al., "Selective induction of tissue inhibitor of metalloproteinases-1 in bleomycin-induced pulmonary fibrosis," Am. J. Respir. Cell Mol. Biol. (2001) 24(5):599-607.

Sasaki, K, et al., "Nitric oxide mediates interleukin-1 induced gene expression of matrix metalloproteinases and basic fibroblast growth factor in cultured rabbit articular chondrocytes," Japanese Biochemical Society (1998) 123(3):431-439.

Sikka, WJ, et al., "Role of oxidative stress and antioxidants in peyronie's disease," Int. Journal of Impot. Res. (2002) 14:353-360.

Song, L, et al, "The protective action of taurine and L-Arginine in radiation pulmonary fibrosis," Journal of Environ. Path., Toxicol. and Ocol. (1998) 17(2):151-157.

Tomasek, JJ, et al., "Cellular structure and biology of dupuytren's disease," Hand Clinics (1999) 15(1):21-34.

Tomasek, JJ, et al., "Myofibroblasts and mechano-regulation of connective tissue remodelling," Nature Reviews Molecular Cell Biology (2002) 3:349-363.

Van Der Zee, E, et al., "Cytokines modulate routes of collagen breakdown," J Clin Periodontol (1997) 24(5):297-305.

Wang, Y, et al., "Mechanisms of hepatoprotection by nitric oxide," Ann. N.Y. Acad. Sci. (2002) 962:415-422.

Watanabe, S, et al., "Nuclear-factor Kappa B (NF-kB)-inducible nitric oxide synthase (iNOS/NOS II) pathway damages the stria vascularis in cisplatin-treated mice," (2002)22:4081-4086.

Yaguchi, T, et al., "Immunohistochemical and gelatin zymography studies for matrix metalloproteinases in bleomycin-induced pulmonary fibrosis," Pathol. Int. (1998) 48(12):954-963.

* cited by examiner

30 ug plasmid βGAL

10⁷ ADV-βGAL

PENILE DORSAL ARTERY

METHODS OF USE OF INHIBITORS OF PHOSPHODIESTERASES AND MODULATORS OF NITRIC OXIDE, REACTIVE OXYGEN SPECIES, AND METALLOPROTEINASES IN THE TREATMENT OF PEYRONIE'S DISEASE, ARTERIOSCLEROSIS AND OTHER FIBROTIC DISEASES

RELATED APPLICATIONS

The present application claims the benefit under 35 U.S.C. §119(e) of U.S. Provisional Application No. 60/420,281, filed on Oct. 22, 2002, and claims the benefit of PCT Application No. US03/33400, filed on Oct. 21, 2003.

BACKGROUND OF THE INVENTION

1. Field

The present methods and compositions relate to the field of Peyronie's disease, arteriosclerosis and other fibrotic conditions. More particularly, the method and compositions concern use of phosphodiesterase (PDE) inhibitors and modulators of nitric oxide, reactive oxygen species and metalloproteinases in the treatment of such conditions. In particular embodiments, the inhibitors inhibit type 4 and/or type 5 PDEs.

2. Description of Related Art

Peyronie's disease (PD) is a fibromatosis (Hellstrom and Bivalacqua, 2000; Schwarzer et al., 2001; Jarow et al., 1997; Devine et al., 1997) of the tunica albuginea (TA), the specialized lining of the corpora cavernosa of the penis. Clinically, this usually leads to penile deformation (curved penis during erection), pain, and quite frequently erectile dysfunction. The initiating event is believed to be an external force to the erect penis that results in an injury to the TA of the corpora and the TA fails to heal normally (Jarow et al., 1997; Devine et al., 1997; Diegelmann, 1997; Sherratt and Dallon, 2002). In the detumesced state, the only indication of the disease is the palpation of a knot or scar within the TA, which in its most severe state presents as a calcified plaque.

PD affects about 5% of men in the USA, and translating into about 3-4 million affected American males. Although the condition is not always associated with erectile dysfunction, patients usually present to the physician with either recognition of a palpable plaque on the penile shaft, pain with tumescence, impotence and/or difficulty with intromission that is due to curvature of the erect penis. Since the disorder was first described in 1743, no medical treatment has ever proven to be beneficial in combating the condition, thereby highlighting the need to develop novel approaches to combat this disorder.

There may also be a genetic predisposition to developing PD, since it is associated with other contractures such as Dupuytren's disease (palmar fascia; 10-20% incidence or more in PD) (Connelly, 1999) and Ledeshore's disease (plantar fascia). The pathophysiology is characterized by localized disruption of the TA, increased microvascular permeability, persistent fibrin (deficient fibrinolysis) and collagen deposition, perivascular inflammation, disorganization and loss of elastic fibers (release of elastase by macrophages), disorganized collagen bundles, and an increase in TGF-β1 synthesis. This represents impairment in the repair process that leads to persistent fibrosis and a loss of elasticity of the TA.

PD can rarely be alleviated by medical treatment with anti-inflammatory agents (corticosteroids, antihistamine), antioxidants (vitamin E, superoxide dismutase), collagen breakdown (collagenase), Ca channel blockers (verapamil), and other antifibrotic compounds (colchicine, Potaba: K aminobenzoate) (Hellstrom and Bivalacqua, 2000). In most cases, surgery is the only available option to correct the deformity and alleviate the pain so that normal sexual activity can be resumed. A need exists for non-surgical methods of treatment of Peyronie's disease and other medical conditions in which fibrosis is important.

Fibrotic disease is not limited to the reproductive organs, but can be found in other tissues, such as cardiovascular tissues. Both erectile dysfunction (ED) and cardiovascular disease, particularly hypertension, are prevalent in the aging male (Kloner et al., 2002; Sullivan et al., 2001; Melman et al., 1999). One of the underlying causes of hypertension is arteriosclerosis, or arterial stiffness, due to an acquired fibrosis of the media of the arterial wall (Breithaupt-Grogler and Belz, 1999; Robert, 1999; Intengan and Schiffrin, 2000, 2001; Formieri et al., 1992). Arteriosclerosis is significantly associated with aging, and is recognized by an increase in collagen, and in some cases by a loss of smooth muscle cells (SMC) within the arterial media, which results in a decrease in the SMC/collagen ratio, often accompanied by endothelial dysfunction (Cai and Harrison, 2000).

The pathogenesis of aging associated ED, both in the human and rat, is mostly related to the loss of SMC in the penile corpora cavernosa by apoptosis, with a corresponding increase in collagen fibers (Melman and Gingell, 1999; Cai and Harrison, 2000; Melman, 2001; Garban et al., 1995; Ferrini et al., 2001a). The clinical result of this aging process in the penis is defective cavernosal SMC relaxation leading to veno-occlusive dysfunction (Breithaupt-Grogler and Belz, 1999; Rogers et al., 2003), the most common cause of ED.

In the arterial tree, excessive collagen deposition in the media, with or without loss of SMC, leads to defective vasorelaxation and clinically may present as hypertension (Breithaupt-Grogler and Belz, 1999; Robert, 1999; Intengan and Schiffrin, 2000, 2001). Because the penis may be considered a specialized extension of the vascular tree, the common alterations observed in the SMC of both the penis and peripheral vascular system in the aging male, leading to ED and hypertension, respectively, suggest that both conditions may share a common etiology.

A need exists for effective methods to treat and/or ameliorate the symptoms of a variety of fibrotic disease, such as PD, ED and arteriosclerosis. No effective method of treatment currently exists that is directed towards the molecular pathways underlying excessive collagen deposition.

SUMMARY OF THE INVENTION

Certain embodiments of the present invention fulfill an unresolved need in the art, by providing novel methods for therapeutic treatment of Peyronie's disease, erectile dysfunction, arteriosclerosis and other fibroses. In some embodiments, PD plaques and/or other fibrotic conditions can be pharmacologically arrested or reduced in size, by decreasing collagen synthesis and inducing myofibroblast apoptosis by increasing the NO/ROS ratio, the levels of cGMP, or the activation of its effector, PKG in the TA and/or stimulating collagen degradation by activating the MMPs and/or down-regulating the expression of the MMP inhibitors (TIMP), by increasing NO/cGMP levels and/or the thymosins in the TA.

Particular embodiments of the invention may be directed towards increasing levels of cGMP and/or cAMP by selective inhibition of phosphodiesterase (PDE) isoforms. PDE isoforms of interest in the TA and in PD plaque tissues include PDE5A-3, PDE4A, PDE4B and PDE4D. As non-limiting examples, pentoxifylline and similar compounds act as a non-specific cAMP-PDE inhibitor and increase cAMP levels, while sildenafil and similar compounds selectively inhibit PDE5A and increase cGMP levels.

Other embodiments may involve increasing NO levels, for example by administering L-arginine, a stimulator of NOS activity. As shown in the following examples, pentoxifylline, sildenafil and L-arginine all act to reduce the expression of collagen I and α-smooth muscle actin. Long-term administration of nitrergic agents, such as pentoxifylline, sildenafil and L-arginine may be of use to reduce PD plaque size and collagen/fibroblast ratio and may reverse or prevent the further development of the fibrosis observed in PD, ED, arteriosclerosis and other fibrotic conditions.

BRIEF DESCRIPTION OF THE DRAWINGS

The following drawings form part of the present specification and are included to further demonstrate certain embodiments of the claimed subject matter. The embodiments may be better understood by reference to one or more of these drawings in combination with the detailed description presented herein.

Figure 1:
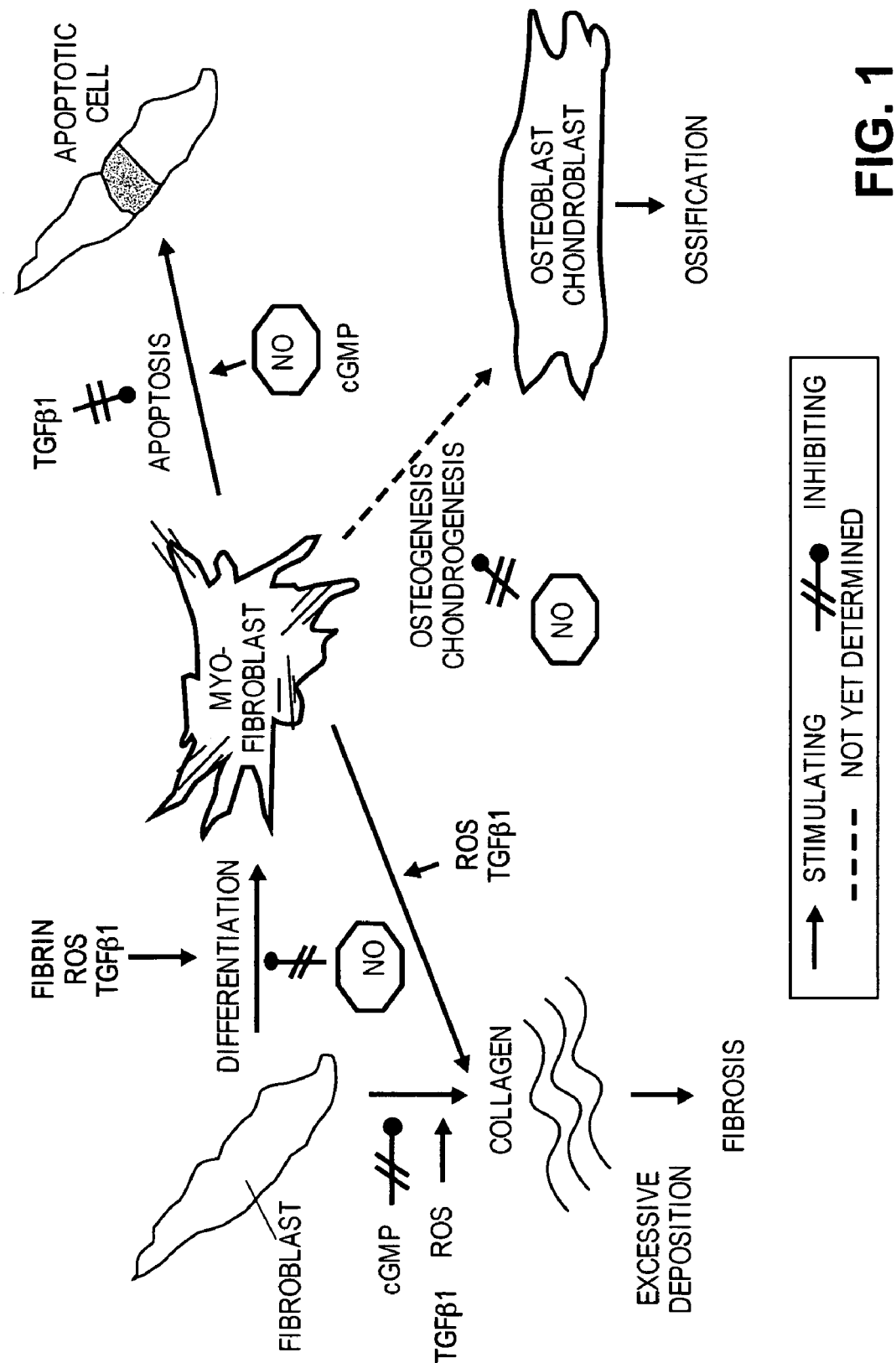
FIG. 1. The effect of NO, TGF-β1, ROS and cGMP on fibroblast/myoblast differentiation and collagen deposition.

Table 1. Differential profiles of selected gene expression in human Peyronie's plaques and Dupuytren's nodules against their respective control tissues determined with a DNA microarray assay.

Table 2. Effect of aging on arterial wall thickness and lumen diameter in large and small arteries in the rat n=5; **: $p<0.01$.

DETAILED DESCRIPTION OF ILLUSTRATIVE EMBODIMENTS

Abbreviations and Definitions

The following abbreviations are used herein. Other abbreviations not listed below have their plain and ordinary meaning.

ASMA: α-smooth muscle actin;
ED: erectile dysfunction;
iNOS: inducible NOS (also NOS II);
L-NAME: L-$N_\omega$-Nitro-L-arginine methyl esther;
L-NIL: L-iminoethyl-L-lysine;
MMP: matrix metalloproteinase;
nNOS: neuronal NOS;
NO: nitric oxide;
NOS: nitric oxide synthase;
PAI: plasminogen activator inhibitor;
PD: Peyronie's disease;
PDE: phosphodiesterase;
PKG: protein kinase G;
PPC: pluripotent cells;
QIA: quantitative image analysis;
ROS: reactive oxygen species;
SMC: smooth muscle cell;
SNAP: S-Nitroso-N-acetyl penicillamine;
TA: tunica albuginea;
TGF-β1: transforming growth factor-β1;
TIMP: tissue inhibitor of MMP.

As used herein, "a" or "an" may mean one or more than one of an item.

This application concerns, at least in part, isolated proteins and nucleic acids for type 5 phosphodiesterase (PDE5, e.g., GenBank Accession Nos. NM033437, NM033431, NM033430, NM001083, NP246273, NP237223, NP236914, NP001074), as well as methods of therapeutic treatment of fibrotic diseases directed towards such proteins. In the present disclosure, reference to "PDE5" or "type 5 phosphodiesterase" without further qualification or limitation means any or all isoforms of PDE5.

A "PDE5 isoform" is a variant of type 5 phosphodiesterase that differs in its primary structure (i.e., amino acid sequence) from other isoforms of PDE5. The term encompasses, but is not limited to, isoforms that are produced by truncation, amino acid substitution (mutation) or by alternative mRNA splicing, so long as some difference in amino acid sequence results. For the purposes of the present invention, other types of covalent modification would be considered to fall within the scope of a single isoform. For example, both phosphorylated and unphosphorylated forms of PDE5 would be considered to represent the same isoform.

As used herein, an "inhibitor" of PDE5 means any compound or combination of compounds that acts to decrease the activity of PDE5, either directly or indirectly. An inhibitor can be a molecule, an atom, or a combination of molecules or atoms without limitation. The term "antagonist" of PDE5 is generally synonymous with an "inhibitor" of PDE5. Inhibitors may act directly on PDE5 by, for example, binding to and blocking the catalytic site or some other functional domain of PDE5 that is required for activity. An inhibitor may also act indirectly, for example, by facilitating or interfering with the binding of PDE5 to another protein or peptide.

This application also concerns, at least in part, isolated proteins and nucleic acids for type 4 phosphodiesterase (PDE4, e.g., GenBank Accession Nos. NM006203, NM002600, NM006202, NP006194, NP002591, NP006193), as well as methods of therapeutic treatment of fibrotic diseases directed towards such proteins. In the present disclosure, reference to "PDE4" or "type 4 phosphodiesterase" without further qualification or limitation means any or all isoforms of PDE4. The terms "PDE4 isoform" and PDE4 "inhibitor" or "antagonist" are used consistently with the corresponding terms defined above for PDE5.

Peyronie's Disease and Other Fibrotic Conditions

Peyronie's Disease

Peyronie's disease (PD) is a localized fibrosis of the tunica albuginea (TA) of the penis (Hellstrom and Bivalacqtia, 2000; Gonzalez-Cadavid et al., 2002; Gholami et al., 2002) affecting close to 5% of the male population (Schwarzer et al., 2001). The leading theory of the etiology of PD is that it results from an abnormal wound healing process of the TA subsequent to an injury, usually during coitus (Hellstrom and Bivalacqua, 2000; Gonzalez-Cadavid et al., 2002; Gholami et al., 2002; Jarow and Lowe, 1997; Devine et al., 1997). It is assumed that at the time of the injury, extravasation of blood borne proteins, mainly fibrin, into the TA occurs (Somers and Dawson, 1997; Van de Water, 1997; Herrick et al., 1999). Some of these foreign proteins may induce a severe but local inflammatory response in the TA resulting in the local release of pro-fibrotic factors, mainly transforming growth factor β1 (TGF-β1) and reactive oxygen species (ROS) (Hellstrom and Bivalacqua, 2000; Gonzalez-Cadavid et al., 2002; Gholami et al., 2002), which then trigger excessive deposition and disorganization of the collagen fibers.

Within the injured TA of some individuals, the above process may result in: a) an increase in the differentiation of TA fibroblasts into myofibroblasts (Vernet et al., 2002); b) an increased deposition of collagen fibers by both the TA fibroblasts and myofibroblasts (Vernet et al., 2002; Ferrini et al., 2002); c) a decrease in apoptosis of the TA fibroblasts/myofibroblasts, and d) a decrease in the natural breakdown and reorganization of newly deposited collagen fibers that is normally performed by the matrix metalloproteinases (MMP) (Mignatti et al., 1996; Arthur, 2000). The MMPs are the collagenolytic enzymes that are involved in the natural turnover of collagen in the wound healing process. At its extreme, this process may become excessive, with newly deposited collagen and extracellular matrix in a tissue that fails to "heal and reorganize normally" (Mignatti et al., 1996) eventually becoming calcified (Gelbard, 1988; Muralidhar et al., 1996). Calcification may occur by osteoblasts that are transformed from pluripotent cells (PPC) among the fibroblasts and/or myofibroblasts within the TA by either autocrine and/or paracrine factor(s).

The primary cell that is involved in collagen synthesis in the wound healing process is the fibroblast (Singer and Clark, 1999). For wound closure, some of the fibroblasts must differentiate into myofibroblasts (Vernet et al., 2002; Gonzalez-Cadavid et al., 2002; Gholami et al., 2002; Muralidhar et al., 1996; Singer and Clark, 1999, Powel et al., 1999), cells that are intimately involved in the terminal stages of the wound healing process. Once this process is completed, the myofibroblast is normally eliminated from the wound by apoptosis (Gabbiani, 1996). If myofibroblasts persist and do not undergo pre-programmed cell death, they may continue to synthesize additional collagen and extracellular matrix, leading to an increase in fibrosis. Within the TA, this increase in fibrosis may lead to the clinical recognition of a palpable Peyronie's plaque.

In addition to being a stimulator of the differentiation of fibroblasts into myofibroblasts, TGF-β1 can be secreted by both fibroblasts and myofibroblasts (Powel et al., 1999; Tomasek et al., 1999; Walker et al., 2001). In other fibrotic conditions, like cardiac and renal fibrosis, TGF-β1 has been shown to not only increase the replication and differentiation of fibroblasts into myofibroblasts, but also to inhibit apoptosis of the myofibroblasts (Desmouliere, 1995; Chipev et al., 2000). This self-perpetuating cycle of cellular differentiation of fibroblasts into myofibroblasts and continued TGF-β1 secretion by these same two cell types, as a result of the exposure of these cells to TGF-β1 itself, may ultimately lead to excessive collagen synthesis. Coupled with a disorganization of collagen fibers and a decrease in their degradation by at least a partial inhibition of the MMPs (Iredale, 1997), this may explain the continued growth of the PD plaque.

In response to the pro-fibrotic effects of TGF-β1 and ROS in the TA, the injured TA tissue attempts to counteract these pro-fibrotic processes by releasing the anti-fibrotic compound, nitric oxide (NO). NO in the TA is synthesized by the inducible nitric oxide synthase enzyme (iNOS) (Vernet et al., 2002; Gonzalez-Cadavid et al., 2002; Gholami et al., 2002; Ferrini et al., 2002). Therefore, in the development of PD, there may be a constant battle between pro-fibrotic and anti-fibrotic processes within the TA, as is evident from the results from DNA microarrays discussed in the Examples below, with the winner determining whether normal healing or a fibrotic condition ensues.

As discussed in the Examples below, studies on the corresponding human tissues and cells combined with data from rat models have shown that the development of the PD plaque is associated with expression of inducible nitric oxide synthase (INOS) and stimulation of nitric oxide (NO) synthesis, in conjunction with an increase in oxidative stress and ROS levels (Vernet et al., 2002; Gholami et al., 2002; Hellstrom and Bivalacqua, 2000; Sikka et al., 2002). The specific inhibition of iNOS activity with L-iminoethyl-L-lysine (L-NIL) exacerbates fibrosis in the TGF-β1 rat model, consistent with a model wherein NO produced by iNOS plays an antifibrotic role in PD by at least three mechanisms: a) the quenching of the pro-fibrotic ROS by a reaction leading to the formation of peroxynitrite; b) the down-regulation of fibroblast replication and myofibroblast differentiation; and c) the consequent or independent reduction in the transcriptional expression of collagen I.

An additional mechanism for NO to counteract fibrosis may involve stimulation of myofibroblast and/or fibroblast programmed cell death. The induction of apoptosis by NO is well documented, either in vitro by NO donors, such as S-Nitroso-N-acetyl penicillamine (SNAP) (Sikka et al., 2002; Nishio et al., 1996) or inducible nitric oxide synthase (iNOS) expression (Nishio et al., 1996; Tain et al., 2002), or in vivo by neuronal NOS (nNOS) activation (Ferrini et al., 2001b), iNOS induction (Ferrini et al., 2001b; Watanabe et al., 2002), or administration of the NOS substrate L-arginine (Wang et al., 1999; Holm et al., 2000). The proposed antifibrotic role of iNOS is in agreement with indirect results obtained in animal models of kidney and cardiac fibrosis, where general NOS inhibitors (not isoform-specific), such as L-N$_\omega$-Nitro-L-arginine methyl esther (L-NAME), cause or exacerbate fibrosis (Chatziantoniou et al., 1998; Boffa et al., 1999; Pechanova et al., 1999). L-arginine supplementation has been shown to be anti-fibrotic in vascular and renal disease (Peters et al., 2000), but has not been tested on the PD plaque.

Thus, pharmacologic inhibition of the pro-fibrotic process and/or stimulation of the anti-fibrotic processes, may halt the progression and/or reverse the process of PD. More globally, such results may be extrapolated to more life-threatening fibrotic conditions such as renal, lung, liver, and cardiac fibrosis (Nagase and Brew, 2002; Martinez-Hernández, 1994; Schuppan et al., 2000). The results disclosed herein provide novel avenues of therapy for not only PD but also for fibrosis in general.

The interaction within the TA between the pro-fibrotic and anti-fibrotic factors acting on fibroblasts and myofibroblasts and their respective differentiation and apoptotic processes is outlined in FIG. 1. One of the major functions of NO produced by iNOS in the PD tissue is to react with the pro-fibrotic compound ROS to form peroxynitrite (Beckmann and Koppenol, 1996; Ferrini et al., 2001a; Vernet et al., 1998). Peroxynitrite is known to induce apoptosis in most cell types, and specifically of the collagen-producing cells such as the fibroblast and myofibroblast (Heigold et al., 2002; Duffield et al., 2000; Zhang and Phan, 1999). In addition, NO stimulates guanylyl cyclase to produce cGMP Gonzalez-Cadavid et al., 1999), which in turn stimulates PKG (protein kinase G) (Sinnaeve et al., 2002; Wollert et al., 2002). Like NO, both cGMP and PKG inhibit collagen synthesis and are anti-fibrotic (Sinnaeve et al., 2002; Wollert et al., 2002; Hofmann et al., 2000; Chen et al., 1999a, 1999b; Redondo et al., 1998). cGMP is normally degraded to inactive GMP by the phosphodiesterase (PDE) enzymes (Corbin and Francis, 1999; Uckert et al., 2001). Some of the inhibitors of these enzymes, like pentoxifylline, have also been shown to be anti-fibrotic in animal models and humans (Fischer et al., 2001; Desmouliere et al., 1999; Kremer et al., 1999).

The accumulation of collagen, which is one of the histological hallmarks of tissue fibrosis, may in part be also due to the inactivation of the MMP enzymes that degrade the already laid-down collagen fibers during its natural turnover cycle (Mignatti et al., 1996; Arthur, 2000). MMPs can be inactivated by TIMPs, the tissue inhibitors of MMP, that have been shown to increase in fibrotic conditions (Iredale, 1997; McCrudden and Iredale, 2000; Arthur, 2000). Another antifibrotic effect of NO is that it stimulates MMP activity (Sasaki et al., 1998; Okamoto et al., 1997) and inhibits the expression of TIMP (Darby et al., 2002; Bugno et al., 1999).

The results disclosed below provide a series of approaches (Magee et al., 2002b; Ferrini et al., 2002) focused on the role of the myofibroblast and the interaction between NO and ROS (the NO/ROS balance) in the pathogenesis of the PD plaque and in arteriosclerosis, particularly of penile arteries. These include the use of the established TGF-β1 rat model of PD (Ferrini et al., 2002; Vernet et al., 2002; Gonzalez-Cadavid et al., 2002; Gholami et al., 2002), the establishment and study of cell cultures from the human PD and normal TA tissues (Vernet et al., 2002; Gonzalez-Cadavid et al., 2002; Gholami et al., 2002), the application of quantitative image analysis (QIA) of tissue sections and cells subjected to histochemistry and immunohistochemistry (Ferrini et al., 2002; Vernet et al., 2002; Gonzalez-Cadavid et al., 2002; Gholami et al., 2002), the use of selective inhibitors of some of the biochemical pathways shown in FIG. 1 (Ferrini et al., 2002; Vernet et al., 2002; Gonzalez-Cadavid et al., 2002; Gholami et al., 2002), DNA microarrays for multiple gene expression (Magee et al., 2002b), the discovery that the same processes that occur in the PD fibrotic plaque are also involved in aging-related fibrosis of the arterial wall media leading to arteriosclerosis, which by affecting the penile arteries would cause ED, and other molecular biology assays that provide an integrated analysis of the molecular pathophysiology of this condition, with corresponding novel approaches to therapeutic intervention of fibrotic disease directed towards the underlying molecular pathways.

The combination of 1) an agent that increases NO, cGMP or cAMP levels, with 2) a compound that reduces oxidative stress and ROS levels, such as an antioxidant, will preserve the antifibrotic effects of agents in the first category, without an undesirable excessive level of apoptosis that may lead to cytotoxicity in cells other than myofibroblasts (e.g., smooth muscle cells, neurons, endothelial cells, etc.) By reducing ROS with the antioxidant, the formation of deleterious levels of peroxynitrite (the product of ROS quenching by NO) would be reduced to the minimum required for effective antifibrotic effects on myofibroblasts and fibroblasts involved in excessive collagen and extracellular matrix synthesis, without damage to other tissues. In the case of the combination of an antioxidant with agents in the first category raising cGMP or cAMP levels, the reduction in ROS would allow more endogenous NO levels to be preserved. Therefore, the combination of agents may be more effective and safe than a single agent in either category alone.

The skilled artisan will realize that the methods and compositions disclosed herein are of use not only for treatment of Peyronie's disease and ED due to loss of cavernosal smooth muscle in the trabecular spaces and penile arteries, but also for other conditions involving fibrosis, such as penile corporal fibrosis, Dupuytren's disease nodules, vaginal fibrosis, clitoral fibrosis, female sexual arousal disorder, abnormal wound healing, keloid formation, general fibrosis of the kidney, bladder, prostate, skin, liver, lung, heart, intestines or any other localized or generalized fibrotic condition, vascular fibrosis, arterial intima hyperplasia, atherosclerosis, arteriosclerosis, restenosis, cardiac hypertrophy or any other condition characterized by excessive fibroblast or smooth muscle cell proliferation or deposition of collagen and extracellular matrix in the blood vessels and/or heart. Both the vagina and clitoris are known to undergo fibrosis and hardening with aging, menopause and estrogen/testosterone deficiency. Together with poor lubrication, the vaginal/clitoral fibrosis contribute to the development of female sexual arousal disorder, affecting about 30 to 40% of women. (Traish et al., Arch. Sex Behav. 31:393-400, 2002; Park et al., Intl. J. Impot. Res. 13:116-124, 2001; Berman et al., J. Sex Marital Ther. 27:411-420, 2001; Berman et al., Urology 54:385-391, 1999; Berman et al., Fertil. Steril., 79:925-931, 2003.) The mechanisms of fibrosis are similar for a number of different organs and disease states.

A distinction exists between long-term (weeks, months, years) continuous treatment with, for example, a PDE5 inhibitor such as sildenafil to maintain a constant level of these agents in order to arrest or regress a fibrotic condition, versus on demand (prior to the sexual act) single pill, short-term treatment with sildenafil or other PDE5 inhibitors to obtain smooth muscle vasodilation in the penis (male penile erection) or vagina/clitoris (female sexual arousal) upon sexual stimulation. Current studies with sildenafil are symptomatic to treat defects in vaginal/clitoral or penile vasodilation exclusively during a sexual act and are not addressed to the long-term cure of underlying tissue fibrosis. Additional details relevant to the treatment of fibrotic conditions are disclosed in the Examples section below as well as in the references of Vernet et al. (2002), Gonzalez-Cadavid et al. (2002) and Gholami et al. (2002), the entire texts of which are specifically incorporated herein by reference.

Peripheral Vascular Disease, Erectile Disfunction and Hypertension

One of the prevalent views of peripheral vascular disease is that it is caused by oxidative damage to the arterial wall by reactive oxygen species (ROS), that cause lipid peroxidation and other alterations (Cai and Harrison, 2000; Berry et al., 2001; Zalba et al., 2000). These compounds are mainly produced by xanthine oxidase, NADPH oxidase, as well as mitochondrial enzymes, and are counteracted by heme-oxygenase I and superoxide dismutase (SOD), which can reduce ROS by acting as endogenous antioxidants. In addition to causing endothelial damage, ROS are known stimulators of collagen deposition and SMC proliferation (Berry et al., 2001; Zalba et al., 2000) in the vascular wall. Xanthine oxidase and SOD are also present in the penile corpora cavernosa (Jones et al., 2002), and oxidative stress due to ROS has been postulated to be central to impaired cavernosal function in aging-related ED (Jones et al., 2002; Khan et al., 2001; Bivalacqua et al., 2003).

Besides antioxidants, nitric oxide (NO) also quenches ROS in the vasculature, as shown by the increase in ROS levels and the development of cardiac and renal fibrosis and vascular stiffness when there is long-term systemic blockade of NOS activity with NOS inhibitors (Kitamoto et al., 2000; Gonzalez et al, 2000; Usui et al., 1999). The ROS-quenching and anti-fibrotic effects of NO are not limited to the SMC and can be demonstrated in other non-vascular conditions (Ferrini et al., 2002; Vernet et al., 2002). In this process, NO reduces ROS levels through the formation of peroxynitrite (Cai and Harrison, 2000; Jones et al., 2002; Ferrini et al., 2002; Vernet et al., 2002; Gewaltig and Kojda, 2002), thereby increasing the NO/ROS ratio. NO is also postulated to not only inhibit collagen synthesis directly, but to favor collagen degradation by stimulating metalloproteinases and down-regulating expression of their inhibitors, such as the plasminogen activator inhibitor (PAI) (Li et al., 2000; Kaikita et al., 2002). The predominance of nitrosative pathways over oxidative stress is proposed to be protective against fibrosis (Ferrini et al., 2002; Vernet et al., 2002), ED (Jones et al., 2002), atherosclerosis, and hypertension (Gewaltig and Kojda, 2002; Cheng et al., 2001).

The NO/ROS balance also directly modulates the relaxation of the vascular and penile smooth muscle. The NO produced by the endothelial NOS in the vascular endothelium controls blood pressure by relaxing the arterial SMC (González-Cadavid et al., 1999). In the penile corpora cavernosa, NO as a mediator of penile erection is produced by the neuronal NOS, specifically the PnNOS variant (Berry et al., 2001), localized in the nerve terminals, and to a lesser extent by endothelial NOS in the lacunar and sinusoidal endothelium of the penis (González-Cadavid et al., 1999). In experimental animals, reduction in NOS levels in the vasculature and penile corpora is associated with hypertension (Gewaltig et al., 2002) and with ED, respectively (González-Cadavid et al., 1999; Garban et al., 1995; Berry et al., 2001). If oxidative stress becomes excessive, the reaction of ROS with NO to form peroxynitrite reduces NO concentration in the tissues, which may lead to hypertension and ED by impairing NO dependent SMC relaxation.

It is still unknown to what extent these neuronal and endothelial NOS isoforms participate in producing NO as an anti-fibrotic mechanism. In contrast, more direct evidence has emerged recently on the role of the inducible isoform of NOS (iNOS) (Kibbe et al., 1999) in reducing ROS and modulating the SMC/collagen ratio in different tissues. iNOS is spontaneously induced in the corpora cavernosa (Ferrini et al., 2001a) and brain (Vernet et al., 1998; Ferrini et al., 2001b) during aging, and in certain fibrotic conditions (Ferrini et al., 2002; Vernet et al., 2002). In the vasculature, iNOS is also induced in the media in aging-related arterial stiffness (Goettsch et al., 2001; Chou et al., 1998; Cernadas et al., 1998), transplant arteriosclerosis (Lee et al., 1999), and atherosclerosis (Ihrig et al., 2001; Niu et al., 2001; Behr-Roussel et al., 2000), and it is assumed to inhibit collagen deposition and prevent medial hyperplasia via induction of SMC apoptosis and/or inhibition of SMC replication (Gewaltig and Kojda, 2002; Kibbe et al., 1999; Niu et al., 2001). The specific inhibition of iNOS activity by L-N-(iminoethyl)-lysine acetate (L-NIL) (Ferrini et al., 2002; Vernet et al., 2002; Behr-Roussel et al., 2000), or the blockade of iNOS expression in the iNOS knockout mouse (Ihrig et al., 2001; Niu et al., 2001; Hochberg et al., 2000), causes fibrosis in non-vascular tissues, a decrease in NO/peroxynitrite levels, an increase in ROS, and a reduction in the SMC/collagen ratio.

Despite the fact that a certain predominance of the nitrosative over the oxidative pathways may preserve the normal integrity and function of blood vessels and corpora cavernosa, an excessive production of NO and peroxynitrite, may also induce apoptosis and cell loss (Ferrini et al., 2001a, 2002; Vernet et al., 2002; Kibbe et al., 1999). Depending on the context, this may be beneficial by preventing media hyperplasia in atherosclerosis and restenosis and ameliorate fibrosis in other systems (Ferrini et al., 2002; Vernet et al., 2002; Gewaltig et al., 2002; Behr-Roussel et al., 2000). But excessive peroxynitrite may also be noxious, if it leads to a loss of SMC and the subsequent impairment of tissue relaxation. We propose that during aging, iNOS induction in the vasculature is not restricted to the cavernosal SMC (Ferrini et al., 2001a) and large arteries (Goettsch et al., 2001; Chou et al., 1998; Cernadas et al., 1998), but is generalized to the wall of the entire peripheral vascular tree. This process would aim to counteract oxidative stress and metalloproteinase inhibition, and the subsequent decrease in the SMC/collagen ratio that causes loss of compliance and NO-induced vaso-relaxation. As disclosed in the following Examples, we have examined large and small (resistance) arteries in both young and aged rats for SMC/collagen ratio, iNOS, peroxynitrite, heme oxygenase I, SOD, PAI, and SMC apoptosis, and determined how these parameters were affected in aged rats when iNOS activity was specifically inhibited with L-NIL.

NO/cGMP Inhibition of Fibrogenic Pathways

In molecular terms, the fibrotic process occurring during abnormal wound healing, e.g., in dermal wounds, is essentially an increased and disorganized collagen deposition impairing granulation tissue formation. This is accompanied by an increase in the local production and secretion of TGF-β1 (Klar and Morrisey, 1998; Badalamente et al., 1996; Wahl, 1997), a factor which: a) stimulates collagen synthesis (Tiggelman et al., 1997; Faouzi et al., 1999), b) inhibits collagenolysis (van der Zee et al., 1997) and fibrinolysis (Holmdahl et al., 2001), c) enhances the release of ROS (Casini et al., 1997; Muriel, 1998a), and d) transcriptionally represses iNOS (Hung et al., 1995).

ROS are hydroxyl radicals and superoxide anions that are quenched by NO to primarily form peroxynitrite (Poli, 2000; Curtin et al., 2002; Cattell, 2002; Kim et al., 2001; Fan et al., 2000; Ito et al., 1992). The balance between NO and ROS levels is known to be considerably altered in other fibrotic conditions affecting liver (cirrhosis), lung (pulmonary fibrosis), kidney (renal fibrosis), heart (cardiac hypertrophy), and the vascular tree (arterial medial hyperplasia). This abnormal ratio between NO and ROS is believed to be due to both a decrease in local NO synthesis (presumably via iNOS) and an increase in ROS (Casini et al., 1997; Muriel, 1998a; Curtin et al., 2002; Cattell, 2002; Kim et al., 2001; Fan et al., 2000). ROS, produced by the macrophages and neutrophils, have been shown to induce lipid peroxidation in cell membranes and increase vascular permeability and leakage of fibrinogen and other clotting factors into tissue (Cattell, 2002; Kim et al., 2001). ROS generation during oxidative stress is accompanied by a considerable induction of heme-oxygenase-1 (HO-1) (Foresti et al., 1999; Nathan, 1997), the enzyme that protects against oxidative stress and acts as an anti-apoptotic and anti-inflammatory (Ryter and Choi, 2002) response. HO-1 can also be elicited by peroxynitrite.

Among the several regulators of collagen deposition and wound healing, NO is particularly interesting as an inhibitor of fibrosis. In the case of PD, NO appears to be produced by the induction of iNOS in the TA (Ferrini et al., 2002; Vernet et al., 2002; Gonzalez-Cadavid et al., 2002; Gholami et al., 2002). This iNOS isoform is involved in producing persistent high levels of NO by transcriptional induction, essentially as a defensive mechanism during inflammation (Nathan, 1997a, 1997b). iNOS is physiologically expressed in the adult at very low basal levels, if at all. Only upon induction by cytokines, such as tumor necrosis factor α (TNFα), interleukin 1β (IL-1β), interferon-γ (INFγ), and related factors, does iNOS induction take place. It can under certain chronic conditions lead to a high, and some times excessive production of NO that acts as either a cytotoxic agent, or, in the specific case of collagen, inhibits fiber deposition. These conditions include inflammation, infections, cancer, degenerative diseases and aging, where the factors triggering this increased iNOS response are unknown (Kibbe et al., 1999; Wang et al., 2002a; Miller and Sandoval, 1999). Additionally, many NO metabolites, particularly peroxynitrite, trigger localized apoptosis and tissue toxicity (Nathan, 1997a).

The specific role of NO as a regulator of wound healing is well established in vivo and in vitro (Curtin et al., 2002; Cattell, 2002; kim et al., 2001; Hogaboam et al., 1998; Rizvi and Myers, 1997; Cao et al., 1997; Chatziantoniou et al., 1998; Kolpakov et al., 1995). NO donors and the NOS substrate, L-arginine, have been shown to inhibit collagen fiber ((Curtin et al., 2002; Cattell, 2002; kim et al., 2001; Hogaboam et al., 1998; Rizvi and Myers, 1997; Cao et al., 1997; Chatziantoniou et al., 1998; Kolpakov et al., 1995) and fibrin deposition (Westenfeld et al., 2002; Dambisya and Lee, 1996; Catani et al., 1998; Dambisya et al., 1996), and TGF-β1 synthesis (Craven et al., 1997). The experimental decrease of NO synthesis by NOS inhibition, or the reduction of iNOS induction, leads to impaired wound healing (Schaffer et al., 1997a), and also to fibrosis, as documented in myocardial hypertrophy, coronary vascular remodeling following an infarct, cystic fibrosis, obstructive nephropathy, and pulmonary fibrosis (Takemoto et al., 1997; babal et al., 1997; Numaguchi et al., 1995; Ikeda et al., 1997; Moreno et al., 1996; Morrissey et al., 1996; Kelley and Drumm, 1998). Physiologically, the reduction of NO synthesis may occur by either transcriptional blockade of iNOS induction (Geller and Billiar, 1998; Forstermann et al., 1998), and in certain cases, down-regulation of eNOS (Forstermann et al., 1998), or by inhibition of NOS activity by advanced glycation-end products (AGE) (Jiaan et al., 1995) or a natural NOS competitive inhibitor such as asymmetric dimethyl arginine (ADMA) (Boger et al., 1998).

In contrast to the anti-fibrotic effect of NO that would occur as a defense against fibrosis, in the early stages of normal wound healing NO actually stimulates collagen synthesis (Schaffer et al., 1997b; Yamasaki et al., 1998; Thornton et al., 1998; Sherratt and Dallon, 2002; Diegelmann, 1997). Therefore, the anti-fibrotic effects of NO may be the result of a continuous and high level of local NO synthesis, like the one produced upon iNOS induction (Ferrini et al., 2002; Vernet et al., 2002). This shows the importance of the local levels of NO for either facilitating normal collagen deposition (wound healing) or preventing its accumulation (fibrosis).

Anti-fibrotic effects of NO may also be mediated by cGMP through guanylyl cyclase activation (Gonzalez-Cadavid et al., 1999). cGMP analogs inhibit collagen synthesis (Chen et al., 1999a, 1999b; Redondo et al., 1998), fibroblast replication (Chiche et al., 1998; Pandey et al., 2000), myofibroblast differentiation (Tao et al., 1999), and promote apoptosis (Loweth et al., 1997; Sirotkin et al., 2000; Taimor et al., 2000). PDE inhibitors, by elevating cGMP, also cause similar effects in vitro (Schade et al., 2002; Horio et al., 1999; Thompson et al., 2000), and in particular induce apoptosis in vivo (Chan et al., 2002; Takuma et al., 2001). Some of these PDE inhibitors, like pentoxifylline, are active in preventing experimental fibrosis in the lung, liver, and heart (Fischer et al., 2001; Desmouliere et al., 1999; Kremer et al., 1999), and are currently being used for the treatment of human liver fibrosis (Windmeier and Gressner, 1997) and Crohn's disease (Reimund et al., 1997).

Role of Myofibroblast in Fibrosis

One of the major pathological findings in tissue fibrosis is the presence of activated and proliferating myofibroblasts. These cells not only play an important role in the contraction phase of normal wound healing but they also are responsible for the development of tissue fibrosis or of a scar (Powel et al., 1999; Tomasek et al., 1999; Walker et al., 2001). The myofibroblast (FIG. 1) is the cell widely believed to generate the contracture in Dupuytren's disease, the condition present in 10-20% of PD cases (Connelly, 1999). It is believed that after fulfilling its role in wound contraction and in secreting collagen during healing, the myofibroblast disappears by programmed cell death (apoptosis) (Gabbiani, 1996). However, in Dupuytren's disease and other fibrotic conditions the myofibroblast persists, resulting in a persistent fibrosis and contracture (Kloen, 1999; Badalamente and Hurst, 1999). Morphologically, myofibroblasts are intermediate between the fibroblast and the smooth muscle cell. Phenotypically, they express large bundles of actin filaments (actin, myosin, and associated proteins: "stress fibers"), with a fibrillar space material named the "fibronexus", composed of fibronectin. Myofibroblasts can be identified by the detection of both α smooth muscle actin (ASMA) (absent in fibroblasts), and vimentin (absent in smooth muscle cells).

It is believed that myofibroblasts can originate from either fibroblasts, smooth muscle cells, or from an as yet uncharacterized stem cell (Powel et al., 1999; Tomasek et al., 1999; Walker et al., 2001). Upon the appropriate stimulation, the myofibroblast may revert back to a fibroblast or smooth muscle cell. Myofibroblasts express receptors for TGF-β1, PDGF, bFGF, endothelin, and prostaglandins. All these factors generate in culture, an "activated" myofibroblast that is able to proliferate. In liver fibrosis, this activated form of the myofibroblast can be transformed into the non-proliferating "stellate" form by either cAMP or PGE2 (Powel et al., 1999; Tomasek et al., 1999; Walker et al., 2001; Wu and Zern, 2000). The activated myofibroblast is then able to secrete cytokines, TGF-β1 and other growth factors, and inflammatory mediators. Within the latter category, the cell has been shown to release NO and ROS, and matrix proteins involved in wound repair and fibrosis, such as collagens I, III, IV, VI, and XVIII, laminins, proteoglycans, adhesion molecules and MMPs (Powel et al., 1999; Tomasek et al., 1999; Walker et al., 2001).

The myofibroblast is involved in functions such as wound repair in skin and repair of the myocardium after myocardial infarction. This cell has been implicated in the pathophysiology of the Dupuytren contracture, keloids, myocardial fibrosis, ischemia reperfusion injury, coronary artery restenosis, glomerulonephritis, liver cirrhosis, pulmonary interstitial fibrosis, and many other fibrotic conditions (Powel et al., 1999; Tomasek et al., 1999; Walker et al., 2001). However, in PD, there are few reports on the role of the myofibroblasts, other than the description of the original culture of fibroblasts from the PD plaque (Somers et al., 1982) and a few more recent studies (Anderson et al., 2000a, 2000b; Mulhall et al., 2001a, 2001b) and our own work (Vernet et al., 2002; Gonzalez-Cadavid et al., 2002; Gholami et al., 2002). In cell culture, PD fibroblasts demonstrate a faster replication rate as compared to those from the normal TA, a higher production of a pro-fibrotic agent (basic fibroblast growth factor), and a potential alteration of the p53 pathway that normally represses cell replication and favors apoptosis, which would indicate a sort of "immortalization" in culture (Anderson et al., 2000a, 2000b; Mulhall et al., 2001a, 2001b). Other groups have studied fibroblast cultures from the Peyronie's plaque but did not focus on their myofibroblast content (Duncan et al., 1991; El-Sakka et al., 1997a).

Animal Models of PD

An animal model of PD has recently been developed (El-Sakka et al., 1997b; El-Sakka et al., 1998), based on the administration of a synthetic heptapeptide of human TGF-β1 directly into the TA of the rat. After 45 days, the animal develops histological alterations and collagen deposition resembling those observed in the human PD plaque (El-Sakka et al., 1997a, 1997b, 1998). The administration of the full human TGF-β1 protein to the TA leads to a similar process in the rat model (Vernet et al., 2002; Gonzalez-Cadavid et al., 2002; Gholami et al., 2002; El-Sakka et al., 1999, 1998).

Another potentially useful animal model for the study of the pathophysiology of the PD plaque is the collagen I promoter transgenic mouse (Fakhouri et al., 2001; Tharaux et al., 2000). This mouse carries the regulatory region of the collagen I-α2 gene linked to two reporter genes, luciferase and β-galactosidase, so that whenever collagen mRNA synthesis is stimulated luciferase and β-galactosidase will be expressed. Both proteins can be estimated by a chemiluminescence reaction in tissue homogenates, and β-galactosidase specifically by the development of a blue color in tissue sections.

This collagen 1 promoter mouse model has recently been used (Dussaule et al., 2000) to demonstrate the link between NO, endothelin, and collagen synthesis in kidney fibrosis, which is characterized by collagen I accumulation. In essence, by giving the NOS inhibitor L-NAME to these transgenic mice for up to 14 weeks, it was possible to induce nephroangio- and glomerulo-fibrosis, accompanied by an increase in luciferase levels and an increased urinary excretion rate of endothelin. The blockade of endothelin receptors with the selective ET antagonist bosentan reduced collagen deposition in the L-NAME animals, and abolished collagen I promoter activation, as quantitated by luciferase activity. This animal model demonstrated that NO inhibition induces an early activation of the collagen I gene in the kidney arterioles and glomeruli, suggesting that NO inhibits collagen deposition and the endothelin-mediated fibrogenic effect, as confirmed by other studies (Boffa et al., 1999; Tharaux et al., 1999).

Nucleic Acids

In certain embodiments of the present invention, genes encoding one or more isoforms of PDE4, PDE5, PKG, NOS, MMP or another protein may be incorporated into expression vectors for therapeutic use in fibrosis. As discussed below, a gene encoding a given protein may contain a variety of different bases and yet still produce a corresponding polypeptide that is indistinguishable functionally, and in some cases structurally, from the known sequences of such genes. It is a matter of routine for the skilled artisan to obtain known genomic and/or cDNA sequences encoding various proteins from publicly available sources, such as GenBank.

Any reference to a nucleic acid should be read as encompassing a host cell containing that nucleic acid and, in some cases, capable of expressing the product of that nucleic acid. Cells expressing nucleic acids of the present invention may prove useful in the context of screening for agents that induce, repress, inhibit, augment, interfere with, block, abrogate, stimulate, or enhance the catalytic activity and/or regulatory properties of PDE4 and/or PDE5.

Nucleic acids according to the present invention may contain an entire gene, a cDNA, or a domain of a protein that expresses catalytic activity. The nucleic acid may be derived from genomic DNA, i.e., cloned directly from the genome of a particular organism. In preferred embodiments, however, the nucleic acid would comprise complementary DNA (cDNA).

The DNA segments of the present invention include those encoding biologically functional equivalent proteins and peptides. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

Expression Vectors

Nucleic acids encoding proteins or peptides may be incorporated into expression vectors for production of the encoded proteins or peptides. Non-limiting examples of expression systems known in the art include bacteria such as *E. coli*, yeast such as *Pichia pastoris*, baculovirus, and mammalian expression systems such as in COS or CHO cells. A complete gene can be expressed or, alternatively, fragments of the gene encoding portions of polypeptide can be produced.

The gene or gene fragment encoding a polypeptide may be inserted into an expression vector by standard subcloning techniques. An *E. coli* expression vector may be used which produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.).

Some of these systems produce recombinant polypeptides bearing only a small number of additional amino acids, which are unlikely to affect the antigenic ability of the recombinant polypeptide. For example, both the FLAG system and the 6×His system add only short sequences, both of which are known to be poorly antigenic and which do not adversely affect folding of the polypeptide to its native conformation. Other fusion systems are designed to produce fusions wherein the fusion partner is easily excised from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

The expression system used may also be one driven by the baculovirus polyhedron promoter. The gene encoding the polypeptide may be manipulated by standard techniques in order to facilitate cloning into the baculovirus vector. One baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant antigen. See U.S. Pat. No. 4,215,051 (incorporated by reference).

Amino acid sequence variants of the polypeptide may also be prepared. These may, for instance, be minor sequence variants of the polypeptide which arise due to natural variation within the population or they may be homologues found in other species. They also may be sequences which do not occur naturally but which are sufficiently similar that they function similarly and/or elicit an immune response that cross-reacts with natural forms of the polypeptide. Sequence variants may be prepared by standard methods of site-directed mutagenesis such as those described herein.

Substitutional variants typically contain an alternative amino acid at one or more sites within the protein, and may be designed to modulate one or more properties of the polypeptide such as stability against proteolytic cleavage. Substitutions preferably are conservative, that is, one amino acid is replaced with one of similar size and charge. Conservative substitutions are well known in the art and include, for example, the changes of: arginine to lysine; asparagine to glutamine or histidine; aspartate to glutamate; cysteine to serine; glutamine to asparagine; glutamate to aspartate; histidine to asparagine or glutamine; isoleucine to leucine or valine; leucine to valine or isoleucine; lysine to arginine or glutamine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also may include hybrid proteins containing sequences from other proteins and polypeptides which are homologues of the polypeptide. For example, an insertional variant may include portions of the amino acid sequence of the polypeptide from one species, together with portions of the homologous polypeptide from another species. Other insertional variants may include those in which additional amino acids are introduced within the coding sequence of the polypeptide. These typically are smaller insertions than the fusion proteins described above and are introduced, for example, to disrupt a protease cleavage site.

The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

As used herein, the terms "engineered" and "recombinant" cells are intended to refer to a cell into which an exogenous DNA segment or gene, such as a cDNA or gene has been introduced through the hand of man. Therefore, engineered cells are distinguishable from naturally occurring cells that do not contain a recombinantly introduced exogenous DNA segment or gene. Recombinant cells include those having an introduced cDNA or genomic gene, and also include genes positioned adjacent to a heterologous promoter not naturally associated with the particular introduced gene.

To express a recombinant encoded protein or peptide, whether mutant or wild-type, in accordance with the present invention one would prepare an expression vector that comprises one of the claimed isolated nucleic acids under the control of, or operatively linked to, one or more promoters. To bring a coding sequence "under the control of" a promoter, one positions the 5' end of the transcription initiation site of the transcriptional reading frame generally between about 1 and about 50 nucleotides "downstream" (i.e., 3') of the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in *Saccharomyces*, the plasmid YRp7, for example, is commonly used (Stinchcomb et al., *Nature,* 282: 39, 1979; Tschemper et al., *Gene,* 10:157, 1980). This plasmid contains the trp1 gene which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.,* 255:2073, 1980) or other glycolytic enzymes (Hess et al., *J. Adv. Enzyme Reg.,* 7:149, 1968; Holland et al., *Biochemistry,* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the encoded protein. In preferred embodiments of the invention, the host cells are human cells inside a subject with a fibrotic condition.

Different host cells have characteristic and specific mechanisms for the post-translational processing and modification of proteins. Appropriate cells lines or host systems may be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment that also contains the SV40 viral origin of replication. Smaller or larger SV40 fragments may also be used, provided there is included the approximately 250 bp sequence extending from the Hind site toward the Bgl I site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons may be of a variety of origins, both natural and synthetic. The efficiency of expression may be enhanced by the inclusion of appropriate transcription enhancer elements or transcription terminators (Bittner et al., *Methods in Enzymol,* 153: 516-544, 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

Nucleic Acid Delivery
Liposomal Formulations

In certain broad embodiments of the invention, the oligo- or polynucleotides and/or expression vectors may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, In: *Liver Diseases, Targeted Diagnosis and Therapy Using Specific Receptors and Ligands,* Wu et al. (Eds.), Marcel Dekker, New York, pp 87-104, 1991). Also contemplated are cationic lipid-nucleic acid complexes, such as lipofectamine-nucleic acid complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al., *Science,* 243:375-378, 1989). In other embodiments, the liposome may be complexed or employed in conjunction with nuclear non-histone chromosomal proteins (HMG-1). In that such expression vectors have been employed in transfer and expression of a polynucleotide in vitro and in vivo, they may be applicable for the present invention. Liposomes within the scope of the present invention can be prepared in accordance with known laboratory techniques. In one embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40°C under negative pressure. The solvent normally is removed within about 5 min to 2 hours, depending on the desired volume of the liposomes. The composition can be dried further in a desiccator under vacuum. The dried lipids generally are discarded after about 1 week because of a tendency to deteriorate with time.

The dried lipids or lyophilized liposomes prepared as described above may be reconstituted in a solution of nucleic acid and diluted to an appropriate concentration with an suitable solvent. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50-200 mM. The amount of nucleic acid encapsulated can be determined in accordance with standard methods. After determination of the amount of nucleic acid encapsulated in the liposome preparation, the liposomes may be diluted to appropriate concentration and stored at 4°C until use.

Alternative Delivery Systems

Adenoviruses: Human adenoviruses are double-stranded DNA tumor viruses with genome sizes of approximate 36 kB. As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B, which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, In: *Human Gene Transfer*, O. Cohen-Haguenauer et al., eds., John Libbey Eurotext, France, pp. 51-61, 1991).

As only a small portion of the viral genome appears to be required in cis (Tooze, *Molecular Biology of DNA Tumor Viruses*, 2nd ed., Cold Spring Harbor Laboratory, Cold Spring Harbor, N.Y., 1991), adenovirus-derived vectors offer excellent potential for the substitution of large DNA fragments when used in connection with cell lines such as 293 cells. Ad5-transformed human embryonic kidney cell lines (Graham et al., *J. Gen. Virol.*, 36:59-72, 1977) have been developed to provide the essential viral proteins in trans.

Advantages of adenovirus vectors over retroviruses include the higher levels of gene expression. Adenovirus replication is independent of host gene replication, unlike retroviral sequences. Because adenovirus transforming genes in the E1 region can be readily deleted and still provide efficient expression vectors, oncogenic risk from adenovirus vectors is thought to be low (Grunhaus and Horwitz, *Seminar in Virology*, 3:237-252, 1992).

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 kB of foreign DNA and can be grown to high titers in 293 cells (Stratford-Perricaudet and Perricaudet, 1991). Persistent expression of transgenes following adenoviral infection has also been reported.

Other Viral Vectors as Expression Constructs. Other viral vectors may be employed as expression constructs in the present invention. Vectors derived from viruses such as vaccinia virus (Baichwal and Sugden, In: *Gene Transfer*, Kucherlapati R, ed., New York, Plenum Press, pp. 117-148, 1986) adeno-associated virus (AAV) (Baichwal and Sugden, 1986) and herpes viruses may be employed. They offer several attractive features for various mammalian cells (Horwich, et al., *J. Virol.*, 64:642-650, 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., *Hepatology*, 14:124A, 1991).

Non-viral Methods. Several non-viral methods for the transfer of expression vectors into cultured mammalian cells also are contemplated by the present invention. These include calcium phosphate precipitation (Graham and van der Eb, *Virology*, 52:456-467, 1973) DEAE-dextran (Gopal, *Mol. Cell Biol.*, 5:1188-1190, 1985), lipofectamine-DNA complexes, and receptor-mediated transfection (Wu and Wu, *Biochemistry*, 27: 887-892, 1988; Wu and Wu, *J. Biol. Chem.*, 262: 4429-4432, 1987). Some of these techniques may be successfully adapted for in vivo or ex vivo use.

In one embodiment of the invention, the expression construct may simply consist of naked recombinant vector. Transfer of the construct may be performed by any of the methods mentioned above which physically or chemically permeabilize the cell membrane. For example, Dubensky et al. (*Proc. Nat. Acad. Sci. USA*, 81:7529-7533, 1984) injected polyomavirus DNA in the form of $CaPO_4$ precipitates into liver and spleen of adult and newborn mice demonstrating active viral replication and acute infection.

Anti-Sense

The term "antisense" is intended to refer to polynucleotide molecules complementary to a portion of a targeted gene or mRNA species. "Complementary" polynucleotides are those that are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

The intracellular concentration of monovalent cation is approximately 160 mM (10 mM $Na^+$; 150 mM $K^+$). The intracellular concentration of divalent cation is approximately 20 mM (18 mM $Mg^+$; 2 mM $Ca^{++}$). The intracellular protein concentration, which would serve to decrease the volume of hybridization and, therefore, increase the effective concentration of nucleic acid species, is 150 mg/ml. Constructs can be tested in vitro under conditions that mimic these in vivo conditions.

Antisense constructs may be designed to bind to the promoter and other control regions, exons, introns or even exon-intron boundaries of a gene. It is contemplated that effective antisense constructs may include regions complementary to the mRNA start site. One can readily test such constructs simply by testing the constructs in vitro to determine whether levels of the target protein are affected. Similarly, detrimental non-specific inhibition of protein synthesis also can be measured by determining target cell viability in vitro.

As used herein, the terms "complementary" or "antisense" mean polynucleotides that are substantially complementary to the target sequence over their entire length and have very few base mismatches. For example, sequences of fifteen bases in length may be termed complementary when they have a complementary nucleotide at thirteen or fourteen nucleotides out of fifteen. Sequences that are "completely complementary" will be sequences which are entirely complementary throughout their entire length and have no base mismatches.

Other sequences with lower degrees of homology also are contemplated. For example, an antisense construct that has limited regions of high homology, but also contains a non-homologous region (e.g., a ribozyme) could be designed. These molecules, though having less than 50% homology, would bind to target sequences under appropriate conditions.

Although the antisense sequences may be full length cDNA copies, or large fragments thereof, they also may be shorter fragments, or "oligonucleotides," defined herein as polynucleotides of 50 or less bases. Although shorter oligomers (8-20) are easier to make and increase in vivo accessibility, numerous other factors are involved in determining the specificity of base-pairing. For example, both binding affinity and sequence specificity of an oligonucleotide to its complementary target increase with increasing length. It is contemplated that oligonucleotides of 8, 9, 10, 11, 12, 13, 14, 15, 16, 17, 18, 19, 20, 25, 30, 35, 40, 45, 50 or 100 base pairs will be used. While all or part of the gene sequence may be employed in the context of antisense construction, statistically, any sequence of 14 bases long should occur only once in the human genome and, therefore, suffice to specify a unique target sequence.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., *Science*, 260:1510-1513, 1993).

Alternatively, the antisense oligo- and polynucleotides according to the present invention may be provided as RNA via transcription from expression constructs that carry nucleic acids encoding the oligo- or polynucleotides. Throughout this application, the term "expression construct" is meant to include any type of genetic construct containing a nucleic acid encoding a product in which part or all of the nucleic acid sequence is capable of being transcribed. Typical expression vectors include bacterial plasmids or phage, such as any of the pUC or Bluescript™ plasmid series or viral vectors adapted for use in eukaryotic cells.

In preferred embodiments, the nucleic acid encodes an antisense oligo- or polynucleotide under transcriptional control of a promoter. The term promoter will be used here to refer to a group of transcriptional control modules that are clustered around the initiation site for RNA polymerase II. Promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. A variety of specific eukaryotic promoter elements are known in the art and any such known element may be used in the practice of the claimed invention. Depending on the promoter, it appears that individual elements can function either co-operatively or independently to activate transcription. The particular promoter that is employed to control the expression of a nucleic acid encoding the inhibitory peptide is not believed to be important, so long as it is capable of expressing the peptide in the targeted cell.

Enhancers are genetic elements that increase transcription from a promoter located at a distant position on the same molecule of DNA. Enhancers are organized much like promoters. That is, they are composed of many individual elements, each of which binds to one or more transcriptional proteins. Any promoter/enhancer combination known in the art (e.g., the Eukaryotic Promoter Data Base) also could be used to drive expression of the gene.

Where a cDNA insert is employed, typically one will typically include a polyadenylation signal to effect proper polyadenylation of the gene transcript. The nature of the polyadenylation signal is not believed to be crucial to the successful practice of the invention, and any such sequence may be employed, such as human growth hormone and SV40 polyadenylation signals. Also contemplated as an element of the expression construct is a terminator. These elements can serve to enhance message levels and to minimize read through from the construct into other sequences.

In certain embodiments of the invention, the delivery of a nucleic acid in a cell may be identified in vitro or in vivo by including a marker in the expression construct. The marker would result in an identifiable change to the transfected cell permitting identification of expression. Enzymes such as herpes simplex virus thymidine kinase (tk) (eukaryotic) or chloramphenicol acetyltransferase (CAT) (prokaryotic) may be employed.

siRNA

Small interfering RNAs (siRNAs) are short RNA molecules (typically from 21 to 23 nucleotides in length) that may be used to induce targeted gene silencing by RNA interference (Myers et al., *Nature Biotechnology* 21:324-328, 2003; Elbashir, *Nature* 411:494-498, 2001; Caplen et al., *Proc. Natl. Acad. Sci. USA* 98:9742-47, 2001). SiRNAs occur naturally in vivo when double-stranded RNA is cleaved by ribonuclease III to produce a short siRNA sequence. Synthetic siRNAs may also be introduced into cells to inhibit expression of one or more selected genes. SiRNAs may be generated by standard solid-phase oligonucleotide synthesis, by RNA-specific endonuclease cleavage of double-stranded RNA, or by expression of transfected DNA templates incorporating promoter sequences for RNA polymerase III. Introduction of siRNA into a mammalian cell results in the targeted destruction of messenger RNAs of the same sequence. Commercial products for siRNAs are available from a number of sources, such as Gene Therapy Systems, Inc. (San Diego, Calif.), Promega (Madison, Wis.) and Sirna Therapeutics (Boulder, Colo.).

Methods for design of siRNA sequences are publicly available. For example, the siRNA Target Finder may be used online at the Ambion website. Target mRNA sequences are input into the program, which then scans for 21 nucleotide sequences that begin with an AA dinucleotide. The program selects for siRNAs with about a 30 to 50% GC content, avoiding sequences with 4-6 polyT stretches that would function as terminators for RNA Polymerase III transcription. After selection of two to four siRNA candidates, the generated sequences may be searched for homology (for example, using the BLAST search engine on the NCBI server) to other untargeted mRNA sequences. SiRNAs with homology to non-targeted sequences are eliminated from consideration. SiRNA expression cassettes may also be obtained from Ambion (Austin, Tex.). SiRNAs may be purchased and used according to the manufacturer's instructions to provide targeted inhibition of the expression of specific genes, such as PDE-4 and/or PDE-5.

Ribozymes

Another method for inhibiting the expression of specific genes within the scope of the present invention is via ribozymes. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). It was reported that ribozymes elicited genetic changes in some cells lines to which they were applied. The altered genes included the oncogenes H-ras, c-fos and genes of HIV. Most of this work involved the modification of a target mRNA, based on a specific mutant codon that is cleaved by a specific ribozyme.

Several different ribozyme motifs have been described with RNA cleavage activity (Symons, 1992). Examples that are expected to function equivalently include sequences from the Group I self splicing introns including Tobacco Ringspot Virus (Prody et al., 1986), Avocado Sunblotch Viroid (Palukaitis et al., 1979; Symons, 1981), and Lucerne Transient Streak Virus (Forster and Symons, 1987). Sequences from these and related viruses are referred to as hammerhead ribozyme based on a predicted folded secondary structure.

Other suitable ribozymes include sequences from RNase P with RNA cleavage activity (Yuan et al., 1992, Yuan and Altman, 1994, U.S. Pat. Nos. 5,168,053 and 5,624,824), hairpin ribozyme structures (Berzal-Herranz et al., 1992; Chowrira et al., 1993) and Hepatitis Delta virus based ribozymes (U.S. Pat. No. 5,625,047). The general design and optimization of ribozyme directed RNA cleavage activity has been discussed in detail (Haseloff and Gerlach, 1988, Symons, 1992, Chowrira et al., 1994; Thompson et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence that is the cleavage site. For hammerhead ribozymes, the cleavage site is a dinucleotide sequence on the target RNA—a uracil (U) followed by either an adenine, cytosine or uracil (A,C or U) (Perriman et al., 1992; Thompson et al., 1995). The frequency of this dinucleotide occurring in any given RNA is statistically 3 out of 16. Therefore, for a given target messenger RNA of 1000 bases, 187 dinucleotide cleavage sites are statistically possible.

The large number of possible cleavage sites in genes of moderate size, coupled with the growing number of sequences with demonstrated catalytic RNA cleavage activity indicates that a large number of ribozymes that have the potential to downregulate gene expression are available. Additionally, due to the sequence variation among different genes, ribozymes could be designed to specifically cleave individual genes or gene products. Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in ribozymes targeted to specific genes is simply a matter of preparing and testing a given sequence, and is a routinely practiced "screening" method known to those of skill in the art.

Formulations and Routes for Administration to Patients

In certain embodiments, the inhibitors or activators of PDE5, PKG, NOS, MMP or another protein and/or stimulators or agonists of cGMP may be used for therapeutic treatment of medical conditions, such as Peyronie's disease. Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

Aqueous compositions of the present invention comprise an effective amount of inhibitor or activator, dissolved or dispersed in a pharmaceutically acceptable carrier or aqueous medium. Such compositions also are referred to as innocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the inhibitors or activators of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions normally would be administered as pharmaceutically acceptable compositions.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions of the present invention may be formulated in a neutral or salt form. Pharmaceutically-acceptable salts include the acid addition salts which are formed by reaction of basic groups with inorganic acids such as, for example, hydrochloric or phosphoric acids, or such organic acids as acetic, oxalic, tartaric, mandelic, and the like. Salts formed with free acidic groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The results disclosed below are generally addressed to the following areas.
NO/cGMP The antifibrotic effects of agents that, either orally or via gene transfer, stimulate the NO/cGMP pathways and increase NO levels and cGMP levels or PKG activity or agents that inhibit oxidative stress by decreasing ROS levels. For example, by a) gene transfer of the sense cDNA for iNOS or nNOS in a single transfection; b) long-term administration of an oral NO donor (e.g. molsidomine), or the NOS substrate (L-arginine) that produces a continuously elevated level of NO. Alternatively, by increasing cGMP and/or stimulating PKG by a) identifying PDE isoforms present in the affected tissue and using oral PDE inhibitors such as sildenafil, zaprinast, and pentoxifylline; b) by gene transfer of PKG1 cDNA, or its mutated version, to increase the level of PKG activation. In other alternatives, by reducing the concentration of ROS by a) early (to arrest the development of the PD-like plaque, arteriosclerotic plaque or other fibrotic lesion) or late (to induce regression of an already formed plaque) administration of oral antioxidants such as vitamin E or S-adenosyl methionine (SAME); b) combination therapy with antioxidant (Vitamin E or SAME) combined with one or more NO donors (molsidomine or L-arginine) or cGMP/PKG therapy (sildenafil, zaprinast, pentoxifylline, or PKG1 cDNA), to induce regression of the plaque (late treatment).

MMP

Stimulation of MMP (collagenolysis) induced by thymosin peptides or other MMP activators. Correlating MMP inhibition in fibrosis with the levels of TIMP1, an inhibitor of MMP. Use of the MMP inducers thymosin β-4 and 10 are to stimulate MMP activity.

Materials and Methods

Human Tissues and Cell Cultures

Human tissue: Human TA was obtained from non-PD patients (n=4), two undergoing partial penectomy due to penile cancer and two undergoing penile prosthesis surgery. Plaque tissue was isolated from PD patients (n=8) who underwent a surgical procedure to treat this condition (Vernet et al., 2002; Ferrini et al., 2002; Magee et al., 2002b; Davila et al., 2003b). Fragments of newly obtained tissue are stored for 24 h in "RNA-later" (Ambion, Inc., Austin, Tex.), for RNA analysis, in 4% formalin for histochemistry and immunohistochemistry, or in culture medium (DMEM/10% fetal calf serum) or fibroblast growth medium (FGM-2) (Clonetics, Walkersville, Md.) with 20% fetal bovine serum, for protein analysis or cell culture. Tissues were then frozen at –80° C. until further use, except for fixed portions that were stored at 4° C. in PBS until paraffin embedding or cryosectioning, and pieces used for cell cultures.

Primary human cell cultures: Human fibroblast primary cultures were obtained from fragments of PD plaque or TA essentially according to Smith and Liu (2002), and their purity was established by immunohistochemistry, as detailed below. New primary cultures were obtained from fragments of PD plaque or TA that were washed in Hanks solution, minced in a fibroblast growth medium (FGM) (BioWhittaker Inc., Walkersville, Md.) and 20% fetal bovine serum (FBS), and plated onto a 25 cm$^2$ culture flask per specimen (Vernet et al., 2002). Fragments were left undisturbed until attachment for about 1 week. Once the monolayer started to develop, the fragment was removed. Medium with 10% FBS was changed once a week and when cells achieved approximately 80% confluence (3-4 weeks) they were trypsinized and split onto 10 cm plates. Cells were allowed to grow again to 80% confluence, with medium changed twice a week. The cells collected from this passage were considered as passage 1. Successive passages were performed at 1/3 split ratio, and studies were carried out on cells from passages 3 onwards. Studies were performed with PD cells from the 4$^{th}$ to the 10$^{th}$ passages. Cells were incubated on: a) 75 cm$^2$ flasks for RNA isolation; b) 6-well plates for protein isolation; and c) 8-well removable chambers for cytochemistry and immunocytochemistry. Treatments with different additions were initiated 24 hours after plating and continued for different periods.

Cells incubated in 8-well chamber slides were allowed to grow to 50-60% confluence. At this point, cells received in duplicate sildenafil, pentoxifylline, or 8-Br cGMP at the concentrations indicated, and were allowed to propagate for 3 days without changing medium. In certain cases SNAP was added and replaced daily after changing the medium (Vernet et al., 2002). All studies were done in duplicate or triplicate. For the isolation of rat TA fibroblasts, the TA was carefully dissected from rat corpora cavernosa tissue, and cultures were developed and their purity tested as in the case of the human tissues.

Rodent Models and Tissue Processing

TGF-β1 rat model. Male Fisher 344 rats, 9-11 month old purchased from the NIH/NIA colony (Harlan Sprague-Dawley, Inc., San Diego, Calif.) and maintained under controlled temperature and lighting, were anesthetized and injected in the penile TA at the middle of the penis with either vehicle only (saline, group 1) or 0.5 µg recombinant human TGF-β1 (Biotech Diagnostic, Laguna Niguel, Calif., groups 2-5) as disclosed (Ferrini et al., 2002; Vernet et al., 2002). After the injection, groups 1 and 2 were given drinking water while the other groups received water with L-arginine (2.25 g/kg/day, group 3) (Moody et al., 1997), or sildenafil (10 mg/kg/day, group 4) or pentoxifylline (10 mg/kg/day, group 5). Forty-five days later, or as indicated, animals were sacrificed and perfused through the left ventricle with saline followed by 4% formalin ((Ferrini et al., 2002; Vernet et al., 2002). After the penises were excised, the penile skin was denuded by removing the glans and adhering non-crural tissue. The penile shaft was separated from the crura and 2-3 mm transverse slices were cut around the site of the saline or TGF-β1 injection. All tissues were post-fixed overnight in 4% formalin, washed in PBS and stored at 4° C.

TGF-β1-iNOS knock-out mouse model. The iNOS knock-out strain (B6;129PNOS2<TmlLeu>), where iNOS expression was genetically blocked, and the corresponding wild type control (B6;129 PF1/y) (Hochberg et al., 2000), were injected (2-3 months old) in the TA with TGF-β1 as in the rat and sacrificed 45 days later.

TGF-β1-collagen I promoter mouse model. The transgenic line pGB 19.5/13.5 was obtained from George Bou-Gharios (London, England). These animals harbor the promoter of the α2 chain of the mouse collagen type I gene linked to the E. coli β-galactosidase, that is expressed in cells and tissues where collagen I is normally expressed (Fakhouri et al., 2001; Tharaux et al., 2000; Dussaule et al., 2000). Animals were injected into the TA as above with TGF-β1, and sacrificed.

Arterial Tree Rodent Model. Young (3-month) and aged (22-24 month) male Brown Norway rats were obtained from the NIH/NIA colony (Harlan Sprague-Dawley, Inc., San Diego, Calif.), and maintained under controlled temperature and lighting. One half of the aged animals were treated for 3 weeks with L-NIL at 0.1 g/l in the drinking water, while the rest of the animals received plain drinking water. Animals were anesthetized, pretreated with heparin, and perfused through the left ventricle with saline followed by 4% formalin. The abdominal aorta, brachial and femoral neurovascular bundles as well as the penis, denuded of its skin, were removed and post-fixed overnight in 4% formalin, and washed and stored in PBS at 4 C until paraffin embedding.

General Procedures

Injection-electroporation. Injection into the TA was performed with the appropriate AdV or plasmid cDNA constructs at doses described below, and electroporation was applied at 100 volts, 8 pulses/sec, 40 ms (Magee et al., 2002a).

Minipump implantation. Alza osmotic minipumps (Alza Corp, Palo Alto, Calif.), #2001D, delivering 8 ul/hr of a saline solution (100 ul) containing the selected compound during a period of 24 hs for "short-term" treatment, or 0.25 ul/hour, for 2 weeks (Alza#1002) for "long-term" treatment, were implanted in a subcutaneous tunnel over the inguinal canal, and attached to the abdominal muscles with a non-absorbable suture. A delivery catheter from the minipump was placed through the tissues to the penile crura and sutured to the perineal muscles, as previously described (Garban et al., 1997; Gelman et al., 1998).

Detection of PDE mRNA Expression in Tissues and Cells

Total RNA was isolated from the human TA and PD tissues, from their respective fibroblast cultures, and from rat TA and penile shaft tissues, and their respective fibroblast and smooth muscle cell cultures, by the Trizol procedure (Gibco BRL, Gaithesburg, Md.). RNA was then submitted (1 ug) to reverse transcription (Vernet et al., 2002; Magee et al., 2002b; Ferrini et al., 2001b) using Superscript II RNase H⁻ reverse transcriptase (Gibco BRL) and random primers (0.25 ug), followed by PCR with the respective gene specific primers (Kuthe et al., 2001): a) for human PDE5A, on nt 1027-1049 (forward) and nt 1788-1764 (reverse) of the respective cDNA (Genbank #I58526); encompassing a 762 bp band common to the three variants 1-3; b) for rat PDE5A, the primers on nt 1905-1924 (forward) and nt 2479-2460 (reverse) of the respective cDNA (Genbank #NM 133584), generating a 575 bp band; c, d) for human PDE4A and B, on nt 942-965 (forward) and 1824-1802 (reverse), and nt 1909-1931 (forward) and 2315-2292 (reverse), respectively, of the cDNAs (Genbank #NM 006202 and NM 002600, respectively); as the source of the expected 883 bp (A) and 406 bp (B) bands; e) for rat PDE4, the primers on nt 241-260 (forward) and nt 656-637 (reverse) of the respective cDNA (Genbank #M25350), generating a band of 416 bp. PCR products were separated by electrophoresis on 1% agarose gels and stained with ethidium bromide. For densitometry, normalization was performed against the GAPDH housekeeping gene fragment generated in the same PCR reaction.

Detection of PDE5 and 4 Protein Expression in Tissue and Cell Extracts

Tissue extracts were obtained by homogenizing in a 1:6 wt/vol ratio in a buffer containing 0.32 M sucrose, 20 mM HEPES (pH 7.2), 0.5 mM EDTA, 1 mM dithithreitol and protease inhibitors (3 µM leupeptin, 1 µM pepstatin A, 1 mM phenylmethyl sulfonyl fluoride). In the case of cell extracts 0.5 ml of this solution per 10 cm Petri dish was used. The particulate and cytosolic fractions were obtained by homogenization of the cells in a Polytron Homogenizer, (Brinkmann, Switzerland), and centrifugation at 12,000×g for 60 min.

Equal amounts of protein (30 ug) were run on 7.5% polyacrylamide gels, and submitted to western blot immunodetection with polyclonal anti-mouse PDE5 (against cGMP binding region) IgG (1:1000) (Calbiochem, La Jolla, Calif.), and a secondary donkey anti-mouse IgG linked to horse radish-peroxidase (Amersham Pharmacia, Piscataway, N.J.), followed by a luminol reaction (Simko and Simko, 2000; Magee et al., 2002b; Ferrini et al., 2001b). Human PDE5 does not cross-react with other PDE5 isoforms. Negative controls were performed without primary antibody.

For PDE4 immunodetection, the following affinity purified IgGs were used (FabGennix Inc., Shreveport, La.): a) anti-PDE4A selective antibody (detecting variants identified by 1, 5, 8, x, and unassigned); b) anti-PDE4B (detecting variants 1-4), and anti-PDE4D (detecting variants 1-5) (Salanova et al., 1999).

The presence of PDEs in the PD fibroblasts in culture was confirmed by the ability of increasing concentrations of sildenafil and pentoxifylline to raise the basal cGMP and cAMP levels in triplicate wells, either in the absence or the presence of the NO donor, SNAP (S-nitroso-N-acetyl penicillamine) (Alexis Biochemicals, San Diego, Calif.) added daily at 100 µM, as measured by cGMP and cAMP EIA (enzyme immuno absorption) kits (Cayman Chemical, Ann Arbor, Mich.). Experiments were performed in duplicate. Values were expressed as pmoles cGMP or cAMP/mg protein. To normalize for differences between experiments, the changes in cGMP and cAMP levels exerted by sildenafil and pentoxifylline were expressed as % of their respective control values in the absence of the PDE inhibitors.

Histochemical and Immunohistochemical Determinations

In the case of cell cultures, at completion of incubations, slides were removed from the chambers and cells were fixed for immunodetection for 20 min in 4% buffered formalin at room temperature for α-smooth muscle actin (ASMA) (as a myofibroblast marker), vimentin (as a general fibroblast marker), and in certain cases for PDE5 and PDE4, or in ethanol at −20 C for collagen I and III (Vernet et al., 2002). The cells were quenched, blocked with normal goat serum and incubated with monoclonal primary antibodies for ASMA and vimentin (Sigma Immunohistology Kits, Sigma Chemical Co, St. Louis, Mo.), collagen I, and collagen III (1:40) (Chemicon International, Temecula, Calif.), overnight at 4° C. (Vernet et al., 2002; Ferrini et al., 2002). Processing was according with the manufacturer's instructions for ASMA, vimentin and collagen, consisting in the respective monoclonal antibodies and an anti-mouse biotinylated secondary antibody, followed by avidin-biotinylated HRP and the 3-amino-9-ethylcarbazol (AEC) chromogen. For PDE5A, the antibodies were as described above. Negative controls omitted the first antibodies or were replaced by IgG isotype at the same concentration of the first antibodies. Counterstaining was done with Mayer's hematoxylin. All the slides were mounted with Aqua Mount (Lerner, Pittsburgh, Pa.). For PDE4, the anti PDE4A and PDE4B affinity purified IgGs used for western blot was employed, and in addition the anti-PDE4A4 and anti-PDE4D (detecting variants 1-5) from the same source (FabGennix Inc.) were used.

In the case of tissue sections, the determinations of the collagen/smooth muscle ratio were carried out with Masson trichrome (Ferrini et al., 2002; Davila et al., 2003b) on adjacent 5 µm paraffin-embedded cross-sections from the human normal tunical or plaque tissues, or from a 2 mm area around the site of injection in the rat saline- and TGF-β1-injected shaft tissues. Other distal sections were obtained along the rat penile shaft.

SMC and collagen fibers within the corporal tissue and vascular tree were estimated by Masson trichromic staining (Sigma Diagnostic, St. Louis, Mo.) (Ferrini et al., 2002; Vernet et al., 2002; Davila et al, 2203b) in sections adjacent to those used for immunohistochemical staining, followed by image analysis to measure the ratio between SMC (red) and collagen fibers (blue). The results were expressed as red/blue ratios per area (see below). In the arterial tree, the intima/media thickness (IMT), and the diameter of the lumen were also measured.

The determinations of iNOS, nitrotyrosine, heme-oxygenase I, PAI-I (Davila et al., 2003b), manganese superoxide dismutase (MnSOD), and CuZn SOD (Cu/Zn SOD) (Martin et al., 1994) were carried out on 5 µm paraffin-embedded adjacent tissue sections, that. were quenched for endogenous peroxidase activity after deparaffinization and rehydration. Sections were blocked with normal goat serum, and incubated with polyclonal IgG antibodies against mouse iNOS (1:500) (Transduction Laboratories, Lexington, KT), nitrotyrosine (1:100) (Upstate, Lake Placid, N.Y.), Mn SOD and Cu/Zn SOD (Oxygen, Portland, Oreg.) (1:800 and 1:500 respectively), heme oxygenase I (Stressgen, San Diego, Calif.), or PAI-1 (Abcam Ltd, Cambridge, UK). For negative controls the first antibodies were replaced by IgG isotype. The detection was based on a secondary anti-rabbit biotinylated antibody (1:200) for iNOS and nytrotyrosine (Calbiochem, La Jolla, Calif.), or anti-sheep biotinylated antibody (1:200) for Cu/Zn and Mn SOD, followed by the ABC complex (1:100) (Calbiochem) and 3,3' diaminobenzidine (spelling) (DAB) (Sigma, St Louis Mo.). Sections were counterstained with hematoxylin.

TUNEL Assay for Apoptosis

The TUNEL assay (Ferrini et al., 2001a, 2001b) was performed in the adjacent matched tissue sections used for collagen, iNOS or nitrotyrosine staining, applying the Apoptag Oncor kit (Oncor, Gaithersburg, Md.). In brief, after deparaffinization and rehydration, sections were incubated with proteinase K (20 ug/ml) and endogenous peroxidase activity was quenched with 2% $H_2O_2$. Sections were incubated with digoxigenin-conjugated nucleotides and TdT, and subsequently treated with antidigoxigenin-peroxidase. To detect immunoreactive cells, sections were stained with 0.5% DAB/0.01% $H_2O_2$, and counterstained with 0.5% methyl green. As a negative control, buffer was substituted for the TdT enzyme. Testicular sections from old animals were used as positive control. For cell cultures, the cells were fixed in 4% formaldehyde for 30 min on ice, and post-fixed with ethanol-acetic acid 2/1 for 5 min at −20 C. Then the above procedure was applied, except that the proteinase K was omitted.

Quantitative Image Analysis (QIA)

The quantitation of the staining obtained by either histochemical or immunohisto/cytochemical techniques was performed by computerized densitometry using the ImagePro 4.01 program (Media Cybernetics, Silver Spring, Md.), coupled to an Olympus BHS microscope equipped with a Spot RT digital camera or VCC video camera (Wang et al., 2001; Ferrini et al., 2001a, 2001b; Davila et al., 2003b).

The number of positive cells was counted in a computerized grid against the total number of cells determined by counterstaining, and results were expressed as a percentage of positive cells over total cells. In addition, the integrated optical density (IOD) was obtained by measuring the density per object and multiplying it by the respective area. The sum of all the individual values in the field was then divided by the number of positive cells, to obtain the mean IOD/positive cell, as a measure of average immunoreactivity/cell. In certain cases, results were expressed as the unweighted average optical density per area (O.D/AREA), to determine the relative concentration of immunoreactive antigen. For collagen/smooth muscle staining, the ratio between the width of the area stained positive for collagen (blue) divided by the total area of the lacunar spaces plus smooth muscle (white+red) was employed. The apoptotic index (rate of programmed cell death) was calculated as the percentage of apoptotic cells within the total number of cells in a given area (non-apoptotic nuclei plus apoptotic cells). In all cases, five non-overlapping fields were screened per tissue section or per well. Three sections per tissue specimen from groups of five animals, or two wells per experimental point in cell incubations, were then used to calculate the means+/−SEM.

For iNOS, nitroyrosine, heme-oxygenase, PAI-1, MnSOD and Cu/Zn SOD determination, at least 6 sections per specimen were analyzed. Each slide assayed had its corresponding negative control. In certain cases, the number of immunopositive cells was determined as a percentage of the total counterstained nuclei in a computerized grid. In the Masson staining, the ratio between SMC (red) and collagen fibers (blue) was obtained and expressed per area. The rate of programmed cell death (apoptotic index) was expressed as the percentage of apoptotic cells within the total number of cells in a given area (non-apoptotic nuclei plus apoptotic cells).

Statistical Analysis

Values were expressed as mean (M)+/−standard error of the mean (SEM). The normality distribution of the data was established using the Wilk-Shapiro test, and the outcome measures between two groups were compared by the t test. Multiple comparisons among the different groups were analyzed by a single factor analysis of variance (ANOVA), followed by post-hoc comparisons with the Student-Neuman Keuls test, according to the Graph Pad prism V. 30. Differences among groups were considered significant at $P<0.05$.

Example 1

Spontaneous iNOS Induction In Vivo in the PD Plaque Leads to Increased NO Synthesis, Peroxynitrite Formation, and Fibroblast Apoptosis It has been reported that aging per se results in the spontaneous induction of iNOS and the formation of the NO metabolite, peroxynitrite, in both the rat hypothalamus (Ferrini et al., 2001b; Vernet et al., 1998) and corpora cavernosa (Ferrini et al., 2001a). This was accompanied by apoptosis of both the neurons and the cavernosal smooth muscle. In the TGF-β1 induced rat model of PD, a similar iNOS induction in the TA (Bivalacqua et al., 2000; Hellstrom, 2001) has been reported. Initially, it was assumed that this process of iNOS induction was deleterious to the TA.

As proposed herein, it is believed that iNOS induction in the TA, and perhaps in fibrosis in general, is a beneficial, anti-fibrotic, cellular defense mechanism. The locally produced NO from elevated iNOS would inhibit collagen deposition, oppose pro-fibrotic agents, and induce apoptosis of myofibroblasts, which pathologically persist in the PD plaque. This model has been examined in the TA (Ferrini et al., 2002; Vernet et al., 2002; Gonzalez-Cadavid et al., 2002; Gholami et al., 2002) by quantitative image analysis (QIA) of immunohistochemical and histochemical stained tissue sections, and measurement of RNA and protein expression by quantitative RT/PCR, northern blots, western blots, DNA microarrays, and other procedures (n=5 to 9 per experimental group). All results discussed below are significant (p<0.05), unless stated otherwise.

It was first observed that in the human PD plaque, iNOS induction as seen by immunohistochemistry occurs spontaneously in discrete cells (Ferrini et al., 2002). These cells were identified as fibroblasts and myofibroblasts based on vimentin as markers for both cell types and alpha smooth muscle actin (ASMA) for myofibroblasts (Vernet et al., 2002). iNOS expression as measured by immunohistochemistry was also detected in the rat PD-like plaque 45 days after TGF-β1 injection in the TA, in comparison to control tissue obtained from rats injected with saline (Ferrini et al., 2002; Vernet et al., 2002). In addition, in plaque tissue from both rat and human, iNOS induction was accompanied by increased peroxynitrite, a product formed by the reaction of NO with ROS (Ferrini et al., 2002). In contrast to its inductive effects on cell apoptosis, peroxynitrite does not induce collagen deposition or fibrosis, which means it is not pro-fibrotic per se (Okamoto et al., 1997), and therefore, differs considerably from one of the compounds from which it originates, ROS, that is highly pro-fibrotic (Casini et al., 1997; Muriel et al., 1998a; Hung et al., 1995; Poli, 2000; Curtin et al., 2002; Cattell, 2002; Kim et al., 2001).

The fibrotic plaque was visualized in the rat model by Masson staining showing disorganization of collagen fibers and intensification of collagen deposition and thickening of the TA (Ferrini et al., 2002). In the case of the human plaque, similar changes were revealed with Masson staining. We further observed an increase in collagen I mRNA levels and protein-bound hydroxy-proline, which are additional direct measurements of tissue collagen content (Ferrini et al., 2002). These initial results demonstrated that iNOS was strongly expressed in PD tissue and may play an important role in the plaque.

Figure 2:
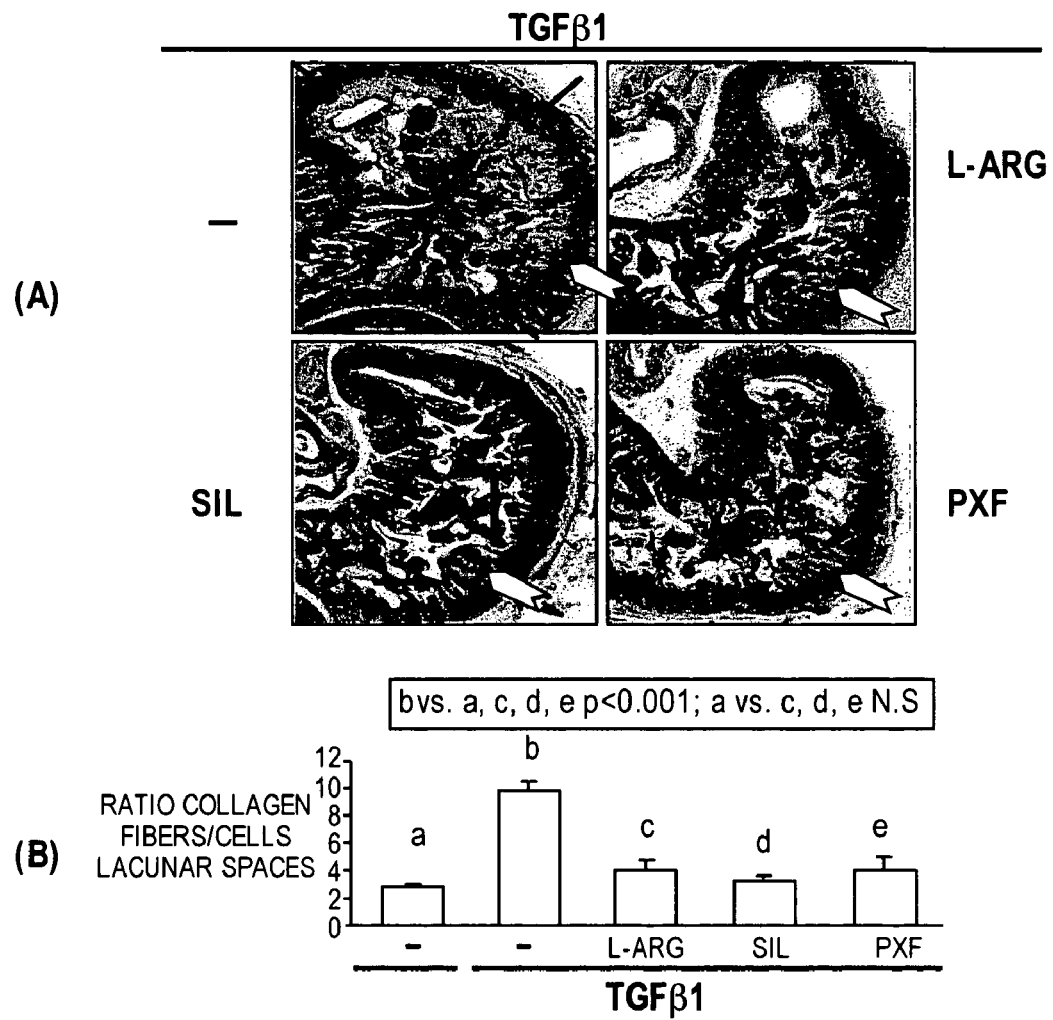
FIG. 2. Inhibition of collagen deposition in the fibrotic plaque induced by TGF-β1 in the rat TA, by long-term oral treatment with L-arginine and PDE inhibitors, estimated by Masson staining. (A) Microphotographs (40×) of cross sections of half of the rat penis. Dark arrows indicate the outer extent of plaque development and of tunical thickening. Light arrowheads (lower right-hand corner of each panel) indicate the site of TGF-β1 injection. The control (−) was injected with TGF-β1 injection, no treatment was given. L-ARG received a TGF-β1 injection and L-arginine in water. SIL received a TGF-β1 injection and sildenafil in water. PXF received a TGF-β1 injection and pentoxifylline in water. (B) QIA evaluation (n=5 per group). Five sections/animal, three fields/section.

To examine the specific role of NO on PD plaque formation, overall NOS activity was increased in the TA by treating the animals with the oral NOS substrate, L-arginine. The long-term oral administration of the NOS substrate, L-arginine, in the drinking water (2.25%), leads to a stimulation of NOS activity and NO synthesis in the whole penis (Moody et al., 1997) and should also be increased in the TA. In addition, NO has been shown to be a down-regulator of collagen synthesis (Haig et al., 1994). If NO has a down-regulatory effect on collagen synthesis in the plaque, then overproduction of NO should inhibit this collagen synthesis and prevent development or halt progression of the plaque. It was observed that increasing NO by oral L-arginine treatment for 45 days led to a considerable decrease in the size of the TGF-β1-induced plaque (FIG. 2A, top panels). The plaque in the rat model consists of disorganized collagen fibers and thickening of the TA that seems to spread extensively from the site of the TGF-β1 injection. This observed decrease in plaque development by oral L-arginine treatment was also verified by quantitating the ratio of the areas in the TA occupied by collagen fibers to the areas occupied by the cells and lacunar spaces (FIG. 2B). Changes in the width of the tunica as measured by QIA also confirmed these results (not shown). These observations demonstrate that NO, from oral NO donors, seems to play an anti-fibrotic role in the TA of the TGF-β1 injected rat model of PD.

Figure 3:
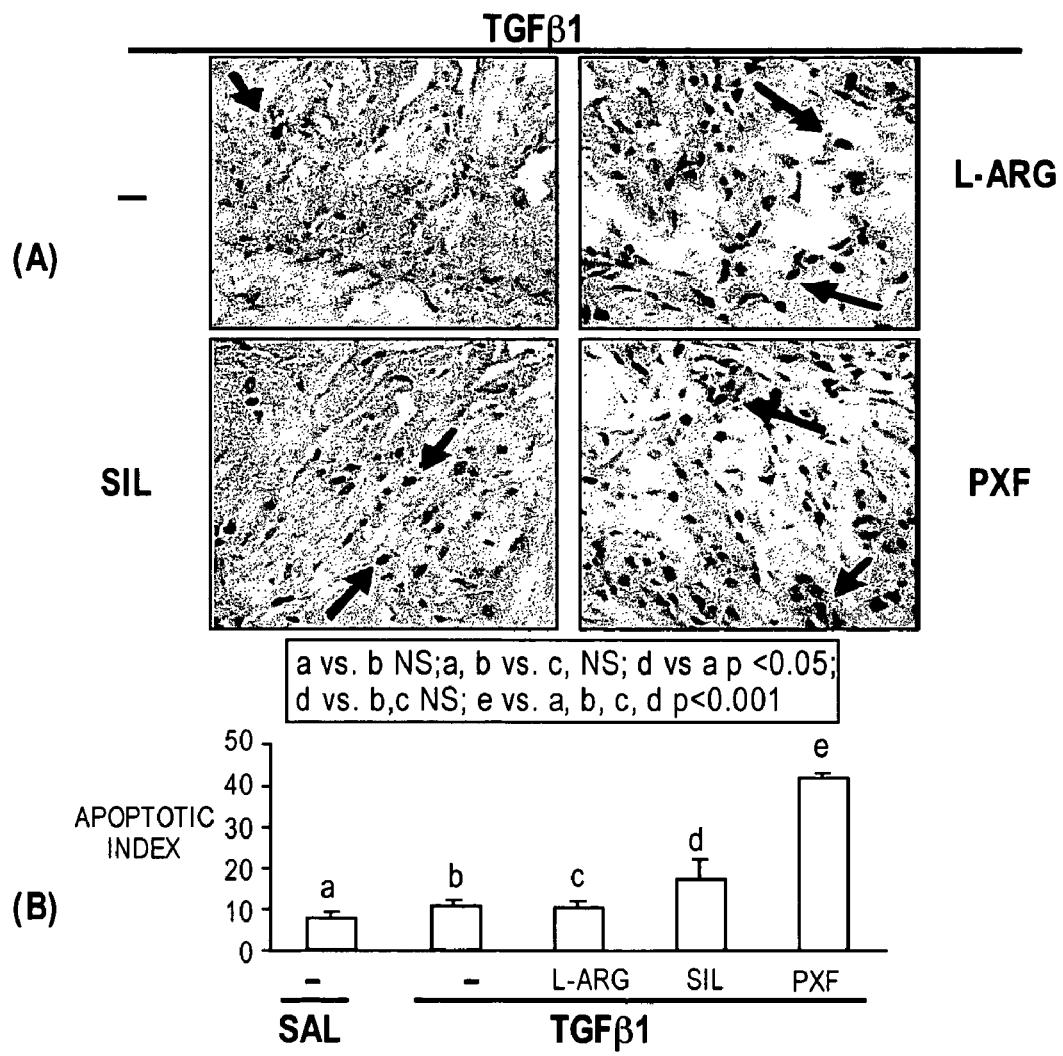
FIG. 3. Stimulation of apoptosis, as estimated by TUNEL, in the fibrotic plaque induced by TGF-β1 injection into the rat TA, following oral treatment with L-arginine, sildenafil or pentoxiphylline. (A) Microphotographs (400×) of tissue sections. Arrows indicate apoptotic cells in the site of the plaque. The control (−) was injected with TGF-β1 injection, no treatment was given. L-ARG received a TGF-β1 injection and L-arginine in water. SIL received a TGF-β1 injection and sildenafil in water. PXF received a TGF-β1 injection and pentoxifylline in water. (B) QIA (n=5 per group) as in FIG. 2.

Another major effect of high levels of NO in any tissue is its conversion, by its interaction with ROS, into peroxynitrite, which is a known inducer of apoptosis (Beckmann et al., 1996; Ferrini et al., 2001a; Vernet et al., 1998; Heigold et al., 2002; Duffield et al., 2000; Zhang et al., 1999). NO in the TA may also act to increase apoptosis of those cells within the PD plaque that are responsible for promoting collagen synthesis. In the PD animal model given oral L-arginine (2.25%), there appeared to be an increase in the number of apoptotic cells per field in the PD-like plaque as compared to the control animals (FIG. 3A, top panels). But when an apoptotic index (apoptotic cells/total number of cells) was used to quantify apoptosis, no significant difference was observed (FIG. 3B), because of the parallel increase in cell number.

Example 2

Inhibition of iNOS Activity In Vivo Stimulates Both Collagen Synthesis and Collagen Fiber Deposition in the Rat PD-Like Plaque The studies with L-arginine detailed in Example 1 show modulation of the size of the PD plaque by NO. To determine whether the NO involved in this anti-fibrotic process emanated from iNOS, we studied in the TGF-β1 rat model the effects of specifically blocking iNOS activity by the long-term oral administration of L-NIL, a specific iNOS inhibitor (Ferrini et al., 2002, Vernet et al., 2002). In the TGF-β1 injected rat model, treatment with L-NIL, which lowers NO derived from iNOS, induced a remarkable expansion and thickening of the TA that was due to excessive collagen fiber deposition (Ferrini et al., 2002). We also observed a considerable increase in peroxynitrite as indicated by nitrotyrosine formation in the TA (Ferrini et al., 2002). These observations further support the role of NO from iNOS in reducing the growth of the plaque in the rat TA.

The effect of L-NIL in increasing collagen in the TA of the TGF-β1 rat model may be due to an increase in collagen synthesis, a decrease in its normal breakdown, or both. To determine whether the larger PD plaque in the L-NIL treated rat is due, at least in part, to an increase in collagen I synthesis (the most prevalent collagen protein in the TA), and not simply to the inhibition of collagenolysis by the MMPs, we injected a cDNA plasmid construct of the collagen I promoter driving the expression of a reporter gene (Magee et al., 2002a) into the site of the original TGF-β1 or saline injection, 10 days prior to sacrifice and 35 days after the TGF-β1 injection. This plasmid is an indicator of collagen I transcriptional activity within the rat PD plaque. Expression of the reporter β-galactosidase, measured by luminometry in tissue extracts from areas at and around the plaque, was considerably intensified in comparison to the control TA (Vernet et al., 2002). This suggests that the reduction in NO by L-NIL inhibition of iNOS, directly or indirectly, activates pro-fibrotic factors such as ROS to further activate the collagen I promoter.

Example 3

The Inhibition of PDE Activity In Vivo Reduces Collagen Deposition and Intensifies Fibroblast Apoptosis in the PD-Like Plaque in the Animal Model Numerous studies have documented that increasing the levels of cGMP by inhibition of PDE enzymes, either with non-specific PDE inhibitors, such as pentoxifylline (Corbin and Francis, 1999; Uckert et al., 2001; Fischer et al., 2001; Desmouliere et al., 1999; Kremer et al., 1999), or specific isoform inhibitors for PDE-5 such as exisulind (Chan et al., 2002; Takuma et al., 2001), can inhibit collagen synthesis and fibrosis and can induce apoptosis in vivo and in cultured cells (Chiche et al., 1998; Pandey et al., 2000; Tao et al., 1999; Loweth et al., 1997; Sirotkin et al., 2000; Taimor et al., 2000; Schade et al., 2002; Horio et al., 1999; Thompson et al., 2000). Thus, elevating cGMP levels may be able to inhibit tunical plaque formation. A study was performed to determine whether the antifibrotic effects of NO in human and rat PD may be at least partially mediated by the elevation of its downstream product, cGMP.

Pentoxifylline (a non-specific, generalized PDE inhibitor), and sildenafil (specific PDE-5 inhibitor) were given orally to the rat in their drinking water (100 mg/l for each PDE inhibitor) for 45 days following TGF-β1 injection to initiate the plaque in the rat model. FIG. 2A, bottom panels shows that, as assessed by Masson staining in terms of collagen fiber/cell-lacunae area ratio, and width of the tunica (not shown), there was considerable reduction in plaque size induced by the PDE inhibitors. This was accompanied by an intensification of the apoptotic index, especially for pentoxifylline (FIG. 3A, bottom panels). The finding that pentoxifylline is more effective than sildenafil in inducing apoptosis may be due to a number of possible mechanisms. Since pentoxifylline inhibits multiple PDE isoforms, it may suggest that other PDEs besides PDE5 may play a role in elevating cGMP levels within the TA that will lead to apoptosis of cells within the plaque. Additionally, PDE inhibitors may act differentially on the three processes that ultimately would inhibit fibrosis development, namely myofibroblast apoptosis, collagen synthesis, and collagen degradation. Although we have not identified the cells undergoing apoptosis, it is likely that they are fibroblasts/myofibroblasts, because those are the predominant cellular component of the rat TA, and because of the direct demonstration of the effects of these treatments on cultures of human fibroblasts and myofibroblasts (see below).

Example 4

Figure 4:
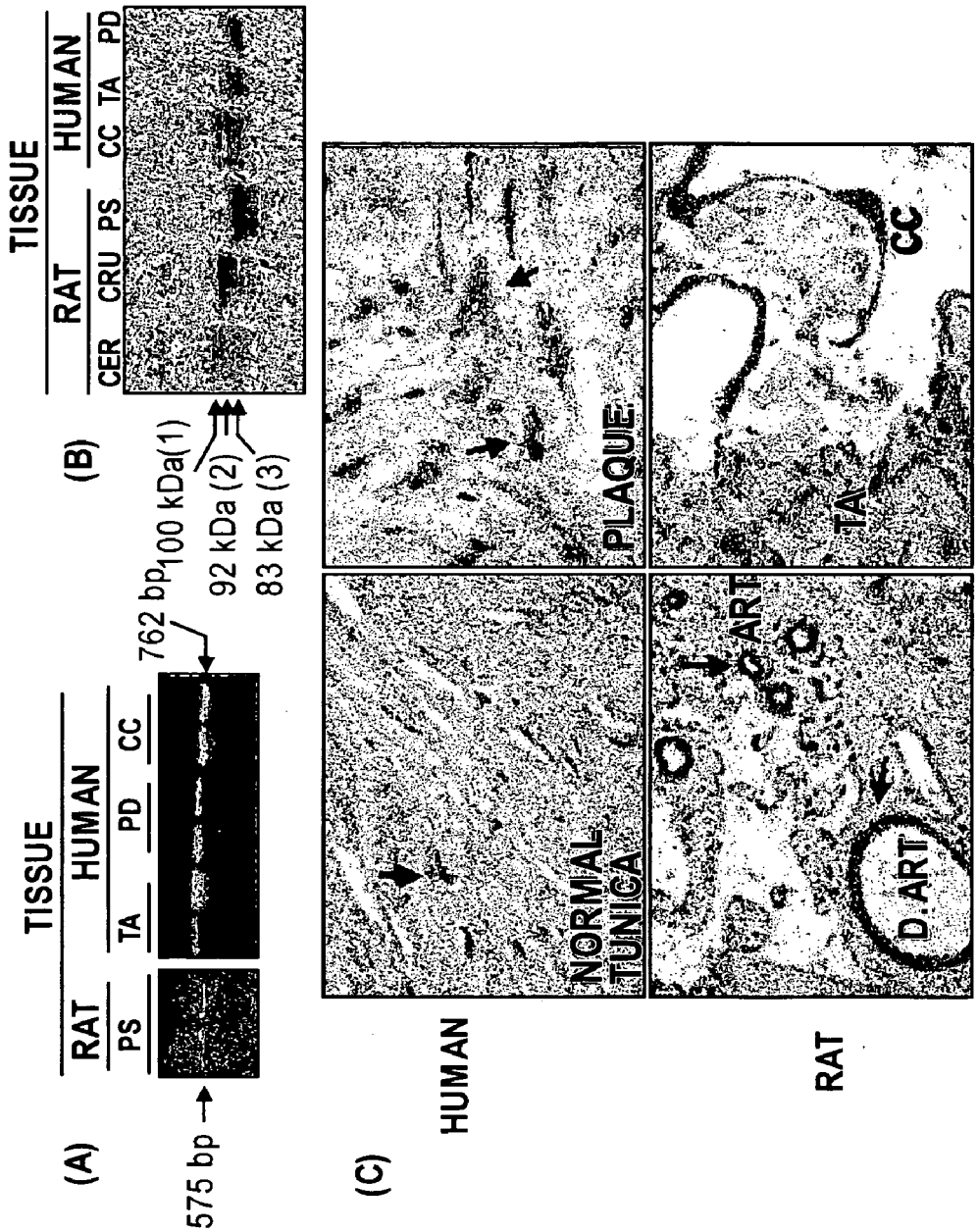
FIG. 4. Expression of PDE-5 mRNA and protein in the human PD plaque and normal tunica albuginea, and their homologous tissues in the TGF-β1 rat model of PD. (A) Ethidium bromide-stained DNA bands obtained by RT/PCR from RNAs isolated from the respective tissues, and fractionated on agarose gels. (B) Luminol-stained protein bands obtained by western blot on polyacrylamide gels. PS: penile shaft; TA: tunica albuginea; PD: Peyronie's disease; CC: corpora cavernosa; CER: cerebellum; CRU: penile crura. (C) Microphotgraphs (200×) of sections from human and untreated rat tissues. D.ART: dorsal artery; ART: artery. Arrows show positive cells for PDE-5.

Presence of PDE5 in the Human Penile Tunica Albuginea and PD Plaque, in the Rat Tunica Albuginea, and in Fibroblasts Cultured From These Tissues As an initial assessment of PDE isoforms expressed in the TA, RT-PCR was performed on splice products of PDE5A (Kim et al., 2000). The observed effects of sildenafil (specific PDE5 inhibitor) and to a partial extent pentoxifylline (has some PDE5 inhibitor activity) are probably mediated by the PDE5A isoform. RT/PCR with primers common to the 3 PDE5A variants (Uckert et al., 2001; Lin et al., 2000a, 2002a) have shown that this enzyme is expressed in both human TA and PD tissues, as well as control tissue, the corpora cavernosa (FIG. 4A). FIG. 4A shows the ethidium bromide staining of PCR DNA fragments from reactions carried out in duplicate and fractionated by agarose gel electrophoresis. The 575 bp PDE5A DNA band was generated as expected from the rat penile shaft (PS) and the 762 bp from the human corpora cavernosa (CC) RNAs, and was amplified to a similar level in total RNA from the human TA and PD. No RNA was extracted from the normal TA and the TGF-β1-induced PD-like plaque in the rat, due to the difficulty in dissecting large amounts of tissue to avoid contamination by cavernosal smooth muscle.

PDE5A expression was confirmed at the protein level by western blot assays of tissue extracts, as shown by the luminol-stained protein bands (FIG. 4B), that can discriminate the three splicing variant proteins of PDE5A designated as 1, 2, and 3 with respective apparent sizes of 100, 92, and 83 kDa, respectively (Lin et al., 2000a, 2002a). The three variants were detected as expected in the rat cerebellum (CER), our control tissue, whereas in the rat penile crura (CRU) and shaft (PS), the predominant forms were the 1 and 3, respectively, with only traces of variant 2 in the crura, and a band smaller than the 3 variant in the penile shaft. This PDE5A-3 variant, accompanied by smaller amounts of the 2 variant, was also expressed in the human corpora cavernosa (CC), and in the TA and PD plaque. Some PDE5A-1 variant was also detected in the human CC.

Immunohistochemistry in human PD and TA sections confirmed the expression of PDE5 in both tissues, at a higher level in PD. In the rat, it is extremely difficult to isolate pure TA and PD-like tissue totally free from corpora cavernosa cells. Therefore, the whole rat penile shaft, comprised of both TA and corpora cavernosa was assayed. Immunocytochemical detection with an antibody detecting all three variants of PDE5A revealed that it was expressed in discrete cells interspersed among collagen fibers in the normal human TA and the PD plaque (FIG. 4C, upper panels). PDE5A was also detected in the media of the of the dorsal artery and those within the corpora cavernosa, and in both the corporal smooth muscle and TA of the penis (FIG. 4C, lower panels).

Figure 7:
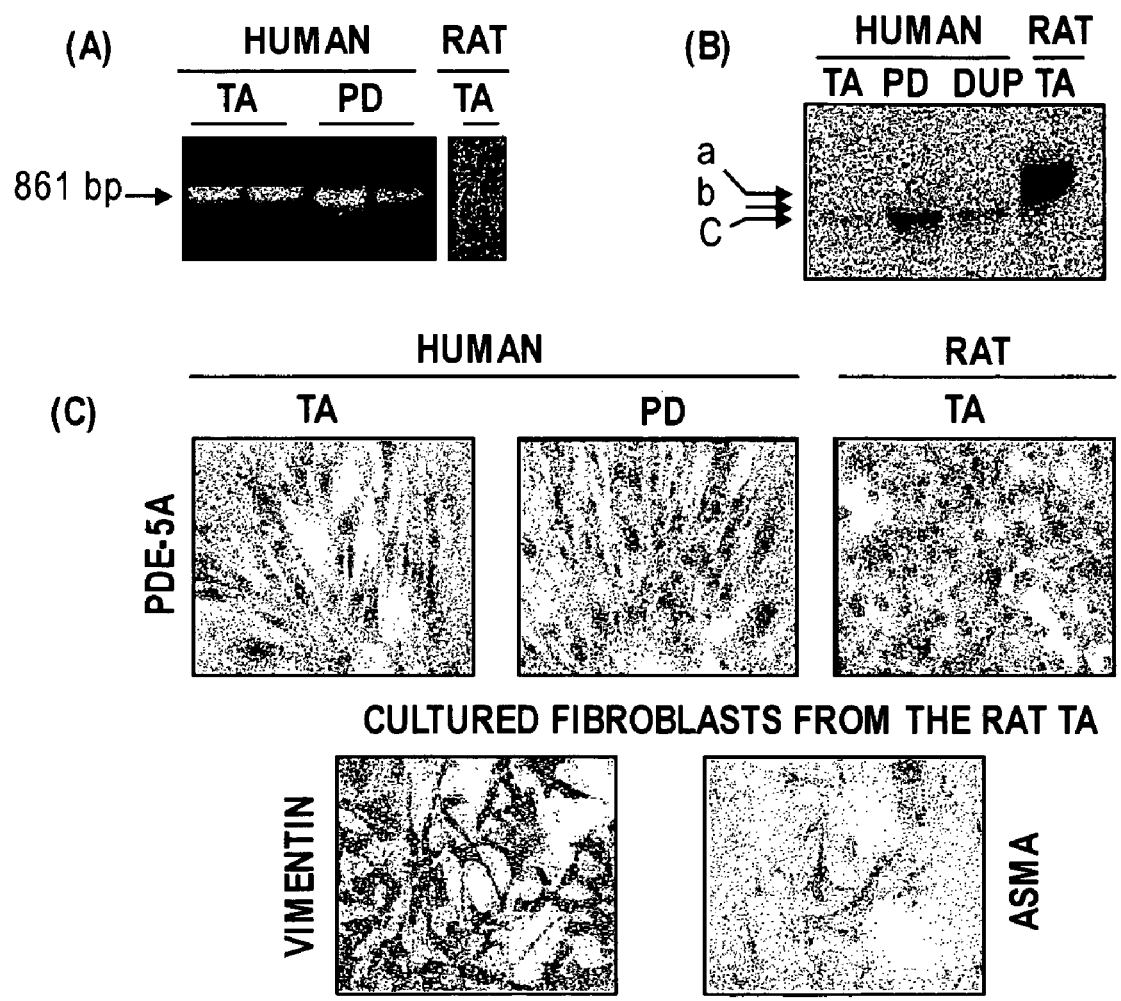
FIG. 7. Expression of PDE-5 mRNA and protein in fibroblast cultures from human PD plaque and human and rat normal tunica albuginea. (A) Ethidium bromide staining of PDE-5A cDNA bands generated from cell RNA by RT-PCR and fractionated on agarose gels. (B) Luminol detection of PDE-5 protein bands obtained by western blot of cell extracts on PAGE. Arrows indicate PDE-5A variants. DUP: cells from Dupuytren's nodules. (C) Microphotographs (200×) of cell cultures stained with the indicated antibodies and counterstained with Meyer haematoxylin FIG. 8. Gene transfer to the tunica albuginea of plasmid and adenoviral cDNA constructs facilitated by electroporation. Both the pCMV-βgal and the AdV-CMV-βgal constructs were injected into the tunica albuginea of the rat, followed by electroporation, and 10 days later rats were sacrificed and frozen fixed tissue sections were stained with X-gal, and counterstained with neutral red. TA: tunica albuginea. (200× magnification).

PDE5 mRNA was also identified by RT/PCR in the fibroblasts cultured from the human normal TA and PD plaque, and from the rat TA (FIG. 7A), and the respective protein was detected by western blot in the human cells as a single PDE5A-3 variant, which agrees with what was observed in vivo in the TA and PD plaque, (FIG. 7B). The rat TA fibroblasts also express the 3 variant, accompanied by equal amounts of the 1 variant, despite the latter larger variant was not detected in the rat penile shaft. Immunocytochemical detection (FIG. 4C, upper panels) confirmed the expression of PDE5A in the three types of cells, namely fibroblasts from the human normal TA and PD plaque, and from the rat normal TA. However, in the latter case, as opposed to the human cell cultures derived from tissues reasonably free from contamination by cavernosal smooth muscle, the rat fibroblasts were obtained from whole corpora cavernosa including the smooth muscle. By successive passages in fibroblast culture medium (Smith et al., 2002), rather pure fibroblast cultures were selected, as evidenced from vimentin staining, and some were myofibroblasts, as seen with ASMA staining (FIG. 7A, bottom panels).

Example 5

Figure 12:
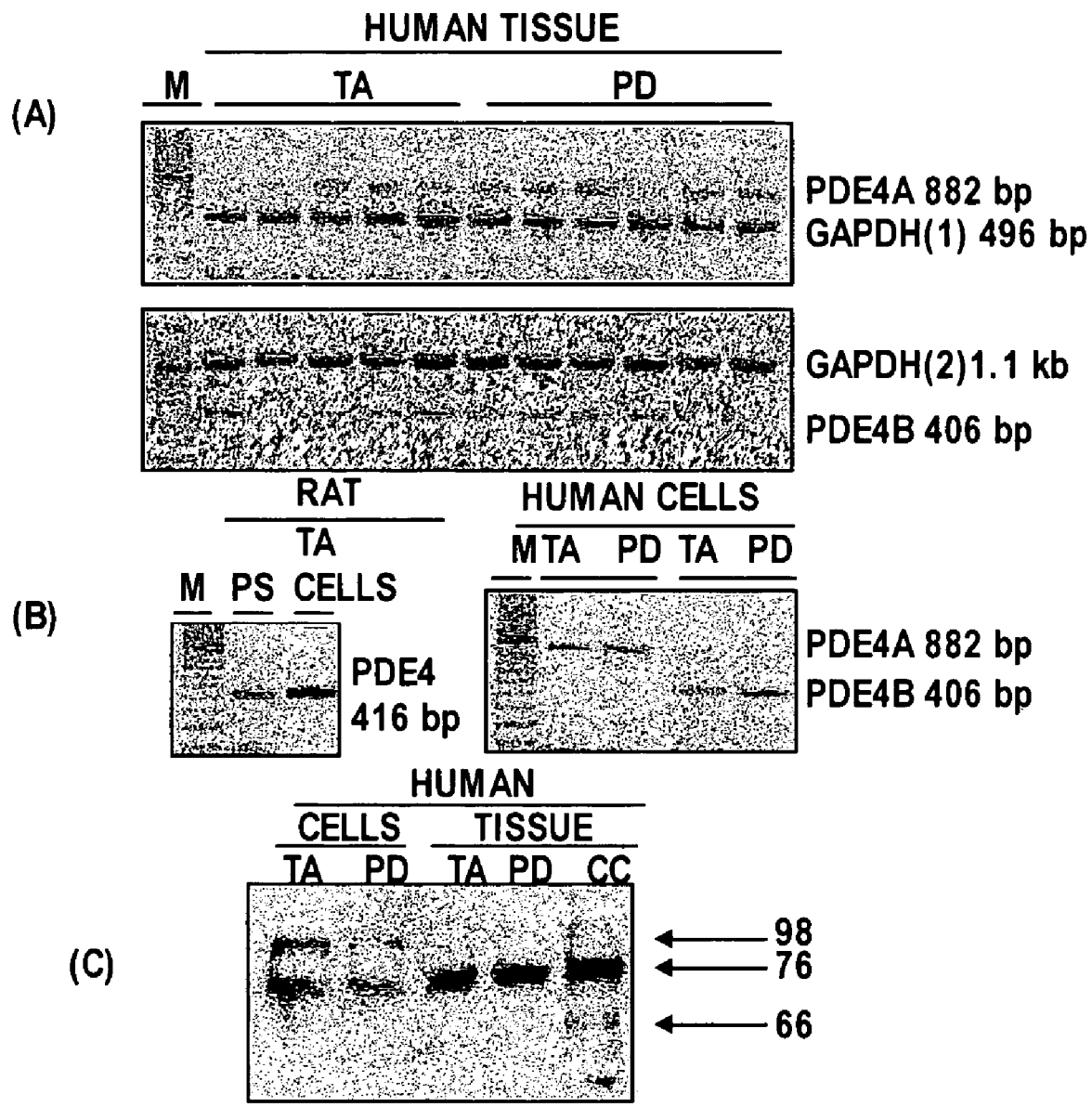
FIG. 12. Expression of PDE-4 mRNA and protein in the human PD plaque and normal tunica albuginea, and their homologous tissues in the TGF-β1 rat model of PD, and in fibroblasts cultured from these tissues. (A) Ethidium bromide staining of DNA generated from PD and normal human TA tissue by RT/PCR with primers for PDE4A, PDE4B, and GAPDH (reference gene), separated by agarose gel electrophoresis. (B) PDE4 mRNA in rat penile shaft (PS), rat TA cells, or human TA or PD cells. TA: tunica albuginea; PD: Peyronie's disease; CC: corpora cavernosa smooth muscle; PS: penile shaft. (C) Luminol-stained protein bands on western blots of human tissue and cell extracts with the antibody against PDE4A.

Presence of PDE4 Variants in the Human Penile Tunica Albuginea and PD Plaque, in the Rat Tunica Albuginea, and in Fibroblasts Cultured From These Tissues PDE4 mRNA Studies Since the cAMP-dependent PDE inhibitor, pentoxifylline, has been used previously as an antifibrotic compound (Lee et al., 1997; Becker et al., 2001; Raetsch et al., 2002), we investigated by RT/PCR whether PDE4 is expressed in the TA and PD tissues and the respective cell cultures, utilizing primers for two (A and B) of the three variants. FIG. 12A shows that PDE4A and B mRNAs are expressed in the human normal TA and in the PD tissue. Both variants were also detected in human corpora cavernosa tissue containing mainly smooth muscle (not shown). Confirming these results, PDE4A and B mRNAs were also found in the fibroblasts cultured from human TA and PD (FIG. 12B). In the case of the rat, PDE4 mRNA (without variant discrimination) was detected in the TA cells, and to a lesser degree in the penile shaft tissue, thus suggesting that PDE4 in the rat TA fibroblast cultures does not arise from contamination with smooth muscle, which in any case had been reasonably excluded above by immunocytochemistry.

PDE4 Western Blots

Confirmation of the expression of PDE4A at the protein level was obtained by western blot with an antibody for the different variants, in extracts from the human cultured cells used for the identification of PDE4A in TA and PD plaque. FIG. 12C shows an intense 76 kDa band that would correspond to a variant identified in testis (Salanova et al., 1999), as well as a minor 102 kDa band for the so-called PDE4Ax, also seen in the testis. The 76 kDa protein is very intense in the three human tissues: TA, PD plaque, and corpora cavernosa, but the 102 kDa band was virtually not detected. No PDE4B could be visualized when the western blot membranes were stripped and reacted with an antibody specific for this isoform (not shown).

PDE4 Immunohistochemistry

Figure 13:
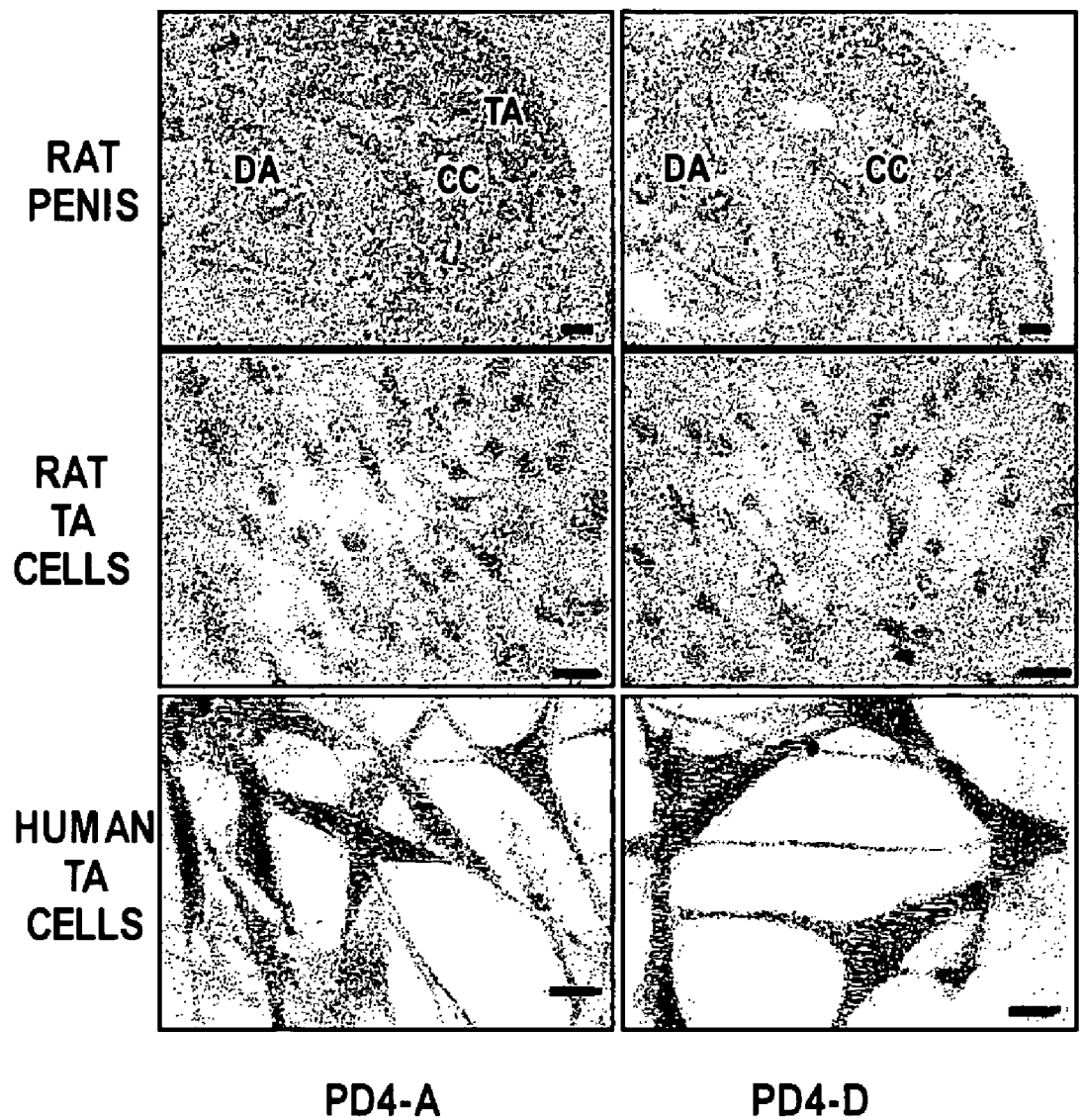
FIG. 13. Immunodetection of PDE-4 protein in the rat penis and cultures of rat and human tunica albuginea fibroblasts. Microphotographies of tissue sections (top panels) or cell cultures (middle and bottom panels), as indicated, submitted to immunodetection with antibodies against PDE4A or PDE4D, and counterstained with Meyer haematoxylin.

Immunodetection with the PDE4A antibody identified cells all along the internal side of the TA, as well as in the corpora cavernosa smooth muscle, expressing PDE4A (FIG. 13, top). An antibody specific for PDE4D also showed cells reactive for this isoform, evidencing that both PDE4 genes are expressed in the TA and corpora cavernosa (FIG. 13, top). A similar situation is seen in the rat TA fibroblasts in culture, with considerable expression of PDE4A in most cells, whereas only a fraction of the cells express PDE4D (FIG. 13, middle). In contrast, most of the human TA fibroblasts were intensively stained with antibodies against the A and D isoforms (FIG. 13, bottom). Despite the fact that the PDE4B mRNA was identified by RT/PCR (see FIG. 12), virtually no protein reactivity for this isoform was observed by imunodetection in tissue sections or cell cultures (not shown). A similar situation occurred with one of the variants of PDE4A (PDE4A4), utilizing a specific antibody, different from the general used above for PDE4A that according to the supplier does not detect variant 4.

Example 6

Incubation of PD Fibroblast Cultures With PDE Inhibitors or a cGMP Analog Reduces Collagen I Synthesis and Myofibroblast Differentiation, and Increases Apoptosis Verification that the PDE5A and PDE4 proteins detected in the TA and PD cells and tissues are enzymatically active was obtained by measuring the levels of cGMP in cell extracts of the PD fibroblast cultures, with a basal mean value+/−SEM of 5.0+/−0.4 pmol/mg protein (n=5) in the absence of additions. Levels of cGMP increased 5.0-fold with 100 uM SNAP (an NO donor) for 3 days, with fresh daily replacement of medium with SNAP. A cGMP analog able to enter the cell, 8 Br-cGMP, at 10 uM, was also able to increase cGMP levels by 6.4-fold, and with 100 µM 8 Br-cGMP, the levels of cGMP were dramatically elevated by 38.7-fold. The basal levels of cAMP were 42.6+/−12.7 pmol/mg protein in the absence of SNAP and did not vary significantly when measured after 3 days with SNAP.

Figure 14:
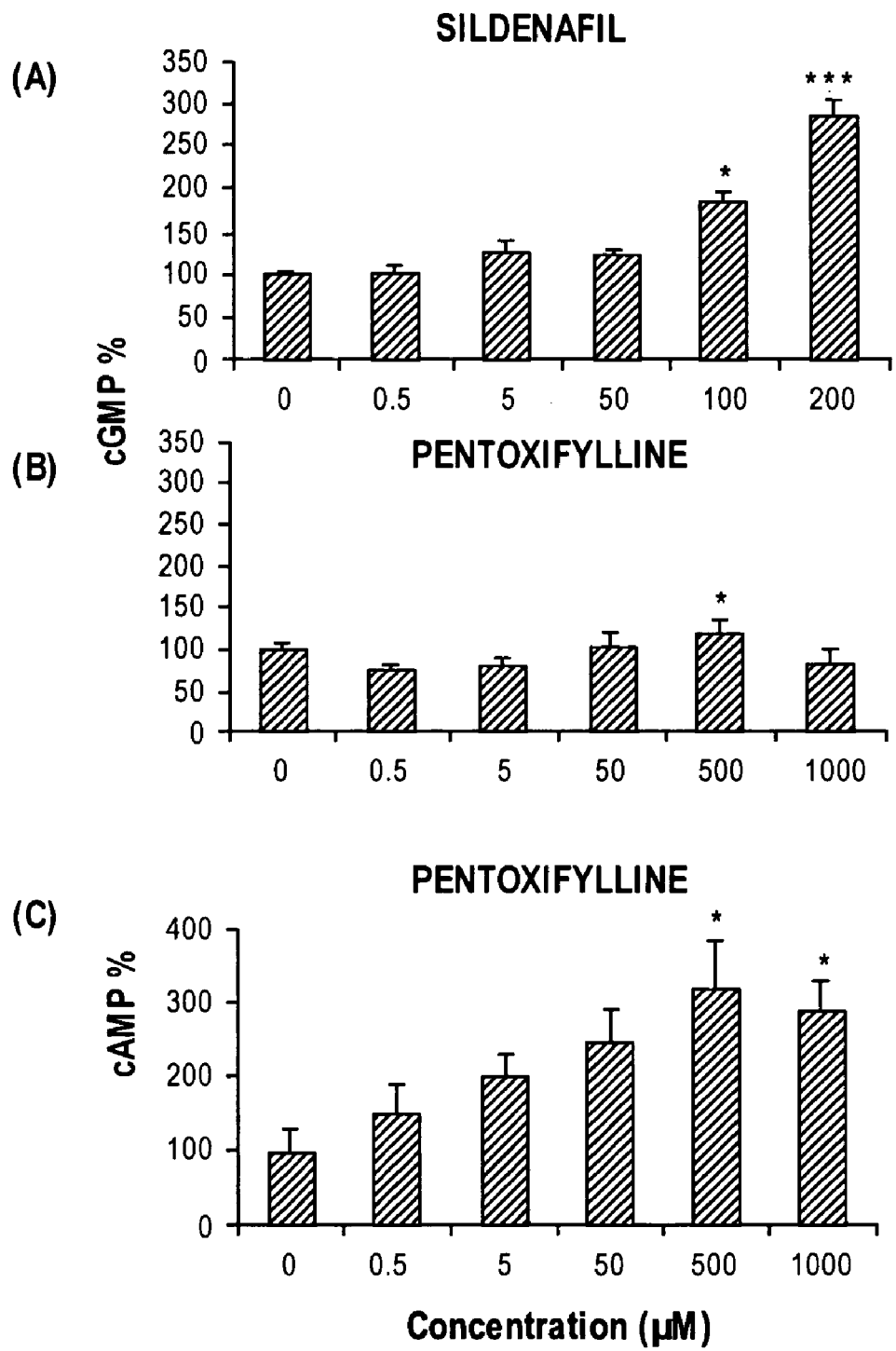
FIG. 14. Effect of pentoxifylline and sildenafil on cAMP and cGMP levels in fibroblast cultures from human PD plaque, estimated by enzyme immunoassays. Cells were incubated for 3 days in fibroblast growth medium (FGM)/10% fetal bovine serum, in the presence of SNAP (100 uM; medium changed daily) added 4 hs prior to the PDE inhibitors, and increasing concentrations of sildenafil or pentoxifylline. cGMP and cAMP levels were measured in cell homogenates. Results are the means of 2 separate experiments conducted in triplicate. (A) cGMP levels in the presence of sildenafil. (B) cGMP levels in the presence of pentoxifylline. (C) cAMP levels in the presence of pentoxifylline.

The cGMP-dependent PDE5 inhibitor sildenafil did not significantly stimulate cGMP levels in the absence of SNAP (not shown). However, in the presence of the NO donor, the cGMP levels expressed as % of the basal control levels in the absence of sildenafil, were increased dose-dependently by sildenafil after the 3-day incubation, as expected (FIG. 14A). When cells were incubated with this NO donor, increasing concentrations of pentoxifylline, also as expected, did not increase significantly cGMP levels expressed as % of control levels (FIG. 14B), but were very effective in increasing cAMP levels (FIG. 14C), thus confirming its role as a cAMP-dependent PDE inhibitor with little or no effect on cGMP-dependent PDE.

In order to determine whether the PDE inhibitors may reduce collagen synthesis, the PD cells were incubated with or without the drugs at lower concentrations: pentoxifylline at 200 nM, and sildenafil, at 50 and 200 nM. After 3 days, cells were fixed and the intracellular deposition of collagen I and III was determined by immunocytochemistry with specific antibodies against the two isoforms. The antibody against collagen I elicited an intense granular and perinuclear staining (not shown). In contrast, collagen III was detected in only in about 30% of the cells, and stained more diffusely and rather lightly, even when cells where treated with TGF-β1 (10 ng/ml), a known stimulator of collagen III synthesis (FIG. 5B).

Quantitation by image analysis (FIG. 5A) in the cultured human PD fibroblasts indicated that in the absence of additions, most of the cells (100%) expressed collagen I, and that both pentoxifylline and sildenafil at 200 nM completely inhibited collagen synthesis in a small number of cells (5-15% of the total, FIG. 5A top), and significantly reduced (30-40% decrease) the average intensity of expression per cell (FIG. 5A, bottom). In contrast, the PDE inhibitors did not decrease, but even increased, the synthesis of collagen III (not shown). More drastically than in the case of collagen I, both of the PDE inhibitors (pentoxifylline and sildenafil) significantly reduced the number of ASMA positive cells (myofibroblasts) from 37% in the control to about 24%. The average ASMA expression per cell was significantly reduced by the PDE inhibitors by more than 90% in all cases.

Figure 6:
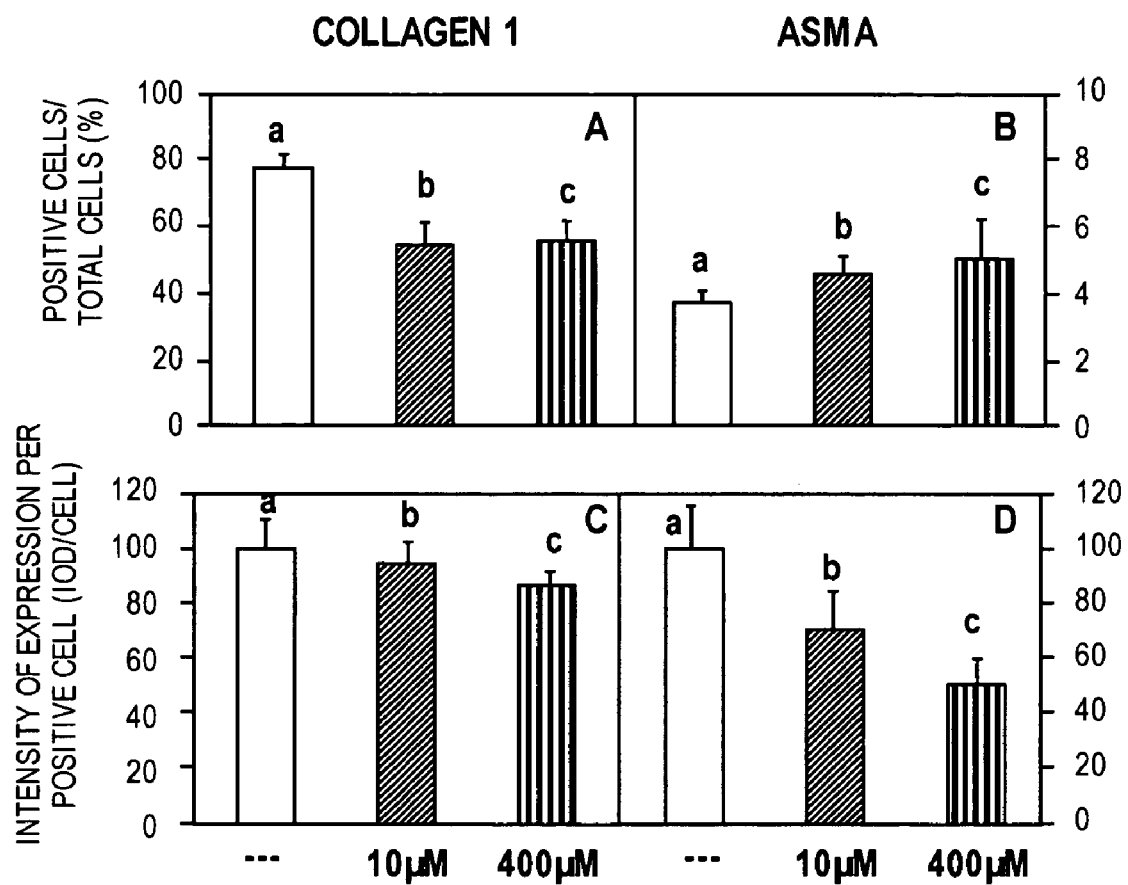
FIG. 6. Effects on collagen I synthesis and myofibroblast differentiation in fibroblast cultures from the human PD plaque by a cGMP analog (8-Br cGMP), estimated by immunocytochemistry. Cells were incubated for 3 days with the indicated concentration and collagen I and ASMA were immuno-cytochenmically detected. Values are means+/−SEM for three separate incubations. p<0.05 were as follows: panel A: a vs b,c; panel D: a vs c; all others were non-significant.

To show that in the case of sildenafil some of the effects are mediated by the elevation of cGMP, the PD fibroblasts were then incubated for 3 days with 8-Br-cGMP, and a significant (30%) reduction in the number of cells expressing collagen I was obtained at 10 µM 8 Br-cGMP (FIG. 6), although a higher concentration (400 µM) did not induce further decrease (FIG. 6). In contrast to the effects of the PDE inhibitors observed in the previous experiments, collagen I expression per cell was reduced only moderately and non-significantly by the cGMP analog. The differentiation of fibroblasts into myofibroblasts measured by the level of ASMA expression per cell was decreased significantly by 400 µM 8 Br-cGMP, as in the case of the PDE inhibitors, but there was no effect on the relative number of positive cells (FIG. 6).

Figure 21:
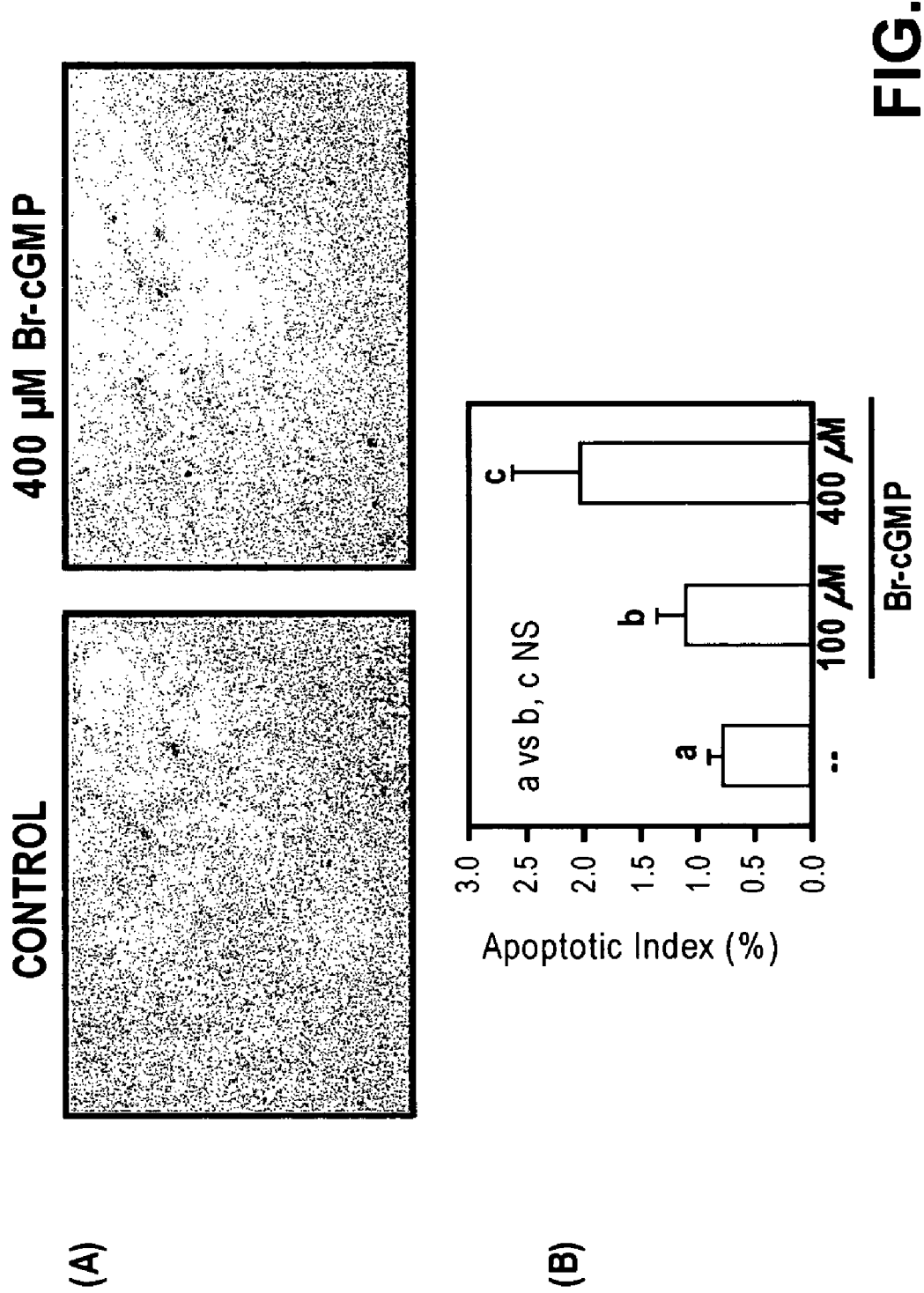
FIG. 21. Effect of 8 Br-cGMP on apoptosis in fibroblasts from human cultured PD plaque, estimated by TUNEL. (A) Microphotographs (200×) of apoptotic cells in incubations receiving no addition and 400 uM 8 Br-cGMP for 3 days. (B) Apoptotic index, as means+/−SEM for three separate incubations. a vs b,c $p>0.05$.

The increase of cGMP in the PD cells incubated with 8 Br-cGMP leads to a stimulation of apoptosis, as shown by an increase in apoptotic bodies detected with the TUNEL technique (FIG. 21A). However, because of variability between experiments, the considerable 2.3 fold-increase measured by image analysis did not achieve statistical significance (FIG. 21B).

Example 7

Increase in NO Levels in Fibroblast Cultures From Human Normal TA and PD Leads to Peroxynitrite Formation, Fibroblast Apoptosis, and Reduction of Intracellular Collagen We have developed primary cell cultures from human normal TA and PD plaque, obtained from different patients, that were dissected to avoid contamination with corporal smooth muscle. These cultures contain fibroblasts and some myofibroblasts, as shown by a 100% immuno-reactivity with a vimentin antibody (Vernet et al., 2002) and represent the main cellular component of the original tissues.

Figure 5:
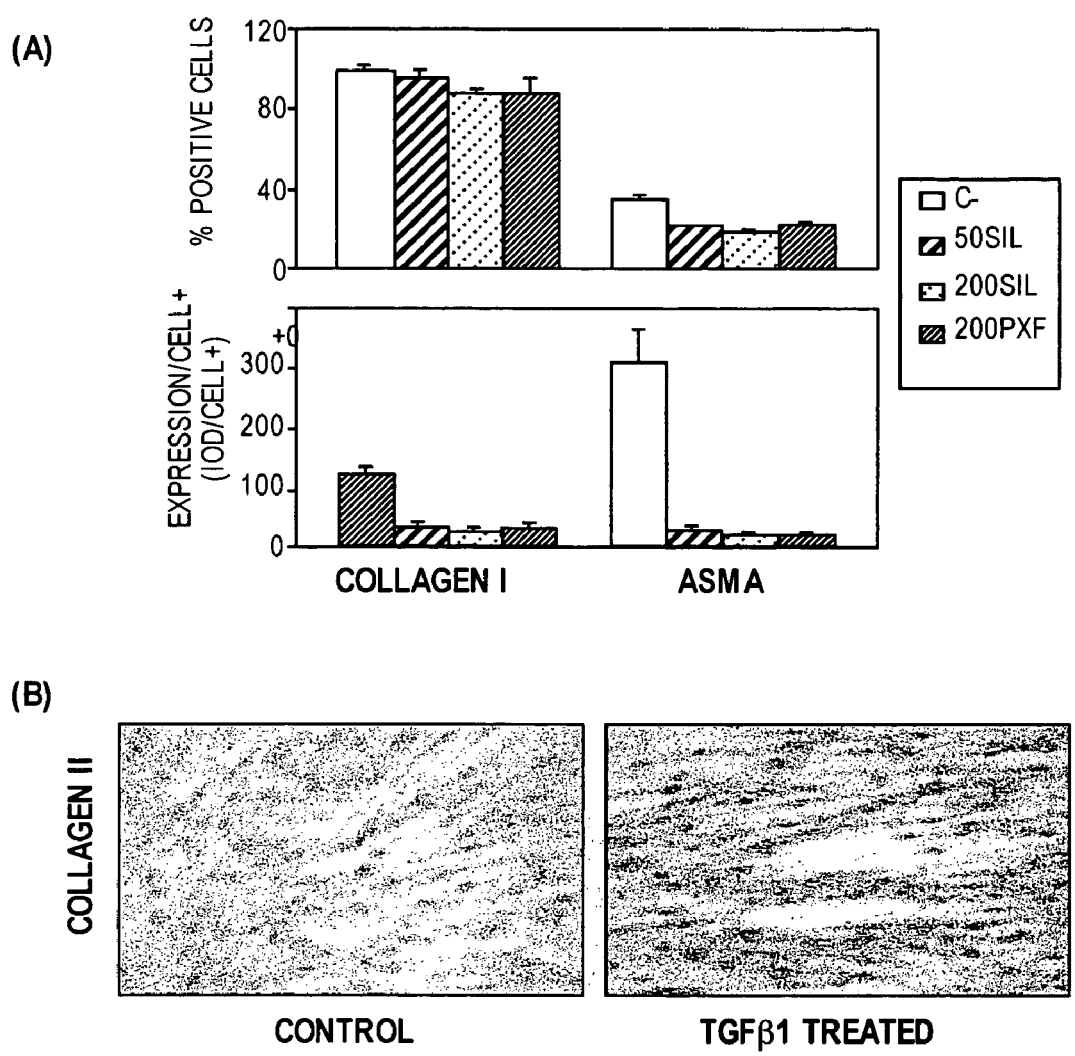
FIG. 5. Inhibition of collagen I synthesis and myofibroblast differentiation by PDE inhibitors in fibroblast cultures from a human PD plaque. (A) QIA evaluation of collagen I and ASMA expression. Control (C) no addition; 50SIL: sildenafil (50 nM); 200SIL: sildenafil (200 nM); 200PXF: pentoxifylline (200 nM). (B) DAB-stained immunocytochemical detection of collagen III in PD cells incubated for 3 days in DME-serum free medium in the presence or absence of 5 ng/ml of TGF-β1 (200×).

The main features of these cultures, demonstrated by QIA immunocytochemistry, are: 1) a substantial morphological difference between the TA and PD plaque cells (Vernet et al., 2002), that corresponds to the observations in vivo. PD cells change from small, more spindle shaped cells to much bigger, polygonal cells with bigger nuclei and expansions, and in certain cases typical "stellate" appearance whereas TA cells do not substantially change in morphology. 2) These fibroblasts, particularly those of PD origin, are able to differentiate into vimentin+/ASMA+ myofibroblasts comprising about 30% of the cells in culture (Vernet et al., 2002), and this percentage of myofibroblasts is also seen in vivo in the plaque (Vernet et al., 2002). 3) The cultures can be induced to express iNOS, synthesize collagen I, and undergo apoptosis both in vitro and in vivo (Vernet et al., 2002). 4) Their responses to different agents, specifically the inhibitory action of an NO donor, SNAP, on a) collagen I synthesis in all the cells, and b) myofibroblast differentiation (Vernet et al., 2002), and their response to PDE inhibitors in cell culture (FIG. 5) resemble the responses observed in vivo in the animal model of PD treated with NO donors or PDE inhibitors (FIG. 3). 5) Collagen III, is also synthesized but to a lower extent than collagen I and is not significantly affected by NO or PDE inhibitors (FIG. 5).

The use of an NO donor SNAP or iNOS induction with a cytokine cocktail increased intracellular NO reduced fibroblast numbers in both normal human TA and PD cultures (Vernet et al., 2002). This process is associated with the production of peroxynitrite, as evidenced by nitrotyrosine formation (not shown) and resembles the increase in apoptosis seen in vivo after sildenafil and pentoxifylline treatments.

Example 8

The Increase in cGMP Levels in Fibroblast Cultures Leads to Fibroblast Apoptosis and the Reduction in Intracellular Collagen I To verify that the effects of pentoxifylline and sildenafil described above were due to an elevation in cGMP levels, we incubated human PD cells with a stable cGMP analog able to traverse the cell membrane, 8-BrcGMP. This compound (with levels as low as 10 uM) inhibited collagen I production by the cells (FIG. 6), and increased apoptosis, as determined by TUNEL (Ferrini et al., 2001a; Vernet et al., 1998), from 7.5+/−0.4 (control) to 20.5+/−1.1 (100 uM 8-BrcGMP) cells per field. The intracellular cGMP levels increased from 0.02 to 1.83 nmoles/$10^6$ cells with 100 uM 8-BrcGMP in control vs. treated cells, respectively.

The effects of the PDE inhibitors, as seen in in vivo experiments, are most likely mediated in part by PDE-5, as shown by the presence of PDE5A mRNA (FIG. 7A), and specifically, the PDE5A-3 protein variant as in the in vivo derived tissues (FIG. 7B), in both the human TA and human PD derived cells. The fibroblast cultures obtained from the rat TA express all three PDE-5 variants. All human and/or rat cell cultures of normal TA and PD tissues were PDE5 positive by immunocytochemistry (FIG. 7C, top panels). Cells derived from human TA tissue were clearly fibroblasts with some myofibroblast differentiation, as assayed with vimentin and ASMA markers (FIG. 7C, bottom panels).

Example 9

ROS Levels are Increased in the Human and Rat PD-Like Plaque Tissues and are Reduced by NO ROS plays an important role in the development and maintenance of many fibrotic disorders including PD, by stimulating collagen synthesis (Poli, 2000; Curtin et al., 2002; Cattell, 2002; Kim et al., 2001; Fan et al., 2000; Higuchi et al., 1999). Therefore, the interplay and reactivity of ROS with NO may be an important therapeutic target. We have previously shown that heme-oxygenase I immunoreactivity, a marker for the strong pro-fibrotic factor ROS, is increased in the PD plaque in comparison to normal TA in the human and the TGF-β1 rat model of PD (Ferrini et al., 2002). Additionally, when iNOS activity was blocked with L-NIL in the TGF-β1 rat model, there was a considerable elevation of ROS levels (Ferrini et al., 2002). The same inverse correlation between NO and ROS was observed utilizing superoxide dismutase immunodetection, which measures the antioxidative response in both human and PD tissue and in human fibroblast cultures (not shown). This reduction in the NO/ROS ratio is associated with a considerable stimulation of collagen deposition and collagen synthesis (Ferrini et al., 2002).

Example 10

Use of Gene Transfer and Reporter Gene Expression for Analyzing PD

Several of the therapeutic approaches disclosed herein are based on gene transfer of cDNA constructs to the penile TA (e.g., iNOS, PKG). Therapeutic administration of recombinant cDNA may lead to an elevated expression of the corresponding anti-fibrotic protein. In the case of the penis, we have utilized plasmid and adenoviral constructs of iNOS and penile nNOS (PnNOS) (Magee et al., 2002a), including the use of plasmid and adenoviral constructs expressing β-galactosidase as a reporter gene, and electroporation to enhance viral and plasmid uptake during transfection (Magee et al., 2002a).

Figure 8:
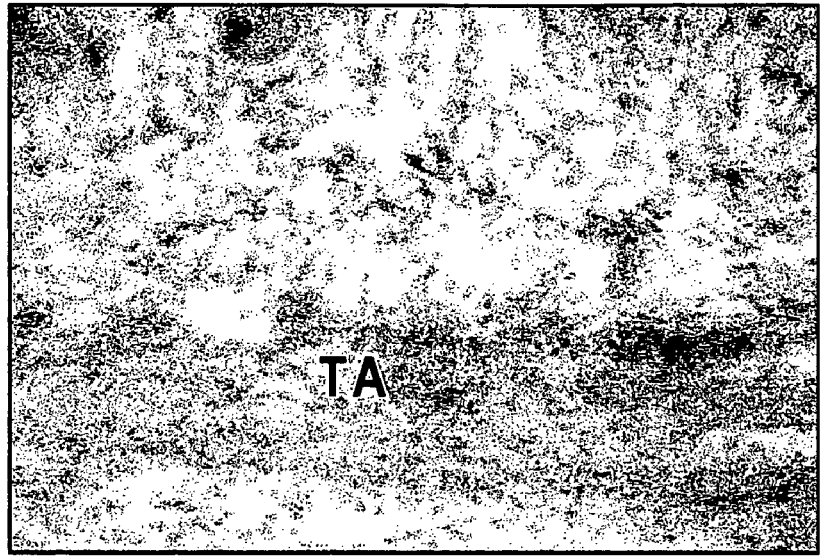
Figure 8:
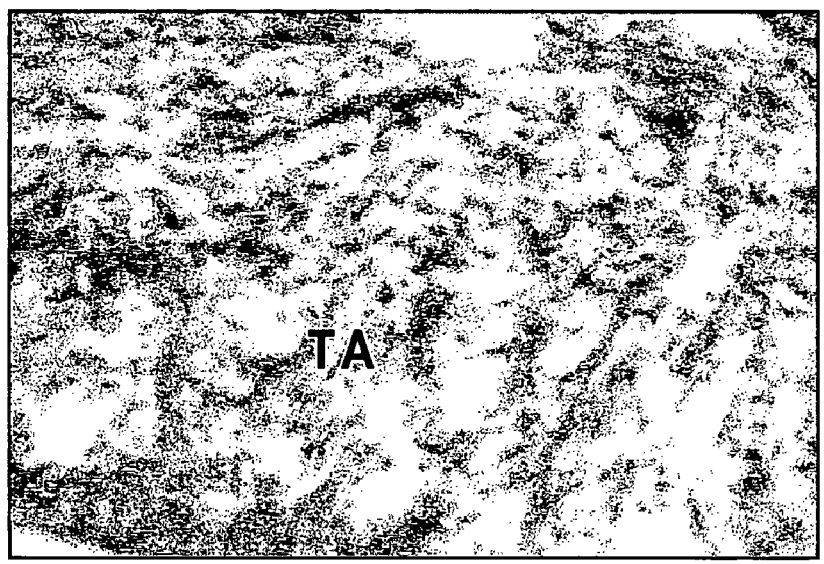

Such constructs can penetrate and spread into the TA, as shown by X-gal staining (FIG. 8) suggesting that the direct injection to the TA with and without electroporation is feasible for targeting genes to the TA for arresting or reversing the growth and development of the PD plaque.

Example 11

Figure 9:
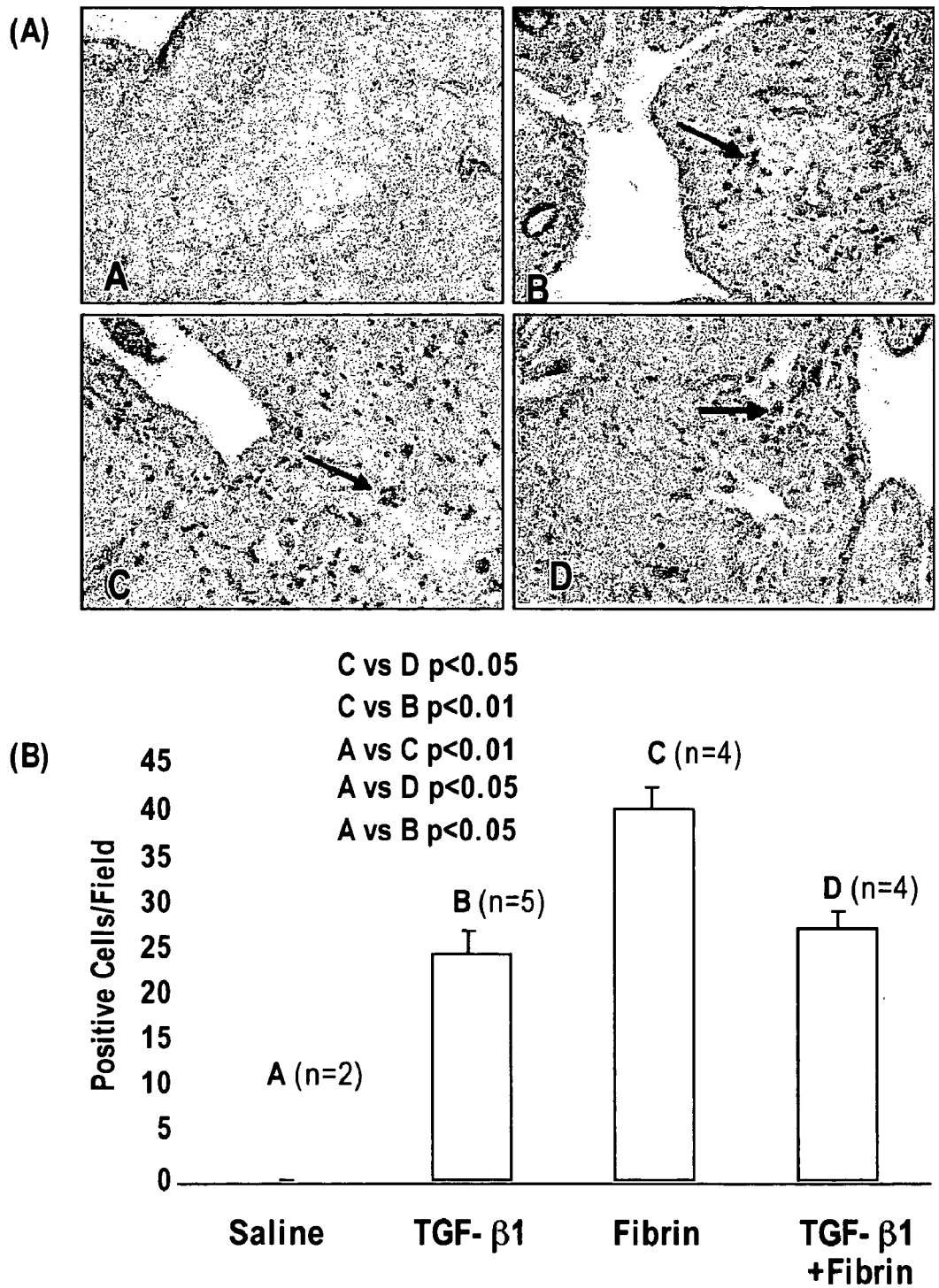
FIG. 9. Induction of TGF-β1 expression in the Peyronie-like plaque induced by fibrin in the tunica albuginea of the rat. (A) Sections adjacent to the ones for plaques shown on FIG. 11 were immunostained with an antibody for TGF-β1. Arrows point to cells with intense staining. (220× magnification) (B) Image quantitation of positive cells in the average field of the fibrotic plaque (n=5). Values are means+/−SEM, and p values are as indicated. (200× magnification)

Confirmation of the Pro-Fibrotic Role of TGF-β1 Expression in Another Model of PD The TGF-β1 rat model for PD is a very valuable tool, and since its introduction in 1997 (El-Sakka et al., 1997b, 1998, 1999), we have been able to study various aspects of the pathophysiology of PD, some of which are presented above. However, in a different experimental design based on the ubiquitous finding of fibrin in histological samples of human PD tissue (not shown), we have recently re-confirmed the importance of TGF-β1 as the main profibrotic factor in eliciting the PD-like plaque in the TA of the rat. We observed considerable expression of this factor in a tunical lesion induced by the injection of a preparation of human fibrin (fibrinogen/thrombin/aprotinin) in the rat TA (FIG. 9). This tunical lesion, caused by fibrin and mediated by TGF-β1, is fully developed at 3 weeks, as visualized by Masson staining, and is indistinguishable from the one caused by the injection of TGF-β1 alone. However, the TGF-β1 model requires 6 weeks to develop, whereas this fibrin induced model only requires 3 weeks to fully develop (not shown). The fibrin induced plaque is accompanied by detection of fibrin in the lesion (similar to what is seen in the human, but absent from the TGF-β1 injected rat model), disorganization of elastin fibers, expression of iNOS and heme-oxygenase I, and an increased level of apoptosis. Save for the presence of fibrin in the TA, all findings are similar to the ones observed in the TGF-β1 injected model (not shown).

Example 12

Figure 10:
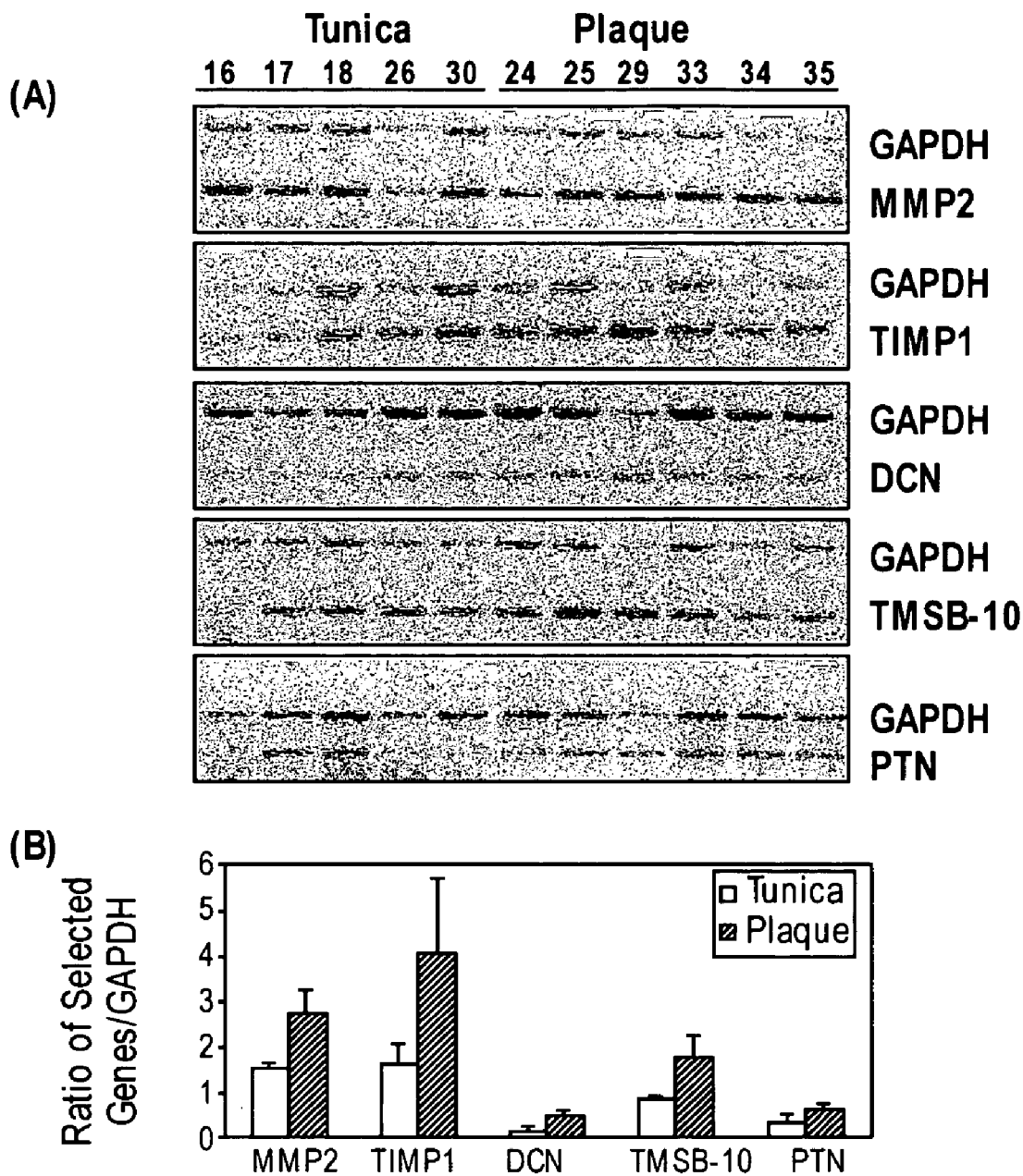
FIG. 10. Confirmation by RT/PCR of alterations in the expression of certain genes in the human Peyronie's plaque as compared to the normal tunica albuginea.

The TA and the PD Plaque are Tissues in Constant Turnover, and Collagenase Inhibition May Play a Role in Collagen Accumulation As disclosed above, collagen synthesis is stimulated in the TGF-β1 animal model of PD, particularly when NO synthesis is partially inhibited by L-NIL. Data obtained by DNA microarray analysis (Clontech) has allowed us to define and compare changes in the profile of multiple gene expressions at the mRNA level in the PD plaque versus normal TA. Data (Table 1), obtained in 9 patients and 9 control subjects indicated that: a) PD, like its related disorder Dupuytren's contracture, is a condition that seems to be in a state of dynamic flux, with alterations in the expression of mRNAs for genes related to collagen turnover and tissue remodeling, extracellular matrix synthesis and degradation, and cell replication and apoptosis. This suggests that the fibrosis of PD is not a terminal event but a dynamic one, and that it is possible to pharmacologically affect its steady state and alter its direction by: a) inhibiting collagen synthesis and/or fibroblast differentiation and replication, since a subset of differentially expressed genes are related to these processes; and/or b) by stimulating collagen breakdown, since there is a considerable increase in the expression of different types of MMPs (e.g. MMP2 and MMP9). The increased expression of MMPs was confirmed in human PD by RT/PCR (FIG. 10).

MMPs may play an important role in extracellular matrix remodeling in the PD plaque. The inhibition of MMP may occur by increased activity of the MMP inhibitors (TIMP). We have verified the increased expression of TIMP in PD tissue using the more sensitive RT/PCR procedure, which showed a 2-fold stimulation of TIMP1. The increased expression of TIMP1 should lead to an increased inhibition of MMP.

Example 13

The Expression of a Family of Wound Healing-Related Peptides, the Thymosins, is Increased in Human PD In the DNA microarray study mentioned above, we found increased expression of peptides belonging to the thymosin-β family (Table 1). These proteins stimulate MMP activity, cross-link to fibrin and collagen, and promote wound healing (Huff et al., 2002; Malinda et al., 1999; Sosne et al., 2002). Their increased synthesis in the PD plaque may be another manifestation of a defense mechanism that is unable to control or arrest the progression of fibrosis. The administration of thymosin-β4 has been proposed for wound healing (Huff et al., 2002; Malinda et al., 1999; Sosne et al., 2002), and, as stated above, PD is likely the result of an injury that does not heal properly. It should be possible to further up-regulate this endogenous defense mechanism by pharmacologically increasing thymosin levels in the TGF-β1-induced lesions in the rat model of PD.

Example 14

Investigating the Role of NO and ROS in PD Using the iNOS Knockout Mouse Model

Figure 11:
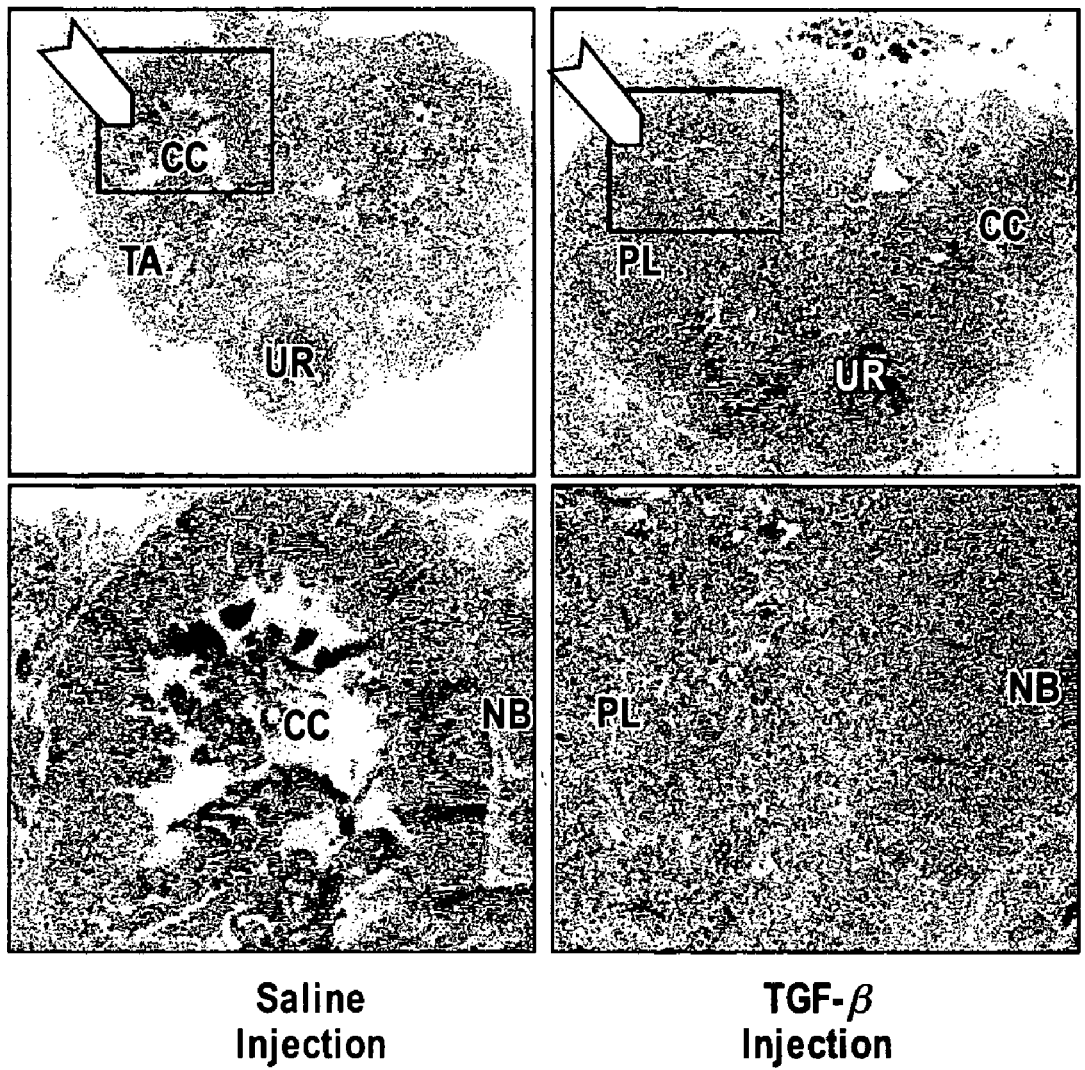
FIG. 11. PD-like plaque similar to the one induced in the rat can be elicited in the tunica albuginea of the mouse by TGF-β1 injection, detected by Masson staining. Low (4×, top); and high (100×, bottom) magnifications of mouse penis injected with saline and TGF-β1. Light arrows show the site of TGF-β1 injection. Boxes represent the area of high magnification. CC corpora cavernosa; UR: urethra; TA: tunica albuginea; Pl: plaque; NB: nerve bundle.

The blockade of iNOS activity in the rat by long-term oral L-NIL administration (Ferrini et al., 2002) is only partially effective in inhibiting iNOS. Therefore, the iNOS knockout mouse (Hochberg et al., 2000) is of use for studies where iNOS expression is completely absent. NO in this animal model can be synthesized only by the other NOS isoforms, namely eNOS and nNOS. These isoforms are in general constitutive and as such are difficult to induce. It therefore seems unlikely that they would play a significant anti-fibrotic role. The iNOS knockout mouse has previously been used to show that experimental urethral fibrosis is intensified as a consequence of the iNOS knockout (Tanaka et al., 2002). We have tested whether it is possible to develop a PD-like plaque by injection of TGF-β1 into the TA, injecting 0.2 ug of TGF-β1 into the TA of a wild type mouse. FIG. 11 shows plaque formation within the TA at 6 weeks as shown with Masson staining.

Example 15

Therapeutic Intervention in PD

The results above demonstrate that PDE5 and 4 are both expressed in the human and rat normal tunica albuginea, and the respective PD and PD-like fibrotic plaques, as well as in the cell cultures obtained from these tissues. The results also demonstrate the inhibition of a TGF-β1-induced fibrotic plaque in the rat model of PD, through the reduction of collagen deposition and possibly an increase in apoptosis of the resident fibroblasts and myofibroblasts, by long-term oral administration of the respective PDE5 and cAMP-dependent PDE inhibitors, sildenafil and pentoxifylline, and the NOS substrate, L-arginine.

The in vitro effects of both PDE inhibitors and a cGMP analog, 8 Br-cGMP, on fibroblast cultures obtained from the human PD plaque, indicate that these agents may be effective against fibrosis by reducing the relative number of fibroblasts/myofibroblasts through the induction of apoptosis of these cells. We also found that these compounds a) interfere with fibroblast differentiation into myofibroblasts, the cells that are key players in tissue fibrosis, and b) down-regulate the synthesis of collagen I but not collagen III. The effects of sildenafil may be exerted through the inhibition of PDE-5, and in the case of pentoxifylline through a cAMP-dependent PDE, potentially PDE4. The results open a new approach for the treatment of PD and, by extension, tissue fibrosis, based on the use of PDE inhibitors and other enhancers of PDK activity, and possibly of compounds and biologicals that enhance NO synthesis.

The reduction of the fibrotic plaque observed in vivo in animals receiving L-arginine, coincides with its effects in preventing experimental ethanol-induced inflammatory and fibrotic changes in liver, kidney, lung, and cardiovascular system (Nanji et al., 2001; Peters et al., 2000; Simko and Simko, 2000; Susic et al., 1999; Song et al., 1998; Bing et al., 2002; Alves et al., 2002). The action of L-arginine may be mediated by the stimulation of NOS activity. This was previously shown by the increase of L-arginine levels in the penis and the improvement of erectile dysfunction in the aging rat by NOS stimulation achieved after a regimen of L-arginine administration of 2.2 g/kg/day (Moody et al., 1997). This dose is within the range normally employed as vasculoprotective for long-term studies in the rat (Bing et al., 2002; Alves et al., 2002).

The in vivo and in vitro results showing an inhibition of collagen synthesis and stimulation of apoptosis in the PD-like plaque and in PD cells by both sildenafil and pentoxifylline, are in good agreement with the extensive use pentoxifylline as an antifibrotic agent in liver and vascular fibrosis (Becker et al., 2001; Raetsch et al., 2002; Chen et al., 1999; Tarcin et al., 2003). The fact that the cGMP analog 8-Br-cGMP inhibited collagen I synthesis and induced apoptosis in PD cells suggests that in the case of sildenafil the in vivo effects on the function of the fibroblasts/myofibroblasts in the TA may be mediated by the elevation of cGMP levels. In addition, cGMP analogs, PKG activators, and PDE inhibitors have been shown to inhibit collagen synthesis (Redondo et al., 1998; Wollert et al., 2002), and induce apoptosis (Sirotkin et al., 2000), and some of the PDE inhibitors like sulindac sulfone (Exisulind) are effective as anticancer agents because of their intense pro-apoptotic action (Piazza et al., 2001; Thompson et al., 2000). However, since pentoxifylline did not affect cGMP levels in the human PD fibroblasts, and the drug is considered to be a non-specific inhibitor of cAMP-PDE (Lin et al., 2002c; Liang et al., 1998), and at least in some cell types does not affect cGMP levels (Chen et al., 1999), the increase in cAMP may also have played a role in the antifibrotic effects observed with pentoxifylline. Whether this occurs via the inhibition of PDE4 present in TA and PD remains to be established. Pentoxifylline may also act through its blockade of PDGF-induced activation of the mitogen activated protein kinase system (Souness et al., 2000) and of other cytokine-mediated fibrogenic mechanisms (Raetsch et al., 2002).

The daily dose of pentoxifylline used was ⅕ of the oral dose normally employed in rats for the long-term treatment of fibrosis (Chen et al., 1999; Tarcin et al., 2003), and in the case of sildenafil, it is ½ to ⅐ of the chronic dosage used in recent studies in rats (Sebkhi et al., 2003). When the 10 mg/kg/day dose is translated into the equivalent dose in humans by correcting for differences in the body weight/skin area (Freireich et al., 1966), it is roughly 1.5 mg/kg which is about the dose ingested by men with an on demand single 100 mg tablet. The selected dose was dispensed in 24 hours and not as a bolus administration, so that concentrations at a given time should be much lower, considering the short half-life (about 4-6 hours) of sildenafil. Therefore, the daily doses of the PDE inhibitors tested in the current work are not supra-pharmacological or associated with toxicity. In addition, it is possible that local administration of either L-arginine or the PDE inhibitors, e.g. by injection into the plaque or in vehicles able to traverse the skin and TA may considerably reduce the effective dosage.

It is unknown why administration of L-arginine, which should increase NO synthesis and hence cGMP levels and has been shown to be effective in arresting the growth of the TGF-B1 induced plaque in the rat model of PD, failed to stimulate apoptosis, as could be expected from its effects increasing it in vivo in the smooth muscle of the pulmonary arteries (Wang et al., 1999; Holm et al., 2000). However, the absence of a stimulation of the apoptotic index in the PD plaque by L-arginine may agree with the decrease in apoptosis observed in liver transplants which is in line with the anti-apoptotic effects of NO in certain conditions and tissues (Wang et al., 2002b). In any case, not only cGMP but its down-stream compound in the NO-cGMP cascade, PKG, is also effective in preventing fibrosis and remodeling in balloon-injury and arterial restenosis (Wollert et al., 2002; Chiche et al., 1998), as shown by gene transfer of the PKG cDNA in rats.

The results demonstrating the presence of PDE5A and PDE4 in the TA and PD plaque in the human and rat, and in their respective fibroblast cultures, provide a rationale for the anti-fibrotic effects of PDE inhibitors on the PD animal model and on the PD cell cultures. The PDE5A1 and PDE5A2 proteins have been previously localized in human penile corpora cavernosa (Lin et al., 2000a). The PDE5A3 variant was also found in corpora cavernosa and confined to tissues with a smooth muscle or cardiac muscle component, and is twice as sensitive as PDE5A1 to sildenafil, but, as with PDE5A1 and 2, is subject to transcriptional up-regulation by both cAMP and cGMP (Lin et al., 2002a; Turko et al., 1999). As to PDE4, cAMP can activate PKG nearly as effectively as cGMP, so that eventually, the inhibition of PDE4 may cause PKG effects (e.g., counteracting fibrosis) similar to those exerted by as the inhibition of PDE5A.

The results reported above indicate that pharmacological interventions aimed at elevating NO, cGMP, or PKG levels, and possibly cAMP, in the penis are of use for the treatment of PD, and potentially, for other fibrotic conditions. This work has not addressed the question on whether intervention would induce regression of an already well-formed plaque, but comparison of multiple gene expression profiles in human PD and the related Dupuytren's disease suggest that both conditions are in a dynamic cell and protein turnover involving replication, differentiation, apoptosis, and collagen and extracellular matrix synthesis and breakdown (Magee et al., 2002b; Gonzalez-Cadavid et al., 2002; Gholami et al., 2002). Therefore, modulation of any of these processes may involve the plaque, as has been observed in generalized fibrotic conditions (Lee et al., 2001; Lai et al., 2000).

Example 16

Figure 15:
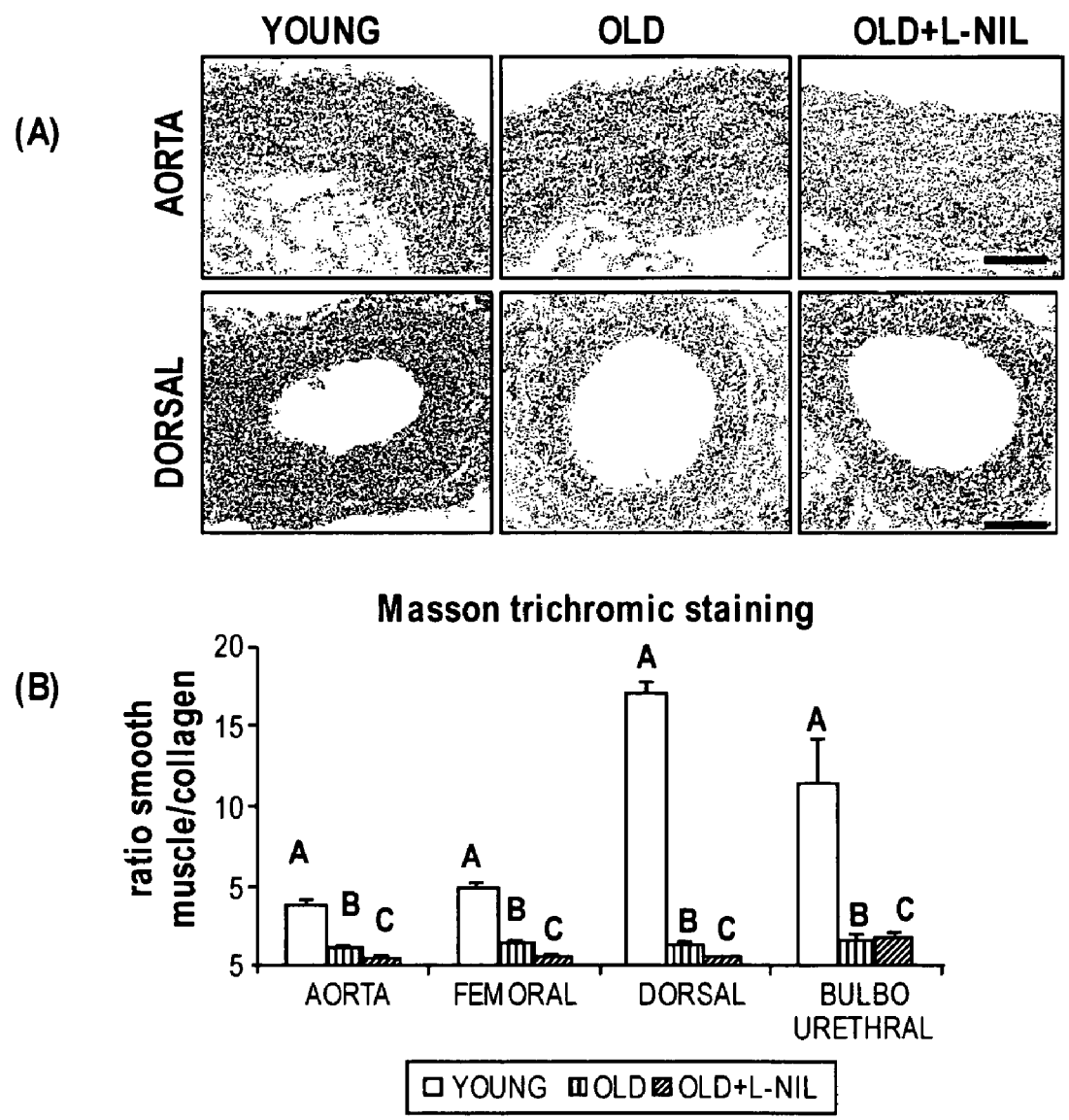
FIG. 15. Intensification by iNOS blockade of aging-related fibrosis in the arterial media. Old male rats were given L-NIL for 3 weeks, or left untreated. Young untreated rats served as controls. Tissue sections were obtained from penis (to visualize the dorsal and bulbo-urethral penile arteries) and from the aorta and femoral artery, and stained with Masson (SMC: red; collagen: blue). (A) Micrographs from selected arteries and tissue sections, as indicated. Bar=50 μm. (B) Quantitative image analysis (QIA) expressed as ratios of areas occupied by SMC and collagen, as means+/−SEM. Aorta: A vs. B, C $p<0.001$; B vs. C $p<0.01$; Femoral: A vs B, C $p<0.001$; B vs. C $p<0.01$; Dorsal: A vs B, C $P<0.001$ B vs. $P<0.05$; Bulbourethral: A vs B, C $p<0.001$; B vs. C: NS.

Intensification of Aging-Related Fibrosis in the Arterial Media by iNOS Inhibition In order to determine whether aging per se is associated with an intensification of collagen deposition and a relative loss of SMC in the media from the aorta to the peripheral resistant arteries (Breithaupt-Grogler and Belz, 1999; Robert, 1999; Integan and Schiffrin, 2000), staining was performed on sections from the abdominal aorta, femoral, and brachial arteries as well as from the penile shaft focusing on two peripheral putative resistance arteries: the bulbourethral and dorsal arteries of the penis. FIG. 15A shows that in the media of the dorsal penile artery, few collagen fibers were present in the young rats but were considerably increased in the aged animals, resembling the situation seen in the aorta. Consistent with the model that iNOS may act as antifibrotic agent within the vascular tree, the administration of L-NIL, a specific inhibitor of iNOS activity, for 3 weeks to the aged rats led to a further increase in the collagen fibers within the media of the aorta and the dorsal penile artery.

Image analysis was performed in all arteries with the exception of the brachial (FIG. 15B), on 5 animals per experimental group, and 6 sections per animal (3-4 fields per section). In all vessels studied, there was a marked reduction in the SMC/collagen ratio with aging. Following iNOS blockade by L-NIL, there was a further exacerbation in the amount of collagen within the media (with the exception of the bulbourethral artery), suggesting that the decrease in NO production by the inhibition of iNOS leads to an intensification of the aging-related fibrosis. These alterations were not accompanied in the resistant arteries by a significant increase in the intima/media thickness (IMT), whereas in the aorta and femoral the IMT was higher (Table 2). The measurements of the luminal diameter (Table 2) confirmed the clinical observation that the dorsal and bulbo-urethral arteries, with a luminal diameter well below 350 um, fall within the definition of resistance arteries (Intengan and Schriffin, 2000; Moore and Schiffrin, 2001).

Example 17 iNOS Induction and Peroxynitrite Deposition in the Arterial Media With Aging

All the antibodies used in this work have been validated (Ferrini et al., 2001a, 2002; Vernet et al., 2002; Goettsch et al., 2001), and in the case of the iNOS antibody it was additionally tested in the current work by immunocytochemistry against rat fibroblast cultures (penile tunica albuginea, see Ferrini et al., 2002; Vernet et al. 2002) induced to express iNOS with a cytokine cocktail, producing 130 uM nitrites (Hung et al., 1995). These cells were intensively stained, in comparison to uninduced cells (<10 uM nitrites) that were negative (not shown). Western blots revealed the expected single 130 kDa band in extracts of the induced cells, also detected by the corresponding monoclonal antibody, and this band was absent in aorta extracts from a young iNOS knockout mouse that had received LPS (4 mg/kg) to induce iNOS, whereas the band was visible in the respective extract from the similarly treated wild type animal (not shown).

Figure 16:
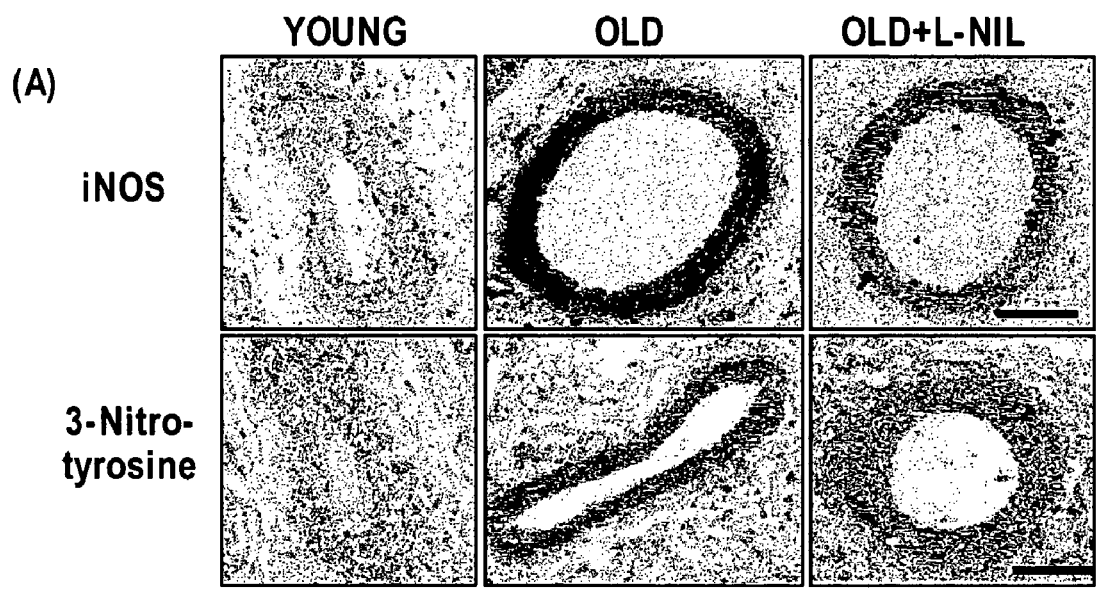
FIG. 16. Reduction by iNOS blockade of the aging-related stimulation of the nitrosative pathway in the media of the penile arteries. Sections were immunostained as indicated. Nitrotyrosine is a marker for peroxynitrite. (A) Micrographs from selected arteries and tissue sections, as indicated. Bar=50 μm. (B) QIA as on FIG. 15, expressed as intensity of immunostaining per area, as means+/−SEM. For iNOS: Dorsal: A vs. B $p<0.05$; A vs. C: N.S.; B vs C: $p<0.05$; Bulbourethral: A vs. B: $p<0.05$; A vs. C: N.S; B vs. C: $p<0.05$. For 3-nitrotyrosine: Dorsal: A vs. B: $p<0.001$; A vs. C: $p<0.05$; B vs. C: $p<0.05$; Bulbourethral: A vs B $p<0.01$; A vs. C: N.S; B vs. C: $p<0.01$.
Figure 16:
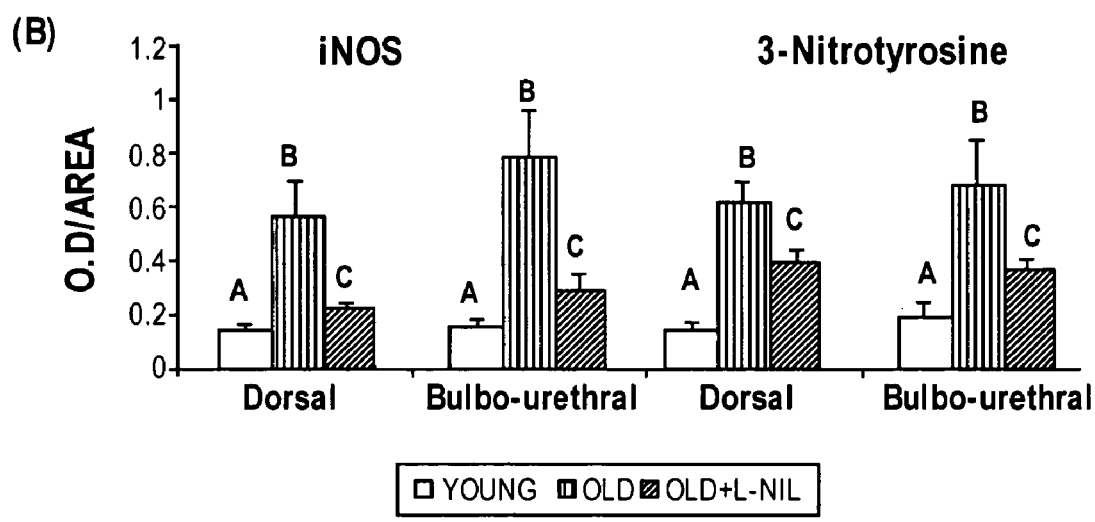

This antibody showed that iNOS is increased with aging in parallel with collagen deposition in the arterial media throughout the vascular tree, confirmed by detection of nitrotyrosinylated proteins. The latter arise from peroxynitrite produced by the reaction between NO and ROS, and therefore are an indirect measure of NOS activity. FIG. 16A shows negligible iNOS expression and nitrotyrosine formation in the dorsal artery of the penis of the young animals, and a remarkable intensification of both processes with aging. The iNOS staining in these vessels was mainly confined to the media and intima. A similar finding was seen in the aorta, brachial, and femoral arteries (not shown). When L-NIL, the inhibitor of iNOS activity, was given, there was a reduction in iNOS expression, which combined with the direct decrease of iNOS activity, led to a reduction in peroxynitrite formation. Quantitation by image analysis confirmed these changes in the resistant dorsal and bulbourethral arteries of the penis (FIG. 16B), as well as in the aorta and femoral arteries (not shown). The brachial artery was not subjected to image analysis.

Example 18

Figure 17:
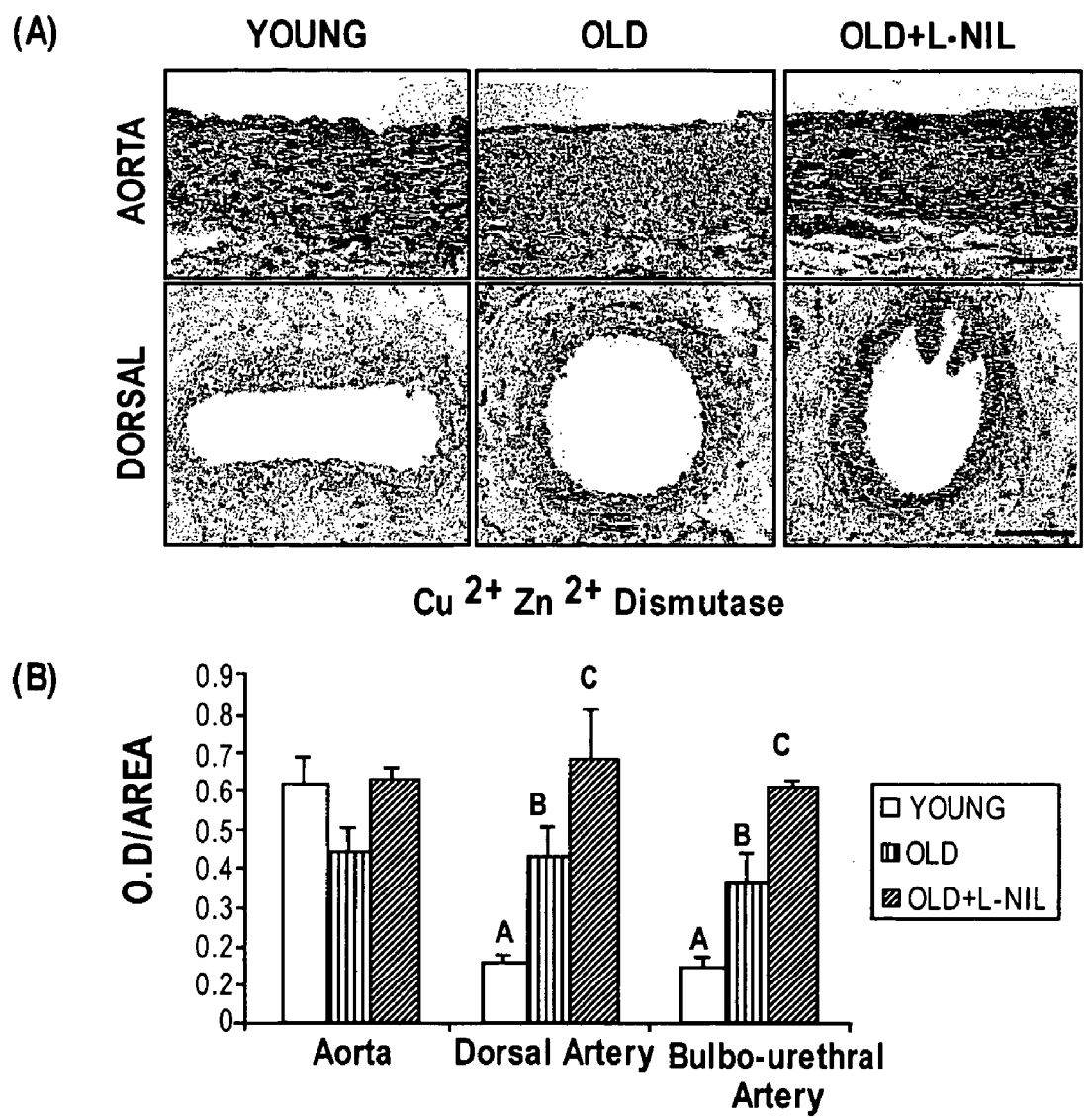
FIG. 17. Intensification by iNOS blockade of aging-related oxidative stress in the arterial media. Tissue sections were immunostained for $Cu^{2+} Zn^{2+}$ SOD and for $Mn^{2+}$ SOD. (A) Micrographs from selected arteries and tissue sections only for $Cu^{2+} Zn^{2+}$ SOD, as indicated. Bar=50 μm. (B) QIA as on FIG. 16, expressed as intensity of immunostaining per area, as means+/−SEM. Dorsal: A vs C $p<0.05$; A vs. NS; B vs. NS; Bulbourethral: A vs. C $P<0.001$; A vs. B $P<0.05$; B vs. $P<0.01$ A vs B, C $p<0.001$; B vs. C: NS. $Mn^{2+}$ SOD gave essentially similar results (not shown).
Figure 18:
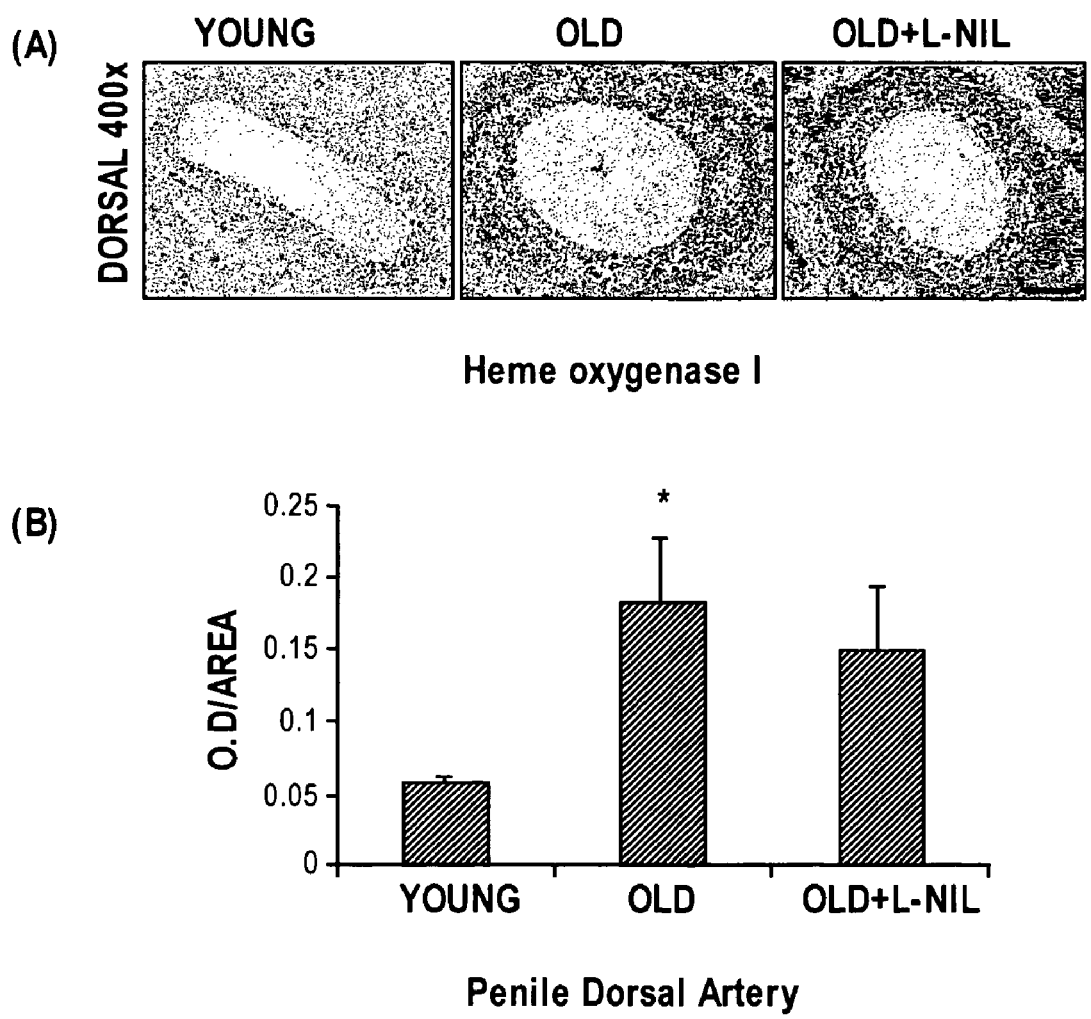
FIG. 18. Differential expression of another marker of oxidative stress, heme oxygenase 1, in the adventitia of the arterial wall. Sections were immunostained with an antibody against heme oxygenase I and counterstained with hematoxylin. (A) Micrographs from the dorsal artery. Bar=50 μm. (B) QIA as on previous figures. Values expressed as means+/−SEM. *$p<0.05$: young vs old (t test).

Effects of iNOS Inhibition on ROS Production, Apoptosis, and PAI in the Arterial Media Utilizing the Cu/Zn SOD as an indirect marker of ROS, the production of ROS in the arterial media was found to be considerably increased with aging in the femoral, brachial and resistant arteries but not in the aorta, and this process was further increased with iNOS inhibition by L-NIL (FIG. 17A). This was additionally confirmed by image analysis (FIG. 17B), that indicated that L-NIL blockade of iNOS activity raised Cu/Zn SOD by 40 to 50%. The Mn SOD gave similar results from the aorta to the resistant arteries (not shown). Another antioxidant enzyme, heme oxygenase I, demonstrated the same aging related changes in the penile dorsal artery, as observed for both SOD enzymes, but remarkably, L-NIL did not induce a further significant change in the expression of this enzyme (FIG. 18). The localization of virtually all the expression of heme oxygenase-1 was in the arterial adventitia, rather than in the media as seen for the SOD enzymes.

Figure 19:
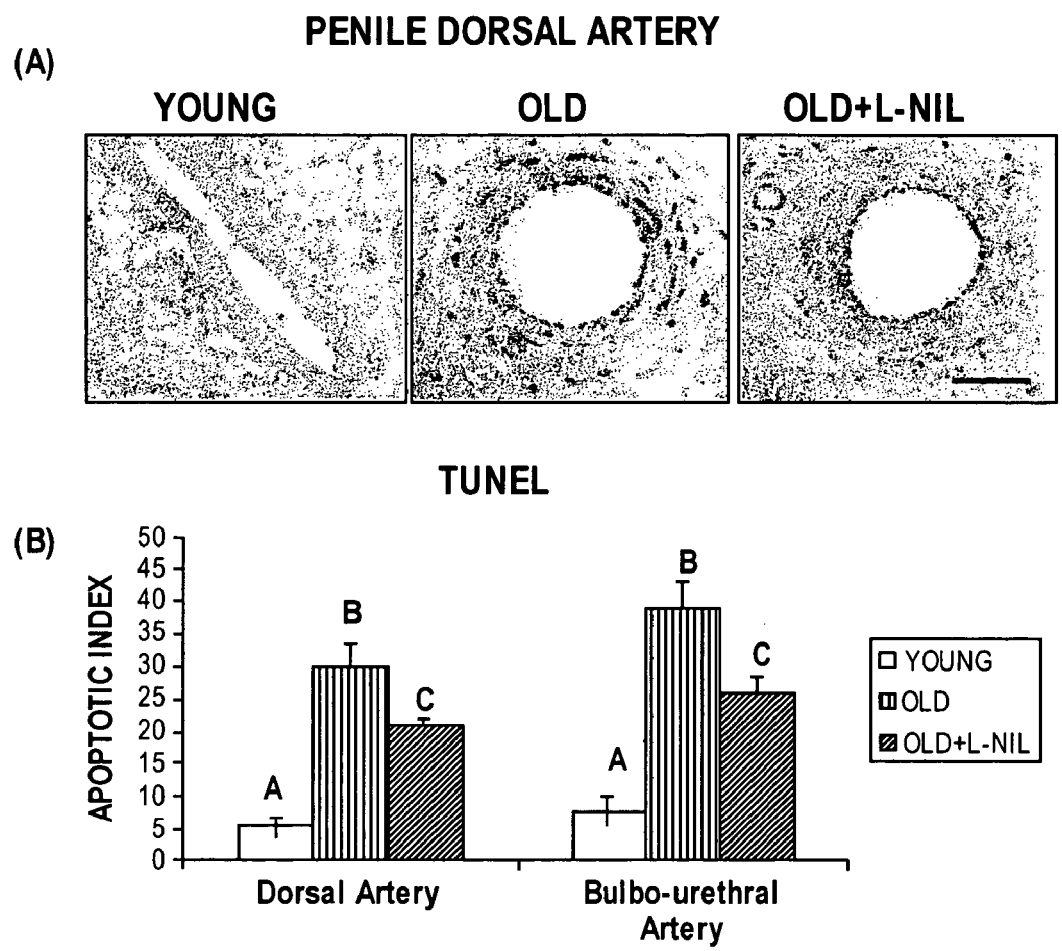
FIG. 19. Reduction by iNOS blockade of the aging-related stimulation of apoptosis in the media of the penile arteries. Sections were immunostained with the TUNEL procedure and counterstained with methyl green. (A) Micrographs from selected arteries and tissue sections, as indicated. Bar=50 μm (B) QIA as on previous figures, expressed as apoptotic index (percent number of apoptotic cells/total number of cells), as means+/−SEM. Dorsal: A vs. B, C $p<0.001$; B vs. C $p<0.05$; Bulbourethral: A vs. C $p<0.001$; A vs. $p<0.05$; B vs C $p<0.01$ FIG. 20. Intensification by iNOS blockade of the aging-related stimulation of PAI expression in the media of the penile arteries. Sections were immunostained with an antibody against PAI and counterstained with hematoxylin. (A) Micrographs from the dorsal artery. (B) QIA for both the dorsal penile and bulbourethral arteries, as on previous figures. Bar=50 μm Values expressed as means+/−SEM. a vs. b,c: $p<0.001$.

The NO/ROS balance was significantly altered throughout the entire arterial media by iNOS inhibition with L-NIL via a reduction in NO synthesis (denoted by peroxynitrite) and a stimulation of ROS formation (denoted by the antioxidant enzymes). Apoptosis of the SMC within the media of the penile resistance arteries increased with aging, and decreased subsequently in the old animals receiving L-NIL treatment (FIG. 19A). The apoptotic index was calculated for both the dorsal and bulbourethral penile arteries by image analysis, and was higher in aged compared to young rats but L-NIL treatment resulted in a reduction in this index (FIG. 19B).

Figure 20:
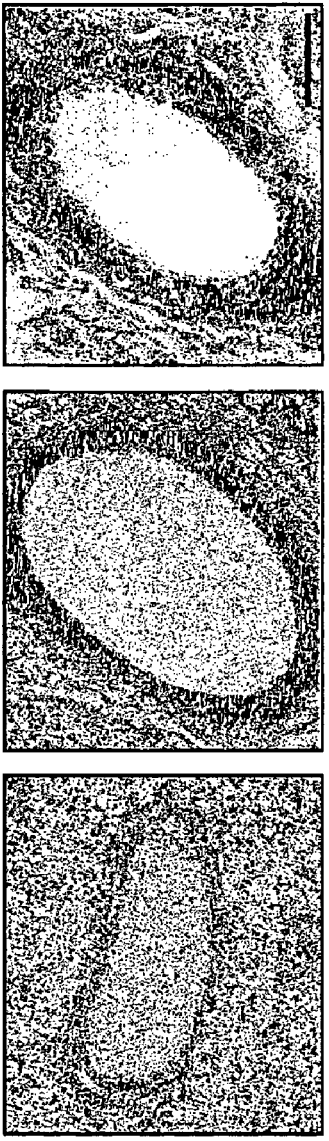
Figure 20:
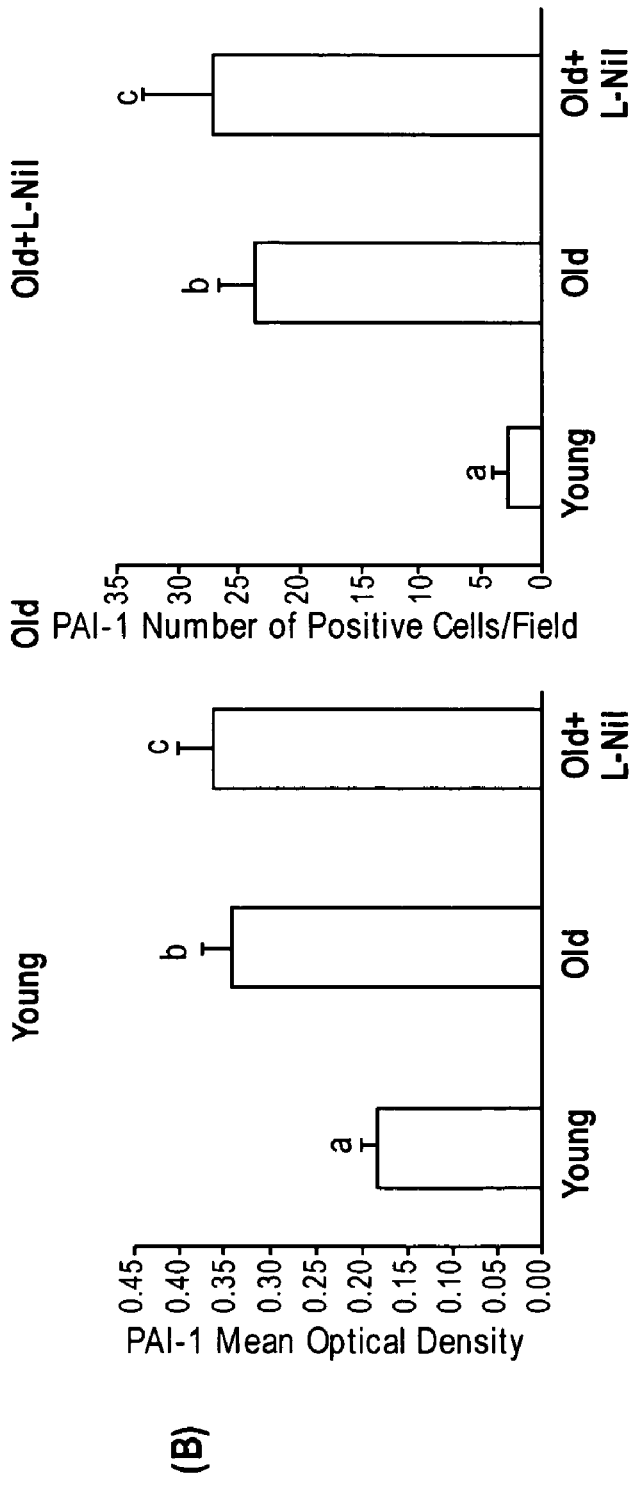

Aging alone or in combination with iNOS inhibition affected the expression of PAI-1, a well characterized inhibitor of metalloproteinases (Li et al., 2000; Kaikita et al., 2002). Inhibition of PAI is associated with an increase in collagen fibers due to its interference with metalloproteinases that are involved with the breakdown of collagen. Compared to young animals, PAI expression was considerably increased in the arterial media with aging, and was even further stimulated by iNOS inhibition, as seen in the resistant artery (FIG. 20A). Quantitative image analysis for both the mean intensity of expression (FIG. 20B) and the number of PAI positive cells (FIG. 20B) indicated that the increase in PAI by aging alone was between 2- and 5-fold, respectively. However, the effect of L-NIL on PAI expression in the aged media was negligible (FIG. 20B).

These results indicate that the arterial media from the aorta to the small resistant arteries undergoes many of the changes that occur within the corporal tissue with aging, namely: a) a reduction in the SMC/collagen ratio; b) an increase in markers of oxidative stress, and of inhibitors of collagen degradation, such as PAI, which are known pro-fibrotic factors; and c) the spontaneous induction of iNOS, which is believed to act as an anti-fibrotic agent (Vernet et al., 2002; Ferrini et al, 2002; Hochberg et al, 2000). However, the increase in SMC apoptosis in the media of the resistant arteries of the penis, presumably leading to a reduction in the absolute SMC content, contrasts with what has been reported for large vessels such as the aorta and the femoral artery (Connat et al., 2001; Asai et al., 2000), but does agree with the process described in the corporal SMC (Garban et al., 1995; Ferrini et al., 2001a).

Our results also confirm the role for NO derived from iNOS produced by the SMCs of the media in combating aging-related fibrosis within the media, as evidenced both by the increase in ROS and an intensification of fibrosis within the media of the arterial wall when iNOS activity is inhibited. The excessive deposition of collagen fibers observed in the arterial media of the aged rats is thought to lead to arterial stiffness or arteriosclerosis in the vascular system. Because of the apoptosis occurring in the SMC, the relative reduction in the SMC/collagen ratio is intensified in the resistant arteries of the penis, in comparison to the larger arteries, e.g. the aorta. This process may be a primary factor involved in the development of essential hypertension, which is very prevalent with aging.

In the case of the penile arteries, the data also indicate that a reduction in the ability of penile vessels to relax normally during cavernosal nerve stimulation leading to an erection, may contribute in part to the high prevalence of ED associated with aging. In addition to this aging-related fibrosis of the arterial media (Breithaupt-Grogler and Belz, 1999; Robert, 1999; Integan and Schiffrin, 2000; Fornieri et al., 1992), it is well documented (Grein and Schubert, 2002) that similar fibrotic changes occur within the penile corporal sinusoids. The corporal tissue comprises primarily of a syncytium of vascular SMC with an endothelium lining which is biologically and physiologically indistinguishable from the one present in the media and intima of the vascular tree (Krall et al., 1988) and may be considered a highly evolved extension of these arterial tissues. Therefore, insults that afflict the arterial media may also afflict the corporal SMCs, resulting in defective vaso-relaxation in both the corporal tissue (ED) and the arterial tree (hypertension). Indeed, the prevalence of ED and hypertension in man seems to parallel each other as a function of age (Sullivan et al., 2001; Melman and Gingell, 1999), and many disorders that damage one of these vascular tissues also seem to impact the other e.g. diabetes, chronic renal failure, etc. In all these disorders, vascular oxidative stress and fibrosis, leading to arteriosclerosis, are common denominators at the histological and molecular and levels.

The results on the abdominal aorta and the rest of the smaller arteries and arterioles are in agreement with previous studies from other groups showing in the aging rat both an intensification of oxidative stress (van der Loo et al., 2000; Demaree et al., 1999) and collagen deposition (Goettsch et al., 2001; Chou et al., 1998; Csiszar et al., 2002), that is the likely cause of the reduction of the SMC/collagen ratio within the media. This alteration, that in the large vessels does not appear to be caused by SMC apoptosis (Connat et al., 2001; Asai et al., 2000), would explain the clinical observation in humans of diminished arterial elasticity associated with aging, which in some instances is compounded by a reduction of the arterial lumen due to media/intimal thickening (Moore and Schiffrin, 2001). The fact that different vessels in the arterial tree, regardless of size or location, seem to experience fibrosis of the media may explain dysfunctional vasorelaxation or impaired perfusion of many organs that occurs with aging (Breithaupt-Grogler and Belz, 1999; Robert, 1999; Integan and Schiffrin, 2000; Fornieri et al., 1992; Garban et al., 1995; Ferrini et al., 2001a; Rogers et al., 2003; Berry et al., 2001). The ability of the resistant arteries to relax normally is fundamental for the control of the systemic blood pressure, and as exemplified by the dorsal penile and bulbourethral arteries in this study, they showed an intensification of SMC loss due to apoptosis without a change in IMT, which agrees with has been previously reported for the mesenteric small resistant arteries in hypertension (Rizzoni et al., 2000).

Although NO has been shown in animal models to be protective against atherosclerosis and restenosis in the vascular system (Gewaltig and Kojda, 2002; Cheng et al., 2001), and fibrosis throughout the vascular tree and other organs (Ferrini et al., 2002; Vernet et al., 2002; Gewaltig and Kojda, 2002), the concept that NO may prevent aging-related arteriosclerosis is novel. In fact, the pro-apoptotic action of NO (Gewaltig and Kojda, 2002; Kibbe et al., 1999) would suggest that it decreases the SMC/collagen balance through increased cell death. We have found in the aged animals treated with L-NIL an association between NOS inhibition and subsequent reduction of nitrotyrosine formation, with a decrease of apoptosis, which would suggest that NO does cause some SMC loss in the penile resistant arteries similar to what has been previously assumed to occur in the corpora cavernosa (Ferrini et al., 2001a). However, an increased apoptotic index may be balanced by a stimulation of cell replication or tissue remodeling (Ingengan and Schiffrin, 2001), and what really matters physiologically is the net balance between both processes. In the data above, the relative number of SMC in the arterial media (represented by the smooth muscle/collagen ratio), was severely reduced when NO synthesis was diminished by L-NIL. This, together with the well known effects of NO in scavenging the profibrotic compound, ROS, thereby decreasing collagen synthesis and down-regulating its breakdown (see Ferrini et al., 2002; Vernet et al., 2002), would support the view of an overall beneficial role of NO in preventing arterial stiffness and loss of compliance of the corpora cavernosa.

A final question is whether collagen accumulation with aging is at least partially mediated via the regulation of PAI-1, TIMP1 and other metalloproteinase inhibitors (Li et al., 2000; Kaikita et al., 2002), that increase in different types of fibrosis. The current results with PAI, combined with previous data where we observed considerable metalloproteinase and PAI mRNA expression in the fibrotic plaque of Peyronie's disease in the human and rat (Magee et al., 2002a), would suggest that although the increase in the pro-fibrotic PAI may induce a compensatory elevation of metalloproteinase levels, the enzyme would remain inhibited and the net result would be an impaired collagen breakdown.

In conclusion, the results indicate that within the arterial system and the cavernosal tissue it may be possible to pharmacologically modulate a) the NO/ROS balance with NO donors or other NO generators together with antioxidants, and b) the PAI/MMP balance with agents modifying their relative expression. Such novel therapies may constitute viable approaches for the prevention and/or therapy of vascular disorders that involve the arterial media and the corpora.

Example 19

Gene Therapy With iNOS cDNA

All studies throughout this section, unless specifically indicated, are performed in the rat model where the PD-like plaque is initiated by the injection of TGF-$\beta$1 (0.5 ug) into the TA. TGF-$\beta$1 transcriptionally amplifies its own synthesis, allowing for a single injection. Saline-injected TA are used as controls. The AdV-CMV-iNOS construct has been prepared by subcloning the iNOS cDNA driven by the strong CMV promoter (Garban et al., 1997), from a plasmid construct into an AdV plasmid vector, and purifying the AdV construct, as previously described for PnNOS (Magee et al., 2002a). This AdV vector is replication-defective and helper-dependent, and therefore is non-infectious and totally innocuous. In addition, it lacks virtually all the original viral sequences that may be immunogenic. This AdV construct can be transfected into the TA, and it has been cloned and utilized for other therapeutic purposes in the penis (Magee et al., 2002a).

Rats are injected in the TA at the same site as the TGF-$\beta$1 was injected 5 days earlier (as evidenced by a non-absorbable suture) with $10^8$ and $10^9$ vp of either AdV-CMV-iNOS in 50 ul saline, or with vehicle (saline) only. This 5-day waiting period between the TGF-$\beta$1 injection and the cDNA construct avoids any interference of the viral preparation with the injected TGF-$\beta$1, and/or its dispersion by the electroporation applied to enhance transfection of the iNOS construct. The resulting 4 groups of rats are allowed to develop the plaque for 40 more days, sacrificed, and the area around the plaque is excised, fixed, paraffin-embedded, and sectioned (Ferrini et al., 2002, Vernet et al., 2002). In another 2 groups of rats injected with TGF-$\beta$1 to induce a plaque, the cDNA construct and saline are injected 45 days after the TGF-$\beta$1 injection (when the plaque has already formed) and 30 days later the animals are sacrificed.

In the "early" treatment groups (iNOS given 5 days after TGF-$\beta$1 injection), the TA of the iNOS-treated animals shows, in comparison with controls: 1) a decrease in the size of the plaque as evidenced by Masson, collagen I/III staining, and hydroxyproline content; 2) a higher expression of iNOS and nitrotyrosine; 3) decrease of ROS; and 4) increase in the apoptotic index of the fibroblasts/myofibroblasts. In the "late" treatment group, where the iNOS is injected 45 days after TGF-$\beta$1 injection, at least some regression of the plaque is obtained.

Example 20

Oral NO Donors or NOS Substrate

Plaques are induced in the TA of rats by TGF-$\beta$1 injection (Ferrini et al., 2002). Drinking water containing molsidomine (N-ethoxycarbonyl-3-morpho-linosydnomine), at 0.12 g/l (Benigni et al., 1999) (freshly prepared each day) is given to 2 groups of rats, an early and a late treatment group. The dose of molsidomine used is based on the report in which it was utilized for 22 days to protect against tubulo-interstitial injury in a rat model of chronic glomerular disease (Uckert et al., 2001), and is calculated to be equivalent to approximately 15 mg/kg/day in the rat. In the case of L-arginine, it is given only as a late treatment, but at 2 doses: 22.5 and 10.0 g/l (in drinking water) (2 groups). Previously, the 22.5 g/l dose of L-arginine was used for 45 days to elevate NOS activity in the rat penis (Moody et al., 1997), and to inhibit the plaque with the early treatment is equivalent to roughly 2.8 g/kg/day.

Example 21

Oral PDE Inhibitors to Regress the PD Plaque

Sildenafil (specific PDE5 inhibitor), and pentoxifylline (non-specific PDE inhibitor), are given at doses of 100 mg/l in the drinking water, as well as a control (drinking water only), beginning on day 45 (3 groups). The study may be repeated at double or possibly quadruple the dosage above (2 groups). Reduction in plaque size was observed with both sildenafil and pentoxifylline during the entire time of plaque development ('early treatment'), and this type of treatment may be as effective in regressing the plaque ('late treatment').

Eleven PDE mRNAs for the respective isoforms have so far been identified by RT/PCR in the human (Kim et al., 2000). Due to the fact that pentoxifylline is more effective than sildenafil at inhibiting apoptosis in the PD plaque, it is likely that more than one PDE gene product may be involved in plaque development, and the pure PDE4 inhibitor, rolipram (Uckert et al., 2001) may identify a related, relevant PDE. The increase in cAMP may act directly, or through stimulating the synthesis of cGMP (Kim et al., 2000). Rolipram, is given to early and late treatment groups (2 groups), at the same dose, in order to determine whether increasing cAMP levels is as, or more, effective than cGMP.

Example 22

Gene Therapy with PKG

The AdV-PKG (wild type) and AdV-PKGcat (mutated) are injected into the TA (2 groups). The constitutively active PKG1 mutant consists of the carboxy-terminal catalytic domain without the amino-terminal regulatory domain where cGMP binds (Wollert et al., 2002). Both the wild type and mutated constructs are obtained from Dr. Stefan Janssens (Center for Transgene Technology and Gene Therapy, University of Leuven, Belgium).

Example 23

Screening of Other cGMP-Dependent PDE Isoforms

Tissues from human normal TA and PD plaque preserved in RNA later (Magee et al., 2002b; Ferrini et al., 2002) or the previously isolated RNAs from these tissues, conserved at −80° C., are used. In the case of the rat model, a 2-3 mm transverse section is obtained at the site of saline or TGF-β1 injection 45 days after plaque initiation. RNA is isolated from 2 groups of human and 2 groups of rat tissues.

Example 24

Oral Antioxidant

The antioxidant vitamin E (α-tocopherol) is given in a specially prepared oral diet, so that the animal receives in an early treatment phase approximately 200 IU/kg/bw/day, whereas controls receive the normal diet containing less than 20 IU/kg (Gonca et al., 2000). The third group (3 groups) receive twice a day an intramuscular injection (10 mg/kg) of another antioxidant compound that ameliorates oxidative stress and lipid peroxidation, the glutathione precursor S-adenosyl-L-methionine (SAM) (Muriel et al., 1998b). Depending on which antioxidant is more efficacious in the early treatment, a late treatment beginning on day 45 after TGF-β1 injection and lasting for 30 days is performed with the selected compound compared to a control group with normal diet (2 groups).

Example 25

Effect of Obliterating iNOS on Collagen Breakdown. Plaque in the iNOS Knockout

The PD-like plaque is induced with TGF-β1 given into the TA of the iNOS knock-out mouse, utilizing the wild type mouse as a control, (2 groups, n=6). 45 days after the injection of TGF-β1, the mice are sacrificed and the tunical tissues is either fixed and sectioned for immunohistochemistry (n=3) or used for RNA isolation (n=3). The experiment is repeated, but this time, 8 days before sacrifice, the collagen I promoter plasmid is injected and electroporated (Magee et al., 2002a) (2 groups; n=3). Animals are sacrificed and fresh tunical plaque tissue obtained for β-galactosidase expression and zymography.

Example 26

Modulation of MMP Through Thymosin Peptides. Treatment With Thymosin β

Thymosin β4 and 10 are given daily intraperitoneally as a late treatment at 60 ug/day, every other day (2 groups) (Sosne et al., 2002). Such treatment with thymosin-β4 (the most abundant thymosin) has been used for promoting healing of dermal wounds (Sosne et al., 2002)). Plasmid preparations of a cDNA encoding both peptides (200 ug/rat) are also given by injection/electroporation to the TA (2 groups), as a late treatment (i.e. 45 days after the TGF-β1 injection, to induce the PD like plaque).

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alves, M. A. Barao, L. N. Odo, G. Nascimento Gomes, C. Franco Md Mdo, D. Nigro, S. R. Lucas, F. R. Laurindo, L. I. Brandizzi, F. Zaladek Gil. L-Arginine effects on blood pressure and renal function of intrauterine restricted rats. Pediatr Nephrol 17 (2002) 856-862.

Anderson M S, Shankey T V, Lubrano T, Mulhall J P (2000a) Inhibition of Peyronie's plaque fibroblast proliferation by biologic agents. *Int J Impot Res* 12 Suppl 3:S25-31.

Arthur M J. (2000) Fibrogenesis II. Metalloproteinases and their inhibitors in liver fibrosis. Am J Physiol 279(2): G245-9

Asai K, Kudej R K, Shen Y T, et al. Peripheral vascular endothelial dysfunction and apoptosis in old monkeys. Arterioscler Thromb Vasc Biol. 2000; 20:1493-1499.

Babal P, Pechanova O, Bernatova I, Stvrtina S. (1997) Chronic inhibition of NO synthesis produces myocardial fibrosis and arterial media hyperplasia. *Histol Histopath* 12:623-9.

Badalamente M A, Sampson S P, Hurst L C, Dowd A, Miyasaka K, Brook S (1996) The role of transforming growth factor beta in Dupuytren's disease. *J Hand Surg* 21A: 210-215.

Becker, V. Perkovic, T. D. Hewitson. Pharmacological intervention in renal fibrosis and vascular sclerosis. J. Nephrol. 14 (2001) 332-339.

Beckmann J S, Koppenol W H (1996) Nitric oxide, superoxide, and peroxynitrite: the good, the bad, and the ugly. *Am J Physiol* 271:C1424-C1437.

Behr-Roussel D, Rupin A, Simonet S, et al. Effect of chronic treatment with the inducible nitric oxide synthase inhibitor N-iminoethyl-L-lysine or with L-arginine on progression of coronary and aortic atherosclerosis in hypercholesterolemic rabbits. Circulation. 2000; 102:1033-1038.

Benigni A, Zoja C, Noris M, Corna D, Benedetti G, Bruzzi I, Todeschini M, Remuzzi G (1999) Renoprotection by nitric oxide donor and lisinopril in the remnant kidney model. *Am J Kidney Dis* 33(4):746-53.

Berry C, Brosnan M J, Fennell J, Hamilton C A, Dominiczak A F. Oxidative stress and vascular damage in hypertension. Curr Opin Nephrol Hypertens. 2001; 10:247-255

Bing, D. Junbao, Q. Jianguang, L. Jian, T. Chaoshu. L-arginine impacts pulmonary vascular structure in rats with an aortocaval shunt. J Surg Res 108(2002) 20-31.

Bivalacqua T J, Armstrong J S, Biggerstaff J, et al. Gene transfer of extracellular SOD to the penis reduces $O_2$-* and improves erectile function in aged rats. Am J Physiol Heart Circ Physiol. 2003; 284:H1408-1421.

Bivalacqua T J, Diner E K, Novak T E, Vohra Y, Sikka S C, Champion H C, Kadowitz P J, Hellstrom W J. (2000) A rat model of Peyronie's disease associated with a decrease in erectile activity and an increase in inducible nitric oxide synthase protein expression. *J Urol* 163:1992-8.

Boffa J J, Tharaux P L, Placier Sm, Ardaillou R, Dussaule J C, Chatziantoniou C (1999) Angiotensin II activates collagen type I in the renal vasculature of transgenic mice during inhibition of nitric oxide synthesis: evidence for an endothelin-mediated mechanism. *Circulation* 100(18):1901-8.

Boger R H, Bode-Boger S M, Szuba A, Tsao P S, Chan J R, Tangphao O, Blaschke T F, Cooke J P (1998) Asymmetric dimethylarginine (ADMA): a novel risk factor for endothelial dysfunction: its role in hypercholesterolemia. *Circulation* 98:1842-7.

Bosch P, Musgrave D S, Lee J Y, Cummins J, Shuler T, Ghivizzani T C, Evans T, Robbins T D, Huard (2000) Osteoprogenitor cells within skeletal muscle. *J Orthop Res* 18(6): 933-44.

Breithaupt-Grogler K, Belz G G. Epidemiology of the arterial stiffness. Pathol Biol (Paris). 1999; 47:604-613.

Bugno M, Witek B, Bereta J, Bereta M, Edwards D R, Kordula T (1999) Reprogramming of TIMP-1 and TIMP-3 expression profiles in brain microvascular endothelial cells and astrocytes in response to proinflammatory cytokines. *FEBS Lett* 448(1):9-14.

Cai H, Harrison D G. Endothelial dysfunction in cardiovascular diseases: the role of oxidant stress. Circ Res. 2000; 87:840-844

Cao M, Westerhausen-Larson A, Niyibizi C, Kavalkovich K, Georgescu H I, Rizzo C F, Hebda P A, Stefanovic-Racic M, Evans C H (1997) Nitric oxide inhibits the synthesis of type-II collagen without altering Col2A1 mRNA abundance: prolyl hydroxylase as a possible target. *Biochem J* 324:305-10.

Casini A, Ceni E, Salzano R, Biondi P, Parola M, Galli A, Foschi M, Caligiuri A, Pinzani M, Surrenti C (1997) Neutrophil-derived superoxide anion induces lipid peroxidation and stimulates collagen synthesis in human hepatic stellate cells: role of nitric oxide. *Hepatology* 25:361-7.

Catani M V et al. (1998) Inhibition of clotting factor XIII activity by nitric oxide. *Biochem Biophys Res Comm* 249: 275-8.

Cattell V (2002) Nitric oxide and glomerulonephritis. *Kidney Int* 61(3):816-21.

Cernadas M R, Sanchez de Miguel L, Garcia-Duran M, et al. Expression of constitutive and inducible nitric oxide synthases in the vascular wall of young and aging rats. Circ Res. 1998; 83:279-286

Chan D C, Earle K A, Zhao T L, Helfrich B, Zeng C, Baron A, Whitehead C M, Piazza G, Pamukcu R, Thompson W J, Alila H, Nelson P, Bunn P A Jr (2002) Exisulind in combination with docetaxel inhibits growth and metastasis of human lung cancer and prolongs survival in athymic nude rats with orthotopic lung tumors. *Clin Cancer Res* 8(3):904-12.

Chatziantoniou C, Boffa J J, Ardaillou R, Dussaule J C (1998) Nitric oxide inhibition induces early activation of type I collagen gene in renal resistance vessels and glomeruli in transgenic mice. Role of endothelin. *J Clin Invest* 101:2780-9.

Chen Y M, Wu K D, Tsai T J, Hsieh B S (1999) Pentoxifylline inhibits PDGF-induced proliferation of and TGF-beta-stimulated collagen synthesis by vascular smooth muscle cells. *J Mol Cell Cardiol* 31(4):773-83.

Cheng J W, Baldwin S N, Balwin S N. L-arginine in the management of cardiovascular diseases. Ann Pharmacother. 2001; 35:755-764

Chiche J D, Schlutsmeyer S M, Bloch D B, de la Monte S M, Roberts J D Jr, Filippov G, Janssens S P, Rosenzweig A, Bloch K D (1998) Adenovirus-mediated gene transfer of cGMP-dependent protein kinase increases the sensitivity of cultured vascular smooth muscle cells to the antiproliferative and pro-apoptotic effects of nitric oxide/cGMP. *J Biol Chem* 273(51):34263-71.

Chipev C C, Simman R, Hatch G, Katz A E, Siegel D M, Simon M (2000) Myofibroblast phenotype and apoptosis in keloid and palmar fibroblasts in vitro. *Cell Death Differ* 7(2): 166-76.

Chou T C, Yen M H, Li C Y, Ding Y A. Alterations of nitric oxide synthase expression with aging and hypertension in rats. Hypertension. 1998; 31:643-648.

Connat J L, Busseuil D, Gambert S, et al. Modification of the rat aortic wall during ageing; possible relation with decrease of peptidergic innervation. Anat Embryol. 2001; 204:455-468.

Connelly T J (1999) Development of Peyronie's and Dupuytren's diseases in an individual after single episodes of trauma: a case report and review of the literature. *J Am Acad Dermatol* 41(1):106-8

Corbin J D, Francis S H (1999) Cyclic GMP phosphodiesterase-5: target of sildenafil. *J Biol Chem* 274(20): 13729-32.

Craven P A, Studer R K, Felder J, Phillips S, DeRobertis F R (1997) Nitric oxide inhibition of transforming growth factor-beta and collagen synthesis in mesangial cells. *Diabetes* 46:671-81.

Csiszar A, Ungvari Z, Edwards J G, et al. Aging-induced phenotypic changes and oxidative stress impair coronary arteriolar function. Circ Res. 2002; 90:1159-1166.

Curtin J F, Donovan M, Cotter T G (2002) Regulation and measurement of oxidative stress in apoptosis. *J Immunol Methods* 265(1-2):49-72. Review.

Dambisya Y M et al (1996) A thromboelastography study on the in vitro effects of L-arginine and L-NG-nitro arginine methyl ester on human whole blood coagulation and fibrinolysis. *Blood Coagul Fibrinol* 7:678-83.

Darby I A, Bisucci T, Pittet B, Garbin S, Gabbiani G, Desmouliere A (2002) Skin flap-induced regression of granulation tissue correlates with reduced growth factor and increased metalloproteinase expression. *J Pathol,* 197(1): 117-27.

Davila H H, Magee T R, Rajfer J and Gonzalez-Cadavid N F. Gene transfer of antisense PIN (protein inhibitor of NOS) cDNA on erectile dysfunction in aged rats. American Urological Association Meeting, Chicago, Ill., 2003a.

Dávila, M. Ferrini, J. Rajfer, N. F. González-Cadavid. Fibrin induction of a Peyronie's-like plaque in the rat penile tunica albuginea. A new model for Peyronie's disease. Br. J. Urol. 91 (2003b) 830-838.

Demaree S R, Lawler J M, Linehan J, Delp M D. Ageing alters aortic antioxidant enzyme activities in Fischer-344 rats. Acta Physiol Scand. 1999; 166:203-208.

Desmoulière A (1995) Factors influencing myofibroblasts differentiation lduring wound healing and fibrosis. *Cell Biol Interntl* 19(5):471-476.

Desmouliere A, Xu G, Costa A M, Yousef I M, Gabbiani G, Tuchweber B (1999) Effect of pentoxifylline on early proliferation and phenotypic modulation of fibrogenic cells in two rat models of liver fibrosis and on cultured hepatic stellate cells. *J Hepatol* 30(4): 621-31.

Devine C J Jr, Somers K D, Jordan S G, Schlossberg S M (1997) Proposal: trauma as the cause of the Peyronie's lesion. *J Urol* 157(1):285-90.

Diegelmann R F (1997) Cellular and biochemical aspects of normal and abnormal wound healing: an overview. *J Urol* 157:298-302.

Duffield J S, Erwig L P, Wei X, Liew F Y, Rees A J, Savill J S (2000) Activated macrophages direct apoptosis and suppress mitosis of mesangial cells. *J Immunol* 164(4):2110-9.

Duncan M R, Berman B, Nseyo U O (1991) Regulation of the proliferation and biosynthetic activities of cultured human Peyronie's disease fibroblasts by interferons-alpha, -beta and -gamma. *Scand J Urol Nephrol* 25(2):89-94.

Dussaule J C, Tharaux P L, Boffa J J, Fakhouri F, Ardaillou R, Chatziantoniou C (2000) Mechanisms mediating the renal profibrotic actions of vasoactive peptides in transgenic mice. *J Am Soc Nephrol* Suppl 16:S124-8.

Ehrlich H P. (1997) Scar contracture: cellular and connective tissue aspects in yronie's disease. *J Urol* 157:316-9.

Eickelberg O, Kohler E, Reichenberger F, Bertschin S, Woodtli T, Erne P, Perruchoud A P, Roth M. Extracellular matrix deposition by primary human lung fibroblasts in response to TGF-beta1 and TGF-beta3. Am J. Physiol. 1999 May; 276(5 Pt 1): L814-24.

El-Sakka A I, Bakircioglu M E, Bhatnagar R S, Yen T S, Dahiya R, Lue T F (1999) The effects of colchicine on a Peyronie's-like condition in an animal model. *J Urol* 161: 1980-3.

El-Sakka A I, Hassan M U, Nunes L, Bhatnagar R S, Yen T S, Lue T F (1998) Histological and ultrastructural alterations in an animal model of Peyronie's disease. *British J Urol* 81:445-52.

El-Sakka A I, Hassoba H M, Chui R M, Bhatnagar R S, Dahiya R, Lue T F (1997b) An animal model of Peyronie's-like condition associated with an increase of transforming growth factor beta mRNA and protein expression. *J Urol* 158:2284-90.

El-Sakka A I; Hassoba H M; Pillarisetty R J; Dahiya R; Lue T F. (1997a) Peyronie's disease is associated with an increase in transforming growth factor-beta protein expression. *J Urol* 158:1391-4.

Essayan. Cyclic nucleotide phosphodiesterases. J. Allergy Clin. Immunol. 108 (2001) 671-680.

Fakhouri F, Placier S, Ardaillou R, Dussaule J C, Chatziantoniou C (2001) Angiotensin II activates collagen type I gene in the renal cortex and aorta of transgenic mice through interaction with endothelin and TGF-beta. *J Am Soc Nephrol* 12(12):2701-10.

Fan J, Kapus A, Li Y H, Rizoli S, Marshall J C, Rotstein O D (2000) Priming for enhanced alveolar fibrin deposition after hemorrhagic shock: role of tumor necrosis factor. *Am J Respir Cell Mol Biol* 22(4):412-21.

Faouzi S, Le Bail B, Neaud V, Boussarie L, Saric J, Bioulac-Sage P, Balabaud C, Rosenbaum J (1999) Myofibroblasts are responsible for collagen synthesis in the stroma of human hepatocellular carcinoma: an in vivo and in vitro study. *J Hepatol* 30:275-84.

Ferrini M, Magee T R, Vemet D, Hayden C, Rajfer J, Gonzalez-Cadavid N F (2001a) Aging-related expression of inducible nitric oxide sunthase (iNOS) and cytotoxicity markers in the rat penis. *Biol Reprod* 64:974-982.

Ferrini M, Wang C, Swerdloff R, Sinha Hikim A P, Gonzalez-Cadavid N F (2001b) Aging-related expression of inducible nitric oxide synthase (iNOS) and cytotoxicity markers in rat hypothalamic regions associated with male reproductive function. *Neuroendocr* 74:1-11.

Ferrini M G, Magee T R, Vernet D, Rajfer J, Gonzalez-Cadavid N F (2003) Penile neuronal nitric oxide synthase (PnNOS) and its regulatory proteins are present in hypothalamic and spinal cord regions involved in the control of penile erection. *J Compar Neurol,* 458:46-61.

Ferrini M G, Vernet D, Magee T R, Shahed A, Quian A, Rajfer J, Gonzalez-Cadavid N F (2002) Antifibrotic role of inducible nitric oxide synthase (iNOS). *Nitric Oxide* 6:1-12.

Fischer M, Wohlrab J, Marsch W (2001) Crux medicorum ulcerated radiation-induced fibrosis-successful therapy with pentoxifylline and vitamin E. *Eur J Dermatol* 1(1): 38-40.

Foresti R, Sarathchandra P, Clark J E, Green C J, Motterlini R (1999) Peroxynitrite induces haemoxygenase-1 in vascular endothelial cells: a link to apoptosis. *Br Biochem J* 339:729-736.

Formieri C, Quaglino D Jr, Mori G. Role of the extracellular matrix in age-related modifications of the rat aorta. Ultrastructural, morphometric, and enzymatic evaluations. Arterioscler Thromb. 1992; 12:1008-1016.

Forstermann U, Boissel J-P, Kleinert H (1998) Expressional control of the "constitutive" isoforms of nitric oxide synthase (NOS I and NOS II). *FASEB J* 12:773-790

Freireich et. al Cancer Chemother. Reports 50 (1966) 219-244.

Gabbiani G (1996) The cellular derivation and the life span of the myofibroblasts. *Path Res Pract* 192:701-711.

Garban H, Marquez D, Magee T, Moody J, Rajavashisht T, Rodriguez J A, Hung A, Vernet D, Rajfer J, Gonzalez-Cadavid N F (1997) Cloning of rat and human inducible penile nitric oxide synthase. Application for gene therapy of erectile dysfunction. *Biol Reprod* 56:954-963.

Garban H, Vernet D, Freedman A, Rajfer J, Gonzalez-Cadavid N F. Effect of aging on nitric oxide-mediated penile erection in the rat. Amer. J. Physiol. 1995; 268:H467-H475

Gelbard M K (1988) Dystrophic penile calcification in Peyronie's disease. *J Urol* 139(4):738-40.

Geller D A, Billiar T R (1998) Molecular biology of nitric oxide synthases. *Cancer Metast Rev* 17:7-23

Gelman J, Garban H, Shen R, Ng Ch, Cai L, Rajfer J, Gonzalez-Cadavid N F (1998) Transforming growth factor-1 (TGF beta1) and penile growth in the rat during sexual maturation. *J Androl* 19:50-57.

Gewaltig M T, Kojda G. Vasoprotection by nitric oxide: mechanisms and therapeutic potential. Cardiovasc Res. 2002; 55:250-260.

Gholami S S, Gonzalez-Cadavid N F, Lin C-S, Rajfer J, Lue T F (2002) Peyronie's Disease: A review. *J Urol,* 169: 1234-1241.

Goettsch W, Lattmann T, Amann K, et al. Increased expression of endothelin-1 and inducible nitric oxide synthase isoform II in aging arteries in vivo: implications for atherosclerosis. Biochem Biophys Res Commun. 2001; 280:908-913.

Gonca S, Ceylan S, Yardimoglu M, Dalcik H, Yumbul Z, Kokturk S, Filiz S (2000) Protective effects of vitamin E and selenium on the renal morphology in rats fed high-cholesterol diets. *Pathobiology* 68(6):258-63.

Gonzalez W, Fontaine V, Pueyo M E, et al. Molecular plasticity of vascular wall during N(G)-nitro-L-arginine methylester-induced hypertension: modulation of proinflammatory signals. Hypertension. 2000; 36:103-109.

González-Cadavid N F, Ignarro L, Rajfer J. Nitric oxide and cyclic GMP in the penis. Mol Urol. 1999; 3:51-59

Gonzalez-Cadavid, T. R. Magee, M. Ferrini, A. Qian, D. Vernet, J. Rajfer. Gene expression in Peyronie's disease. Int. J. Impot. Res. 14 (2002) 1-12.

Grein U, Schubert G E. Arteriosclerosis of penile arteries: histological findings and their significance in the treatment of erectile dysfunction. Urol Int. 2002; 68:261-264.

Grounds M D, White J D, Rosenthal N, Bogoyevitch M A. The role of stem cells in skeletal and cardiac muscle repair. *J Histochem Cytochem* 50(5): 589-610.

Haig D M, Thomson J, Percival A. (1994) The in-vitro detection and quantitation of ovine bone marrow precursors of multipotential colony-forming cells. *J Comp Pathol* 111 (1): 73-85.

Heigold S, Sers C, Bechtel W, Ivanovas B, Schafer R, Bauer G (2002) Nitric oxide mediates apoptosis induction selectively in transformed fibroblasts compared to nontransformed fibroblasts. *Carcinogenesis* 23(6):929-41.

Hellstrom W J, Bivalacqua T J (2000) Peyronie's disease: etiology, medical, and surgical therapy. *J Androl* 21(3):347-54.

Hellstrom W J G. (2001). Evaluation of nitric oxide synthase and arginase in the induction of a Peyronie's-like condition in the rat. J Androl 22:497-508

Herrick S, Blanc-Brude O, Gray A, Laurent G (1999) Fibrinogen. *Int J Biochem Cell Biol* 31(7):741-6.

Higuchi H, Granger D N, Saito H, Kurose I (1999) Assay of antioxidant and anti-inflammatory activity of nitric oxide in vivo. *Meth Enzymol* 301:424-436.

Hildebrand K A, Jia F, Woo S L. (2002) Response of donor and recipient cells after transplantation of cells to the ligament and tendon. *Microsc Res Tech* 1;58(1):34-8.

Hochberg D, Johnson C W, Chen J, Cohen D, Stern J, Vaughan E D, Poppas D, Felsen D (2000) Interstitial fibrosis of unilateral ureteral obstruction is exacerbated in kidneys of mice lacking the gene for inducible nitric oxide synthase. *Lab Invest* 11:1721-1728.

Hofmann F, Ammendola A, Schlossmann J (2000) Rising behind NO: cGMP-dependent protein kinases. *J Cell Sci* 113 (Pt 10):1671-6.

Hogaboam C M, Gallinat C S, Bone-Larson C, Chensue S W, Lukacs N W, Strieter R M, Kunkel S L (1998) Collagen deposition in a non-fibrotic lung granuloma model after nitric oxide inhibition. *Am J Pathol* 153:1861-72.

Holm, C. B. Andersen, S. Haunso, P. R. Hansen. Effects of L-arginine on vascular smooth muscle cell proliferation and apoptosis after balloon injury. Scand. Cardiovasc J. 34 2000) 28-32.

Holmdahl L, Kotseos K, Bergstrom M, Falk P, Ivarsson M L, Chegini N (2001) Overproduction of transforming growth factor-beta1 (TGF-beta1) is associated with adhesion formation and peritoneal fibrinolytic impairment. *Surgery* 129(5): 626-32.

Horio T, Nishikimi T, Yoshihara F, Matsuo H, Takishita S, Kangawa K (1999) Effects of adrenomedullin on cultured rat cardiac myocytes and fibroblasts. *Eur J Pharmacol* 382(1): 1-9.

Huff T, Muller C S, Otto A M, Netzker R, Hannappel E (2001) beta-Thymosins, small acidic peptides with multiple functions. Int J Biochem *Cell Biol* 33 (3): 205-20.

Huff T, Otto A M, Muller C S, Meier M, Hannappel E. (2002) Thymosin beta4 is released from human blood platelets and attached by factor XIIIa (transglutaminase) to fibrin and collagen. FASEB J. 16(7):691-6.

Hung A, Vernet D, Rajavashisht T, Rodriguez J A, Rajfer J, Gonzalez-Cadavid N F (1995) Expression of the inducible nitric oxide synthase in smooth muscle cells from the rat penile corpora cavernosa. *J Androl* 16:469-481

Ihrig M, Dangler C A, Fox J G. Mice lacking inducible nitric oxide synthase develop spontaneous hypercholesterolaemia and aortic atheromas. Atherosclerosis. 2001; 156:103-107.

Ikeda K, Nara Y, Tagami M, Yamori Y (1997) Nitric oxide deficiency induces myocardial infarction in hypercholesterolemic stroke-prone spontaneously hypertensive rats. *Clin Exptl Pharmacol Physiol* 24:344-8.

Intengan H D, Schiffrin E L. Structure and mechanical properties of resistance arteries in hypertension: role of adhesion molecules and extracellular matrix determinants. Hypertension. 2000; 36:312-318

Intengan H D, Schiffrin E L. Vascular remodeling in hypertension. Roles of apoptosis, inflammation, and fibrosis. Hypertension. 2001; 38:581-587.

Ito S, Ueda Y, Sugisaki T, Iidaka K (1992) Induction of glomerular injury by singlet oxygen. *Nephron* 60(2):204-9.

Iredale J P (1997) Tissue inhibitors of metalloproteinases in liver fibrosis. *Int J Biochem Cell Biol* 29(1):43-54.

Jarow J P, Lowe F C (1997) Penile trauma: an etiologic factor in Peyronie's disease and erectile dysfunction. *J Urol* 158(4):1388-90.

Jenkins J K, Huang H, Ndebele K, Salahudeen A K (2001) Vitamin E inhibits renal mRNA expression of COX II, HO I, TGFbeta, and osteopontin in the rat model of cyclosporine nephrotoxicity. *Transplantation* 71(2):331-4.

Jiaan D B, Seftel A D, Fogarty J, Hampel N, Cruz W, Pomerantz J, Zuik M, Monnier V M (1995) Age-related increase in an advanced glycation end product in penile tissue. *World J Urol* 13:369-375.

Jones R W, Rees R W, Minhas S, Ralph D, Persad R A, Jeremy J Y. Oxygen free radicals and the penis. Expert Opin Pharmacother 2002; 3:889-897

Kaikita K, Schoenhard J A, Painter C A, et al. Potential roles of plasminogen activator system in coronary vascular remodeling induced by long-term nitric oxide synthase inhibition. J Mol Cell Cardiol. 2002; 34:617-627

Kelley T J, Drumm M L (1998) Inducible nitric oxide synthase expression is reduced in cystic fibrosis murine and human airway epithelial cells. *J Clin Invest* 102:1200-7.

Khan M A, Thompson C S, Jeremy J Y, Mumtaz F H, Mikhailidis P, Morgan R J. The effect of superoxide dismutase on nitric oxide-mediated and electrical field-stimulated diabetic rabbit cavernosal smooth muscle relaxation. BJU Int. 2001; 87:98-103

Kibbe M, Billiar T, Tzeng E (1999) Inducible nitric oxide synthase and vascular injury. *Cardiovasc Res* 43:650-657.

Kim N N, Huang Y, Moreland R B, Kwak S S, Goldstein I, Traish A (2000) Cross-regulation of intracellular cGMP and cAMP in cultured human corpus cavernosum smooth muscle cells. *Mol Cell Biol Res Commun* 4(1): 10-4.

Kim P K, Zamora R, Petrosko P, Billiar T R (2001) The regulatory role of nitric oxide in apoptosis. *Int Immunopharmacol* 1(8):1421-41. Review.

Kitamoto S, Egashira K, Kataoka C, et al. Chronic inhibition of nitric oxide synthesis in rats increases aortic superoxide anion production via the action of angiotensin II. J. Hypertens. 2000; 18:1795-1800.

Klar S, Morrisey J J (1998) The role of growth, cytokines and vasoactive compounds in obstructive nephropathy. *Seminars Nephrol* 18(6):622-632.

Kleinman H K. (1999) Thymosin beta4 accelerates wound healing. J Invest Dermatol 113(3):364-8.

Kloen P (1999) New insights in the development of Dupuytren's contracture: a eview. *Br J Plast* Surg 52(8):629-35.

Badalamente M A, Hurst L C (1999) The biochemistry of Dupuytren's disease. *Hand Clin* 15(1):35-42, v-vi.

Kloner R A, Speakman M. Erectile dysfunction and atherosclerosis. Curr Atheroscler Rep. 2002; 4:397-401

Kolpakov V, Gordon D, Kulik T J (1995) Nitric oxide-generating compounds inhibit total protein and collagen synthesis in cultured vascular smooth muscle cells. *Circul Res* 76:305-9.

Krall J F, Fittingoff M, Rajfer J (1988) Characterization of cyclic nucleotide and inositol 1,4,5-trisphosphate-sensitive calcium-exchange activity of smooth muscle cells cultured from the human corpora cavernosa. *Biol Reprod* 39(4):913-22.

Kremer S, Breuer R, Lossos I S, Berkman N, Christensen T G, Connor M W, Goldstein R H, Or R (1999) Effect of immunomodulators on bleomycin-induced lung injury. *Respiration* 66(5):455-62.

Kuthe, A. Wiedenroth, H. J. Magert, S. Uckert, W. G. Forssmann, C. G. Stief, U. Jonas. Expression of different phosphodiesterase genes in human cavernous smooth muscle. J. Urol. 165 (2001) 280-283.

Lai, J. T. Fallon, J. Liu, J. Mangion, L. Gillam, D. Waters, C. Chen. Reversibility and pathohistological basis of left ventricular remodeling in hibernating myocardium. Cardiovasc. Pathol. 9 (2000) 323-335.

Larson J L, Pino M V, Geiger L E, Simeone C R (1996) The toxicity of repeated exposures to rolipram, a type IV phosphodiesterase inhibitor, in rats. *Pharmacol Toxicol* 78(1):44-9.

Lee P C, Shears L L 2nd, Billiar T R. Role of inducible nitric oxide synthase in transplant arteriosclerosis. Clin Exp Pharmacol Physiol. 1999; 26:1013-1015.

Lee S H, Zhang W, Choi J J, Cho Y S, Oh S H, Kim J W, Hu L, Xu J, Liu J, Lee J H (2002) Overexpression of the thymosin beta-10 gene in human ovarian cancer cells disrupts F-actin stress fiber and leads to apoptosis. *Oncogene* 21(37):5822.

Lee, G. T. Huang, L. H. Miau, L. L. Chiou, C. H. Chen, J. C. Sheu. Expression of matrix metalloproteinases in spontaneous regression of liver fibrosis. Hepatogastroenterology 48 (2001) 1114-1117.

Lee, H. B. Cottam, K. Houglum, D. B. Wasson, D. Carson, M. Chojkier. Pentoxifylline blocks hepatic stellate cell activation independently of phosphodiesterase inhibitory activity. Am. J. Physiol. 273 (1997) G1094-G1100.

Li Y Y, McTiernan C F, Feldman A M. Interplay of matrix metalloproteinases, tissue inhibitors of metalloproteinases and their regulators in cardiac matrix remodeling. Cardiovasc Res. 2000; 46:214-224.

Liang, E. Beshay, G. J. Prud'homme. The phosphodiesterase inhibitors pentoxifylline and rolipram prevent diabetes in NOD mice. Diabetes 47 (1998) 570-575.

Lin C S, Chow S, Lau A, Tu R, Lue T F (2002a) Human PDE5A gene encodes three PDE5 isoforms from two alternate promoters. *Int J Impot Res* 14(1):15-24.

Lin C S, Lau A, Tu R, Lue T F (2000a) Expression of three isoforms of cGMP-binding cGMP-specific phosphodiesterase (PDE5) in human penile cavernosum. *Biochem Biophys Res Commun* 268(2):628-35.

Lin C S, Lau A, Tu R, Lue T F (2000b) Identification of three alternative first exons and an intronic promoter of human PDE5A gene. *Biochem Biophys Res Commun* 268(2): 596-602.

Lin R J, Wu B N, Lo Y C, Shen K P, Lin Y T, Huang C H, Chen I (2002b) KMUP-1 relaxes rabbit corpus cavernosum smooth muscle in vitro and in vivo: involvement of cyclic GMP and K(+) channels. *Br J Pharmacol* 135(5): 1159-66.

Lin, Y. M. Chen, C. T. Chien, W. C. Chiang, C. C. Tsai, T. J. Tsai. Pentoxifylline attenuated the renal disease progression in rats with remnant kidney. J Am Soc Nephrol 13 (2002c) 2916-2929.

Loweth A C, Williams G T, Scarpello J H, Morgan N G (1997) Evidence for the involvement of cGMP and protein kinase G in nitric oxide-induced apoptosis in the pancreatic B-cell line, HIT-T15. *FEBS Lett* 400(3):285-8.

Ma K, Mallidis C, Artaza J Taylor W, Gonzalez-cadavid N F, Bhasin S (2001) Characterization of the 5' upstream regulatory region of the human myostatin gene. Regulation of myostatin gene transcription by dexamethasone. *Am J Physiol* 281:E1128-1136.

Magee, Ferrini, Davila, Zeller, Vernet, Sun, Lalani, Burnett, Rajfer, González-Cadavid (2003) Protein inhibitor of nitric oxide synthase (NOS) and the N-methyl-D-aspartate receptor are expressed in the rat and mouse penile nerves and colocalize with penile neuronal NOS." *Biol Reprod,* 68:478-488.

Magee T R, Ferrini M, Garban H, Vernet D, Mitani K, Rajfer J, Gonzalez-Cadavid N F (2002a) Gene therapy of erectile dysfunction in the rat with penile neuronal nitric oxide synthase cDNA. *Biol Reprod,* 67:1033-1041.

Magee T R, Qian A, Rajfer J, Levine L, Gonzalez-Cadavid N F (2002b) Gene expression profiles in the Peyronie's disease plaque. *Urology* 59:451-457.

Malinda K M, Sidhu G S, Mani H, Banaudha K, Maheshwari R K, Goldstein A L, Martin W, McAllister K H, Paisley K. NANC neurotransmission in the bovine retractor penis muscle is blocked by superoxide anion following inhibition of superoxide dismutase with diethyldithio carbamate. Neuropharmacology. 1994; 33:1293-1301

Martinez-Hernández, A (1994) "Repair, regeneration and fibrosis" in Pathology, $2^{nd}$ Edition, Chapter 3, page 69, J B Lippincott Ed, PA McCrudden R, Iredale J P (2000) Liver fibrosis, the hepatic stellate cell and tissue inhibitors of metalloproteinases. *Histol Histopathol* 15(4): 1159-68.

Melman A Pathophysiologic basis of erectile dysfunction. What can we learn from animal models? Int J Impot Res. 2001; 13:140-142

Melman A, Gingell J C. The epidemiology and pathophysiology of erectile dysfunction. J Urol. 1999; 161:5-11

Mignatti P, Rifkin D B, Welgus H G, Parks W C. (1996). Proteinases and tissue remodeling. In: The Molecular and cellular Biology of Wound repair. Clark R A F, editor, Plenum Press, N York & London, $2^{nd}$ ed, 427-474

Miller M J, Sandoval M (1999) Nitric Oxide. III. A molecular prelude to intestinal inflammation. *Am J Physiol* 276 (4 Pt 1): G795-9. Review.

Moilanen M, Pirila E, Grenman R, Sorsa T, Salo T. (2002) Expression and regulation of collagenase-2 (MMP-8) in head and neck squamous cell carcinomas. *J Pathol* 197(1):72-81.

Moody J, Vernet D, Laidlow S, Rajfer J, González-Cadavid N F (1997) Effect of long-term administration of L-arginine on penile erection and nitric oxide synthase in the rat. *J Urol* 158:942-947.

Moore M A, Schiffrin E L. Consortium for Southeastern hypertension control. Small artery remodeling in hypertension: can it be corrected?. Am J Med Sci. 2001; 322:7-11

Moreno H Jr, Metze K, Bento A C, Antunes E, Zatz R, de Nucci G (1996) Chronic nitric oxide inhibition as a model of hypertensive heart muscle disease. *Basic Res Cardiol* 91:248-55.

Morrissey J J, Ishidoya S, McCracken R, Klahr S (1996) Nitric oxide generation ameliorates the tubulointerstitial fibrosis of obstructive nephropathy. *J Am Soc Nephrol* 70:2202-12.

Mulhall J P, Branch J, Lubrano T, Shankey T V (2001a) Perturbation of cell cycle regulators in Peyronie's disease. *Int J Impot Res* 13 Suppl 5:S21-8.

Mulhall J P, Thom J, Lubrano T, Shankey T V (2001b) Basic fibroblast growth factor expression in Peyronie's disease. *J Urol* 165(2):419-23

Mulhall, M. S. Anderson, T. Lubrano, T. V. Shankey. Peyronie's disease cell culture models: phenotypic, genotypic and functional analyses. Int. J. Impot. Res. 14 (2002) 397-405.

Muralidhar S, Gulati M, Kumar B, Sharma S K, Suman K, Roy P B (1996) An ultrasonographic study of Peyronie's disease. Australas Radiol 40(2): 106-8.

Muriel P (1998a) Nitric oxide protection of rat liver from lipid peroxidation, collagen accumulation, and liver damage induced by carbon tetrachloride. *Biochem Pharmacol* 56:773-9.

Muriel P, Castro V. (1998b) Effects of S-Adenosyl-L-methionine and Interferon-2b on Liver damage induced by bile duct ligation in rats. J Appl Toxicol 18:143-147

Nagase H, Brew K (2002) Engineering of tissue inhibitor of metalloproteinases mutants as potential therapeutics. *Arthritis Res* Suppl 3:S51-61.

Nanji, K. Jokelainen, G. K. Lau, A. Rahemtulla, G. L. Tipoe, R. Polavarapu, E. N. Lalani. Arginine reverses ethanol-induced inflammatory and fibrotic changes in liver despite continued ethanol administration. J. Pharmacol. Exp. Ther. 299 (2001) 832-839.

Nathan C (1997a) Inducible nitric oxide synthase: What difference does it make? *J Clin Invest* 100:2417-2423.

Nishio K. Fukushima, M. Shiozaki, Y. Watanabe. Nitric oxide donor SNAP induces apoptosis in smooth muscle cells through cGMP-independent mechanism. Biochem. Biophys. Res. Commun. 221 (1996) 163-168.

Niu X L, Yang X, Hoshiai K, et al. Inducible nitric oxide synthase deficiency does not affect the susceptibility of mice to atherosclerosis but increases collagen content in lesions. Circulation. 2001; 103:1115-1120.

Noss M B, Day N S, Christ G J, Melman A (2000) The genetics and immunology of Peyronie's disease. *Int J Impot Res* 12 Suppl 4:S127-32

Noujaim D, van Golen C M, van Golen K L, Grauman A, Feldman E L. (2002) N-Myc and Bcl-2 coexpression induces MMP-2 secretion and activation in human neuroblastoma cells. Oncogene 21(29): 4549-57.

Numaguchi K, Egashira K, Takemoto M, Kadokami T, Shimokawa H, Sueishi K, Takeshita A (1995) Chronic inhibition of nitric oxide synthesis causes coronary microvascular remodeling in rats. *Hypertension* 26:957-62.

Okamoto T, Akaike T, Nagano T, Miyajima S, Suga M, Ando M, Ichimori K, Maeda H (1997) Activation of human neutrophil procollagenase by nitrogen dioxide and peroxynitrite: a novel mechanism for procollagenase activation involving nitric oxide. *Arch Biochem Biophys* 342:261-74.

Okazaki I. (2001) Selective induction of tissue inhibitor of metalloproteinase-1 in bleomycin-induced pulmonary fibrosis. *Am J Respir Cell Mol. Biol.* 24(5): 599-607.

Orucevic A, Bechberger J, Green A M, Shapiro R A, Billiar T R, Lala P K (1999) Nitric-oxide production by murine mammary adenocarcinoma cells promotes tumor-cell invasiveness. *Int J Cancer* 81(6): 889-96.

Owens M W, Milligan S A, Grisham M B (1996) Inhibition of pleural mesothelial cell collagen synthesis by nitric oxide. *Free Radic Biol Med* 21(5): 601-7.

Pandey K N, Nguyen H T, Li M, Boyle J W (2000) Natriuretic peptide receptor-A negatively regulates mitogen-activated protein kinase and proliferation of mesangial cells: role of cGMP-dependent protein kinase. *Biochem Biophys Res Commun* 271(2): 374-9.

Pechanova, I. Bernatova, V. Pelouch, P. Babal. L-NAME-induced protein remodeling and fibrosis in the rat heart. Physiol. Res. 48 (1999) 353-362.

Peters, W. A. Border, N. A. Noble. Tandem antifibrotic actions of L-arginine supplementation and low protein diet during the repair phase of experimental glomerulonephritis. Kidney Int. 57 (2000) 992-1001.

Piazza, W. J. Thompson, R. Pamukcu, H. W. Alila, C. M. Whitehead, L. Liu, J. R. Fetter, W. E. Gresh Jr, A. J. Klein-Szanto, D. R. Farnell, I. Eto, C. J. Grubbs. Exisulind, a novel proapoptotic drug, inhibits rat urinary bladder tumorigenesis. Cancer Res. 61 (2001) 3961-3968.

Poli G (2000) Pathogenesis of liver fibrosis: role of oxidative stress. *Mol Aspects Med* 21:49-98.

Powel D W, Mifflin R C, Valentich J D, Ceowe S E, Saada J I, West A B (1999) Myofibroblasts. Paracrine cells important in health and disease. *Am J Physiol* 277:C1-C19.

Preaux A M, D'ortho M P, Bralet M P, Laperche Y, Mavier P. (2002) Apoptosis of human hepatic myofibroblasts promotes activation of matrix metalloproteinase-2. *Hepatology* 36(3): 615-622.

Pye D, Watt D J (2001) Dermal fibroblasts participate in the formation of new muscle fibres when implanted into regenerating normal mouse muscle. *J Anat* 198:163-173

Raetsch, J. D. Jia, G. Boigk, M. Bauer, E. G. Hahn, E. O. Riecken, D. Schuppan. Pentoxifylline downregulates profibrogenic cytokines and procollagen I expression in rat secondary biliary fibrosis. Gut 50 (2002) 241-247.

Redondo J, Bishop J E, Wilkins M R (1998) Effect of atrial natriuretic peptide and cyclic GMP phosphodiesterase inhibition on collagen synthesis by adult cardiac fibroblasts. *Br J Pharmacol* 124(7):1455-62.

Reimund J M, Dumont S, Muller C D, Kenney J S, Kedinger M, Baumann R, Poindron P, Duclos B. In vitro effects of oxpentifylline on inflammatory cytokine release in patients with inflammatory bowel disease Gut 1997 April;40(4):475-80

Reisz-Porszasz S, Bhasin S, Artaza J N, Shen R, Sinha-Hikim I, Houge A, Gonzalez-Cadavid N F (2002) Reduction of skeletal muscle mass in a transgenic mouse that hyperexpresses myostatin in the muscle. *FASEB J.*

Rizvi M A; Myers P R (1997) Nitric oxide modulates basal and endothelin-induced coronary artery vascular smooth muscle cell proliferation and collagen levels. *J Mol Cell Cardiol* 29:1779-89.

Rizzoni D, Rodella L, Porteri E, et al. Time course of apoptosis in small resistance arteries of spontaneously hypertensive rats. J Hypertens. 2000; 18:885-891.

Robert L. Aging of the vascular-wall and atherosclerosis. Exp Gerontol. 1999; 34:491-501

Rogers R S, Graziottin T M, Lin C-S, Kan Y W, Lue T F. Intracavernosal vascular endothelial growth factor (VEGF) injection and adeno-associated virus-mediated VEGF gene therapy prevent and reverse venogenic erectile dysfunction in rats. Intl J Impot Res. 2003; 15:26-37

Roy S G, Nozaki Y, Phan S H (2001) Regulation of -smooth muscle actin gene expression in myofibroblast differentiation from rat lung fibroblasts. *Intl J Biochem & Cell Biol* 33:723-734

Ryter S W, Choi A M (2002) Heme oxygenase-1: molecular mechanisms of gene expression in oxygen-related stress. *Antioxid Redox Signal* 4(4):625-32.

Salanova, S-Y. Chun, S. Iona, C. Puri, M. Stefanini, M. Conti. Type 4 cyclic adenosine monophosphate-specific phosphodiesterases are expressed in discrete subcellular compartments during rat spermiogenesis. Endocrinology 140 (1999) 2297-2306

Sampson, J. M. Hinton, C. J. Garland. Evidence for expression and function of phospho-diesterase type 5 (PDE-V) in rat resistance arteries. Br. J. Pharmacol. 132 (2001) 13-7.

Sasaki K, Hattori T, Fujisawa T, Takahashi K, Inoue H, Takigawa M (1998) Nitric oxide mediates interleukin-1-induced gene expression of matrix metalloproteinases and basic fibroblast growth factor in cultured rabbit articular chondrocytes. *J Biochem* 123:431-9.

Sauzeau, M. Rolli-Derkinderen, S. Lehoux, G. Loirand, P. Pacaud. Sildenafil prevents change in RhoA expression induced by chronic hypoxia in rat pulmonary artery. Circ Res. 2003 Aug. 28 [Epub ahead of print]

Schade I, Roth-Eichhorn S, Kasper M, Kuss H, Plotze K, Funk R H, Schuler S (2002) Benefit of phosphodiesterase 4 inhibitors as supplemental therapy after lung transplantation concerning their antiproliferative effects: an experimental study using a heterotopic rodent model. *Transplantation* 74(3):326-34.

Schaffer M R, Tantry U, Efron P A, Ahrendt G M, Thornton F J, Barbul A (1997a) Diabetes-impaired healing and reduced wound nitric oxide synthesis: a possible pathophysiologic correlation. *Surgery* 121:513-9.

Schaffer M R; Efron P A; Thornton F J; Klingel K; Gross S S; Barbul A (1997b) Nitric oxide, an autocrine regulator of wound fibroblast synthetic function. *J Immunol* 158:2375-81.

Schuppan D, Koda M, Bauer M, Hahn E G (2000) Fibrosis of liver, pancreas and intestine: common mechanisms and clear targets? *Acta Gastroenterol Belg* 63(4):366-70.

Schwarzer U, Sommer F, Klotz T, Braun M, Reifenrath B, Engelmann U (2001) The prevalence of Peyronie's disease: results of a large survey. *BJU Int* 88(7):727-30.

Sebkhi, J. W. Strange, S. C. Phillips, J. Wharton, M. R. Wilkins. Phosphodiesterase type 5 as a target for the treatment of hypoxia-induced pulmonary hypertension. Circulation 107 (2003) 3230-3235.

Sherratt J A, Dallon J C (2002) Theoretical models of wound healing: past successes and future challenges. *C R Biol* 325(5):557-64.

Shimizu, Y. Kobayashi, Y. Oki, T. Kawasaki, T. Yoshimi, H. Nakamura. OPC-13013, a cyclic nucleotide phosphodiesterase type III, inhibitor, inhibits cell proliferation and transdifferentiation of cultured rat hepatic stellate cells. Life Sci. 64 (1999) 2081-2088.

Sikka, W. J. Hellstrom. Role of oxidative stress and antioxidants in Peyronie's disease. Int. J. Impot. Res. 14 (2002) 353-360.

Simko, J. Simko. The potential role of nitric oxide in the hypertrophic growth of the left ventricle. Physiol. Res. 49 (2000) 37-46.

Singer A J, Clark R A F (1999) Cutaneous wound healing. *N Engl J Med* 341:738-746.

Sinnaeve P, Chiche J D, Gillijns H, Van Pelt N, Wirthlin D, Van De Werf F, Collen D, Bloch K D, Janssens S (2002) Overexpression of a constitutively active protein kinase G mutant reduces neointima formation and in-stent restenosis. *Circulation* 105(24):2911-6.

Sirotkin A V, Makarevich A V, Pivko J, Kotwica J, Genieser H, Bulla J (2000) Effect of cGMP analogues and protein kinase G blocker on secretory activity, apoptosis and the cAMP/protein kinase A system in porcine ovarian granulose cells in vitro. *J Steroid Biochem Mol Biol* 74(1-2):1-9.

Smith, M. Liu. Impaired cutaneous wound healing after sensory denervation in developing rats: effects on cell proliferation and apoptosis. Cell Tissue Res. 307 (2002) 281-291.

Smythe G M, Hodgetts S I, Grounds M D (2000) Immunobiology and the future of myoblast transfer therapy. *Mol Ther* 1(4): 304-13.

Somers K D, Dawson D M (1997) Fibrin deposition in Peyronie's disease plaque. *J Urol* 157:311-5.

Somers K D, Dawson D M, Wright G L, Leffell M S, Rowe M J, Bluemink G G, Vande Berg J S, Gleischman S H, Devine C J, Horton C E (1982) Cell culture of Peyronie's disease plaque and normal penis tissue. *J Urology* 127:585-588.

Song, D. Wang, X. Cui, W. Hu. The protective action of taurine and L-arginine in radiation pulmonary fibrosis. *J. Environ. Pathol. Toxicol. Oncol.* 17 (1998) 151-157.

Sosne G, Szliter E A, Barrett R, Kernacki K A, Kleinman H, Hazlett L D. (2002) Thymosin beta 4 promotes corneal wound healing and decreases inflammation in vivo following alkali injury. *Exp Eye Res* 74(2): 293-9.

Souness, D. Aldous, C. Sargent. Immunosuppressive and anti-inflammatory effects of cyclic AMP phosphodiesterase (PDE) type 4 inhibitors. Immunopharmacology 47 (2000) 127-162.

Stausbol-Gron B, Bentzen S M, Overgaard J (1998) Characterization and radiosensitivity of fibroblasts derived from squamous cell carcinomas of the head and neck, and the surrounding oral mucosa. *Acta Oncol* 37(7-8): 697-700.

Sullivan M E, Keoghane S R, Miller M A. Vascular risk factors and erectile dysfunction. BJU Int. 2001; 87:838-845

Susic, A. Francischetti, E. D. Frohlich. Prolonged L-arginine on cardiovascular mass and myocardial hemodynamics and collagen in aged spontaneously hypertensive rats and normal rats. Hypertension 33 (1999) 451-455.

Taimor G, Hofstaetter B, *Piper* H M (2000) Apoptosis induction by nitric oxide in adult cardiomyocytes via cGMP-signaling and its impairment after simulated ischemia. *Cardiovasc Res* 45(3):588-94.

Takemoto M, Egashira K, Tomita H, Usui M, Okamoto H, Kitabatake A, Shimokawa H, Sueishi K, Takeshita A. (1997) Chronic angiotensin-converting enzyme inhibition and angiotensin II type 1 receptor blockade: effects on cardiovascular remodeling in rats induced by the long-term blockade of nitric oxide synthesis. *Hypertension* 30:1621-7.

Takuma K, Lee E, Enomoto R, Mori K, Baba A, Matsuda T (2001) Ibudilast attenuates astrocyte apoptosis via cyclic GMP signalling pathway in an in vitro reperfusion model. *Br J Pharmacol* 133(6):841-8.

Tanaka H, Nagai E, Murata H, Tsubone T, Shirakura Y, Sugiyama T, Taguchi T, Kawai S. (2001) Involvement of bone morphogenic protein-2 (BMP-2) in the pathological ossification process of the spinal ligament. *Rheumatology* (Oxford) 40(10): 1163-8.

Tanaka H, Wakisaka A, Ogasa H, Kawai S, Liang C T. (2002) Effect of IGF-I and PDGF administered in vivo on the expression of osteoblast-related genes in old rats. *J Endocrinol* 174(1):63-70.

Tao J, Mallat A, Gallois C, Belmadani S, Mery P F, Nhieu J T, Pavoine C, Lotersztajn S (1999) Biological effects of C-type natriuretic peptide in human myofibroblastic hepatic stellate cells. *J Biol Chem* 274(34):23761-9.

Tarcin, K. Avsar, L. Demirturk, M. Gultepe, B. K. Oktar, O. C. Ozdogan, O. Tarcin, H. Baloglu, A. K. Gurbuz. In vivo inefficiency of pentoxifylline and interferon-alpha on hepatic fibrosis in biliary-obstructed rats: assessment by tissue collagen content and prolidase activity. J Gastroenterol Hepatol 18 (2003) 437-444.

Tharaux P L, Chatziantoniou C, Casellas D, Fouassier L, Ardaillou R, Dussaule J C (1999) Vascular endothelin-1 gene expression and synthesis and effect on renal type I collagen synthesis and nephroangiosclerosis during nitric oxide syntahse inhibition in rats. *Circulation* 99(16):2185-91.

Tharaux P L, Chatziantoniou C, Fakhouri F, Dussaule J C (2000) Angiotensin II activates collagen I gene through a mechanism involving the MAP/ER kinase pathway. *Hypertension* 36(3): 330-6.

Thirunavukkarasu K, Halladay D L, Miles R R, Geringer C D, Onyia J E. (2002) Analysis of regulator of G-protein signaling-2 (RGS-2) expression and function in osteoblastic cells. J Cell Biochem 85(4): 837-50.

Thompson W J, Piazza G A, Li H, Liu L, Fetter J, Zhu B, Sperl G, Ahnen D, Pamukcu R. Exisulind induction of apoptosis involves guanosine 3',5'-cyclic monophosphate phosphodiesterase inhibition, protein kinase G activation, and attenuated beta-catenin. *Cancer Res* 2000 60(13):3338-42

Thornton F J, Schaffer M R, Witte M B, Moldawer L L, MacKay S L D, Abouhamze A, Tannahill C, Barbul A (1998) Enhanced collagen accumulation following direct transfection of the inducible nitric oxide synthase gene in cutaneous wounds. *Biochem Biophys Res Commun* 246:654-659.

Tian, J. Liu, P. B. Bitterman, R. J. Bache. Mechanisms of cytokine induced NO-mediated cardiac fibroblast apoptosis. Am. J. Physiol. 283 (2002) H1958-H1967.

Tiggelman A M, Linthorst C, Boers W, Brand H S, Chamuleau R A (1997) transforming growth factor-beta-induced collagen synthesis by human liver myofibroblasts is inhibited by alpha2-macroglobulin. *J Hepatology* 26:1220-8.

Tomasek J J, Vaugham M B, Haaksma C J (1999) Cellular structure and biology of Dupuytren's disease. *Hand Clinics* 15(1):21-34.

Tomasek, G. Gabbiani, B. Hinz, C. Chaponnier, R. A. Brown. Myofibroblasts and mechano-regulation of connective tissue remodelling. Nat. Rev. Mol. Cell. Biol. 3 (2002) 349-363.

Turko, S. A. Ballard, S. H. Francis, J. D. Corbin. Inhibition of cyclic GMP-binding cyclic GMP-specific phosphodiesterase (Type 5) by sildenafil and related compounds. Mol. Pharmacol. 56 (1999) 124-130.

Uckert S, Kuthe A, Stief C G, Jonas U (2001) Phosphodiesterase isoenzymes as pharmacological targets in the treatment of male erectile dysfunction. *World J Urol* 19(1):14-22.

Usui M, Egashira K, Kitamoto S, et al. Pathogenic role of oxidative stress in vascular angiotensin-converting enzyme activation in long-term blockade of nitric oxide synthesis in rats. Hypertension. 1999; 34:546-551.

Van de Water L (1997) Mechanisms by which fibrin and fibronectin appear in healing wounds: implications for Peyronie's disease. *J Urol* 157:306-10.

van der Loo B, Labugger R, Skepper J N, et al. Enhanced peroxynitrite formation is associated with vascular aging. J Exp Med. 2000; 192:1731-1744.

van der Zee E, Everts V, Beertsen W (1997) Cytokines modulate routes of collagen breakdown. *J Clin Periodontol* 24(5):297-305

Vernet D, Bonavera J J, Swerdloff R S, Gonzalez-Cadavid N F, Wang C (1998) Spontaneous expression of inducible nitric oxide synthase (iNOS) in the hypothalamus and other brain regions of aging rats. *Endocrinology* 139:3254-61.

Vernet D, Ferrini M G, Valente E, et al. Effect of nitric oxide on fibroblast differentiation into myofibroblasts in cell cultures from the Peyronie's fibrotic plaque and in its rat model in vivo. Nitric Oxide. 2002; 7:262-276.

Wahl S M (1997) Inflammation and growth factors *J Urol* 157:303-305.

Walker G A, Guerrero I A, Leinwand L A (2001) Myofibroblasts: molecular crossdressers. *Curr Top Dev Biol* 51:91-107.

Wang C, Hikim A S, Ferrini M, Bonavera J J, Vernet D, Leung A, Lue Y H, Gonzalez-Cadavid N F, Swerdloff R S (2002a) Male reproductive ageing: using the brown Norway rat as a model for man. *Novartis Found Symp* 242:82-95.

Wang, H. K. Ho, P. S. Lin, S. P. Schwarzacher, M. J. Pollman, G. H. Gibbons, P. S. Tsao, J. P. Cooke. Regression of atherosclerosis: role of nitric oxide and apoptosis. Circulation 99 (1999) 1236-1241.

Wang, P. Wu, J. G. Myers, A. Stamford, R. W. Egan, M. M. Billah. Characterization of human, dog and rabbit corpus cavernosum type 5 phosphodiesterases. Life Sci. 68 (2001) 1977-1987.

Wang, Y. Vodovotz, P. K. Kim, R Zamora, T. R. Billiar. Mechanisms of hepatoprotection by nitric oxide. Ann. N.Y. Acad. Sci. 962 (2002b) 415-422.

Watanabe T, Niioka M, Ishikawa A, Hozawa S, Arai M, Maruyama K, Okada A, Okazaki I. (2001) Dynamic change of cells expressing MMP-2 mRNA and MT1-MMP mRNA in the recovery from liver fibrosis in the rat. *J Hepatol.* 35(4): 465-73.

Watanabe, S. Inai, K. Jinnouchi, S. Bada, A. Hess, O. Michel, T. Yagi. Nuclear-factor kappa B (NF-kappa B)-inducible nitric oxide synthase (iNOS/NOS II) pathway damages the stria vascularis in cisplatin-treated mice. Anticancer Res. 22 (2002) 4081-4085.

Westenfeld R, Gawlik A, de Heer E, Kitahara M, Abou-Rebyeh F, Floege J, Ketteler M (2002) Selective inhibition of inducible nitric oxide synthase enhances intraglomerular coagulation in chronic anti-Thy 1 nephritis. *Kidney Int* 61(3): 834-8.

Windmeier C, Gressner A M. Pharmacological aspects of pentoxifylline with emphasis on its inhibitory actions on hepatic fibrogenesis. Gen Pharmacol 1997 August;29(2): 181-96

Wollert K C, Fiedler B, Gambaryan S, Smolenski A, Heineke J, Butt E, Trautwein C, Lohmann S M, Drexler H (2002) Gene transfer of cGMP-dependent protein kinase I enhances the antihypertrophic effects of nitric oxide in cardiomyocytes. *Hypertension* 39(1):87-92.

Wu J, Zern M A (2000) Hepatic stellate cells: a target for the treatment of liver fibrosis. *J Gastroenterol* 35(9):665-72.

Yaguchi T, Fukuda Y, Ishizaki M, Yamanaka N. Immunohistochemical and gelatin zymography studies for matrix metalloproteinases in bleomycin-induced pulmonary fibrosis. *Pathol Int.* 1998 December;48(12):954-63.

Yamasaki K, Edington H D J, Mc Closky C, Tzeng E, Lizanova A, Kovesdi I, Steed D L, Billiar T R (1998) Reversal of impaired wound repair in iNOS-deficient mice by topical adenoviral-mediated iNOS gene transfer. *Am J Physiol* 101: 967-971.

Zalba G, Beaumont J, San Jose G, Fortuno A, Fortuno M A, Diez J. Vascular oxidant stress: molecular mechanisms and pathophysiological implications. J Physiol Biochem. 2000; 56:57-64

Zhang H Y, Phan S H (1999) Inhibition of myofibroblast apoptosis by transforming growth factor beta (1). *Am J Respir Cell Mol Biol* 21(6):658-65.

Zuk P A, Zhu M, Mizuno H, Huang J, Futrell J W, Katz A J, Benhaim P, Lorenz H P, Hedrick M H (2001) Multilineage cells from human adipose tissue: implications for cell-based therapies. *Tissue Engineering* 7(2): 211-228.

TABLE 1

| Protein/gene | n* | Dupuytren Mean ± SE | n** | Peyronie Mean ± SE |
|---|---|---|---|---|
| matrix metalloproteinase 2 | 9 | 29 ± 10 | 2 | 4.7 ± 2.6 |
| matrix metalloproteinase 9 | | | 2 | 50.8 ± 0.8 |
| thymosin beta-10 (TMSB10) | 9 | 5.9 ± 2.6 | 5 | 5.5 ± 1.3 |
| thymosin beta 4 | 8 | 5.9 ± 1.5 | 5 | 2.5 ± 0.9 |
| prothymosin alpha | 2 | 2.6 ± 0.0 | 2 | 6.2 ± 3.8 |
| osteoblast specific factor 1 (OSF-1) | 5 | 5.6 ± 1.4 | 3 | 4.3 ± 0.5 |
| osteoblast specific factor 2 (OSF2) | 4 | 26.7 ± 12.7 | | |
| rho GDP dissociation inihibitor 1 (RHO-GDI 1) | 6 | 3.5 ± 1.4 | 2 | 18.3 ± 2.4 | n* = 9 patients
n** = 10 patients

TABLE 2

| | INTIMA MEDIA THICKNESS | | |
|---|---|---|---|
| | YOUNG (μm) | OLD (μm) | OLD + L-NIL (μm) |
| AORTA | 73.4 ± 8.6** | 93.0 ± 6.6** | 85.2 ± 6.6 |
| FEMORAL | 49.7 ± 7.1 | 63.5 ± 2.4 | 51.8 ± 4.6 |
| PENILE DORSAL | 17.0 ± 2.3 | 18.6 ± 1.4 | 23.6 ± 3.3 |
| BULBO URETHRAL | 10.5 ± 1.3 | 10.1 ± 1.6 | 9.9 ± 0.7 |

| | LUMEN DIAMETER | | |
|---|---|---|---|
| | YOUNG (μm) | OLD (μm) | OLD + L-NIL (μm) |
| PENILE DORSAL | 100.8 ± 13.7 | 118.7 ± 6.6 | 105.5 ± 16. |
| BULBO URETHRAL | 40.1 ± 5.6 | 42.6 ± 6.8 | 47.3 ± 6.6 |

What is claimed is:

1. A method comprising:
   a) administering a cyclic guanosine 3', 5'-monophosphate (cGMP) type 5 phosphodiesterase (PDE 5) inhibitor according to a continuous long-term regimen to an individual with at least one of a penile tunical fibrosis and corporal tissue fibrosis; and
   b) arresting or regressing the at least one of the penile tissue fibrosis and corporal tissue fibrosis, wherein the PDE-5 inhibitor is administered at a dosage up to 1.5 mg/kg/day for not less than 45 days.

2. The method of claim 1, wherein administering the PDE-5 inhibitor according to a continuous long-term regimen comprises oral administering of sildenafil, tadalafil or vardenafil.

3. The method of claim 1, wherein the penile tissue fibrosis is Peyronie's disease plaque, or penile corporal veno-occlussive dysfunction.

4. The method of claim 1, wherein the PDE-5 inhibitor is administered orally, by injection, or by local administration to a penis.

5. The method of claim 1, wherein administering according to a continuous long-term regimen comprises administering for months or years.

* * * * *

UNITED STATES PATENT AND TRADEMARK OFFICE
CERTIFICATE OF CORRECTION

PATENT NO. : 8,133,903 B2  
APPLICATION NO. : 10/779069  
DATED : March 13, 2012  
INVENTOR(S) : Nestor F. Gonzalez-Cadavid et al.

Page 1 of 1

It is certified that error appears in the above-identified patent and that said Letters Patent is hereby corrected as shown below:

In the Claims, Column 68, Claim 1, line 29, please delete "tissue" and insert --tunical--.

Signed and Sealed this
Eleventh Day of September, 2012

David J. Kappos
*Director of the United States Patent and Trademark Office*